US009532956B2

(12) United States Patent
Radovic-Moreno et al.

(10) Patent No.: US 9,532,956 B2
(45) Date of Patent: Jan. 3, 2017

(54) PH SENSITIVE BIODEGRADABLE POLYMERIC PARTICLES FOR DRUG DELIVERY

(75) Inventors: Aleksandar Filip Radovic-Moreno, State College, PA (US); Weiwei Gao, Cambridge, MA (US); Archana Swami, Everett, MA (US); Gershon Golomb, Efrat (IL); Robert S. Langer, Newton, MA (US); Omid C. Farokhzad, Chestnut Hill, MA (US)

(73) Assignees: Massachusetts Institute of Technology, Cambridge, MA (US); The Brigham and Women's Hospital Inc., Boston, MA (US)

( * ) Notice: Subject to any disclaimer, the term of this patent is extended or adjusted under 35 U.S.C. 154(b) by 164 days.

(21) Appl. No.: 12/762,348

(22) Filed: Apr. 18, 2010

(65) Prior Publication Data
US 2011/0065807 A1 Mar. 17, 2011

Related U.S. Application Data

(60) Provisional application No. 61/212,989, filed on Apr. 18, 2009.

(51) Int. Cl.
| | | |
|---|---|---|
| *A61K 47/30* | (2006.01) | |
| *G01N 21/76* | (2006.01) | |
| *A61K 9/51* | (2006.01) | |
| *A61K 48/00* | (2006.01) | |
| *C12N 15/11* | (2006.01) | |
| *C12N 15/115* | (2010.01) | |

(52) U.S. Cl.
CPC .............. *A61K 9/51* (2013.01); *A61K 48/0008* (2013.01); *C12N 15/111* (2013.01); *C12N 15/115* (2013.01); *C12N 2310/11* (2013.01); *C12N 2310/14* (2013.01); *C12N 2310/16* (2013.01); *C12N 2320/32* (2013.01)

(58) Field of Classification Search
CPC .............................. A61K 9/51; A61K 48/0008
See application file for complete search history.

(56) References Cited

U.S. PATENT DOCUMENTS

| 2005/0118252 A1* | 6/2005 | Bae et al. ............... 424/450 |
| 2009/0023673 A1 | 1/2009 | Manoharan |
| 2011/0250284 A1* | 10/2011 | Lavik et al. .............. 424/497 |

FOREIGN PATENT DOCUMENTS

| WO | 2005021730 | 3/2005 |
| WO | 2006052285 | 5/2006 |
| WO | 2010008792 | 1/2010 |

OTHER PUBLICATIONS

General et al (International Journal of Pharmaceutics. 2001; 230: 11-24).*
Pelisek et al (Journal of Gene Medicine. 2006; 8: 186-197).*
Bikram et al (Macromolecules. 2004; 37: 1903-1916).*
Kang et al. (Fundamental Biomedical Technologies, 2008, vol. 4, 161-199).*
Bird, et al., "Single-chain antigen-binding proteins", Science, 242:423-26 (1988).
Blum, et al., "High loading efficiency and turnable release of plasmid DNA encapsulated in submicron particles fabricated from PLGA conjugated with poly-L-lysine", J controlled Release, 129(1):66-72 (2008).
Ceroritelli, et al., "PEG-SS-PPS: reduction-sensitive disulfide block copolymer vesicles for intracellular drug delivery", Biomacromolecules, 8:1966-72 (2007).
Cheng, et al., "Formulation of functionalized PLGA-PEG nanoparticles for in vivo targeted drug delivery", Biomaterials, 28:869-76 (2007).
Elbashir, et al., "Functional anatomy of siRNAs for mediating efficient RNAi in *Drosophila melanogaster* embryo lysate", EMBO J, 20:6877-88 (2001).
Farokhzad, et al., "Targeted nanoparticle-aptamer bioconjugates for cancer chemotherapy in vivo", PNAS, 103:6315-20 (2006).
Gonzalez and Tsien, et al., "Voltage sensing by fluorescence resonance energy transfer in single cells", Biophys. J., 69:1272-80 (1995).
Gu, et al., "Precise engineering of targeted nanoparticles by using self-assembled biointegrated block copolymers", PNAS, 105:2586-91 (2007).
Hanes, et al., "Polymer microspheres for vaccine delivery", Pharm. Biotechnol., 6:389-412 (1997).
Hong, et al., "Direct comparison of liposomal doxorubicin with or without polyethylene glycol coating in C-26 tumor-bearing mice: is surface coating with polyethylene glycol beneficial", Clin Cancer Res., 5:3645-52 (1999).

(Continued)

*Primary Examiner* — Scott Long
(74) *Attorney, Agent, or Firm* — Pabst Patent Group LLP

(57) ABSTRACT

The present invention generally relates to polymers and particles, such as nanoparticles. The particles and polymers generally include one or more buffering components. Additionally, the particles and polymers may include two or more components that impart useful properties (functionalities). The particles and polymers, for example, may include a buffering component and a degradable component. As described herein, the particles and polymers may also include a hydrophilic component and/or a cleavable bond component. The particles and polymers described herein have been found to be particularly effective when used for delivery of one or more agents, such as one or more pharmaceutical agents. Other aspects of the invention are directed to methods of using or administering such particles or polymers, kits involving such particles or polymers, and the like. The present invention also relates to particles containing a cleavable bond component and one or more fluorescence resonance energy transfer (FRET) pairs as well as methods of detecting the cleavage of the cleavable bond component of such particles.

19 Claims, 33 Drawing Sheets

(56) References Cited

OTHER PUBLICATIONS

Huston, et al., "Protein engineering of antibody binding sites: recovery of specific activity in an anti-digoxin single-chain fv analogue produced in *Escherichia coli*", PNAS, 85:5879-83 (1988).

Langer, "Biomaterials in drug delivery and tissue engineering: one lavoratory\s experience", Acc. Chem. Res., 33:94-101 (2000).

Owens and Peppas, "Opsonization, biodistribution, and pharmacokinetics of polymeric nanoparticles", Intl. J. Pharm., 307:93-102 (2005).

Romberg, et al., "Sheddable coatings for long-circulating nanoparticles", Pharm. Res., 25:55-71 (2008).

Takae, et al., "PEG-detachable polyplex micelles based on disulfide-linked block catiomers as bioresponsive nonviral gene vectors", J of Am Chem. Science, 130:6001-9 (2008).

Ulrich, et al., "Polymeric systems for controlled drug release", Chemical Review, 99:3181 (1999).

Yang, et al., Evaluation of disulfide reduction during receptor-mediated endocytosis by using FRET imaging PNAS, 103:13872-77 (2006).

Zhang, et al., "Nanoparticles in medicine: therapeutic applications and developments", Clin. Pharmacol. Ther., 83:761-69 (2008).

Zhou, et al., "Investigation on a novel core-coated microspheres protein delivery system", J. Control Release, 75:27-36 (2001).

\* cited by examiner

- Endosomal delivery by sponge effect:
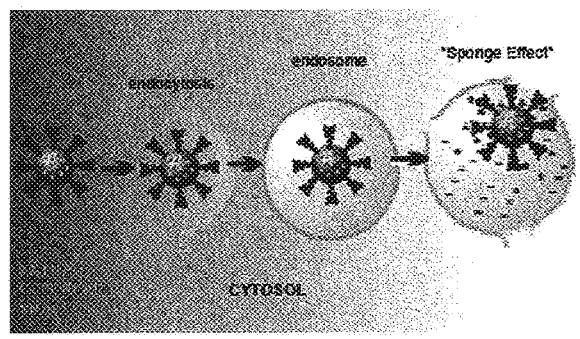
- PEG detachment to enhance delivery:
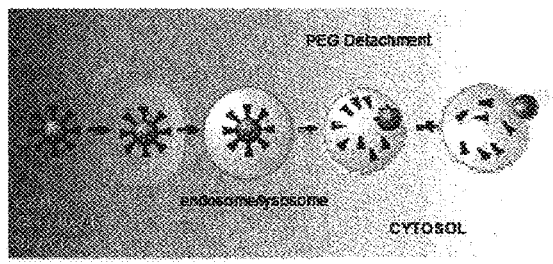
FIG. 10

Co-delivery of Both Hydrophilic and Hydrophobic Agents

Fluorescence Co-localization in HUVEC Cells

- Nuclei
- Cytoskeleton
- Dextran-Rhodamine
- PLGA-Alexa 488

Figure S1. MALDI-TOF analysis of intermediates in PEG conjugation to form the FRET-bearing PEG.

Figure S2. MALDI-TOF analysis of folate conjugation to PEG. The starting material is BOC-NH-PEG-NH$_2$. The conjugation introduces a folic acid molcule to the PEG chain, followed by the BOC deprotection. The molecular weight increase of 328 Da from the spectra is consistent with the theoretical calculation.

Figure S3. HPLC analysis of folate conjugation with PEG. In (a), free folic acid elutes at 29 minutes. After conjugation in (b), folate elutes at 36 and 38 minutes, respectively, corresponding to the two conjugation isomers.

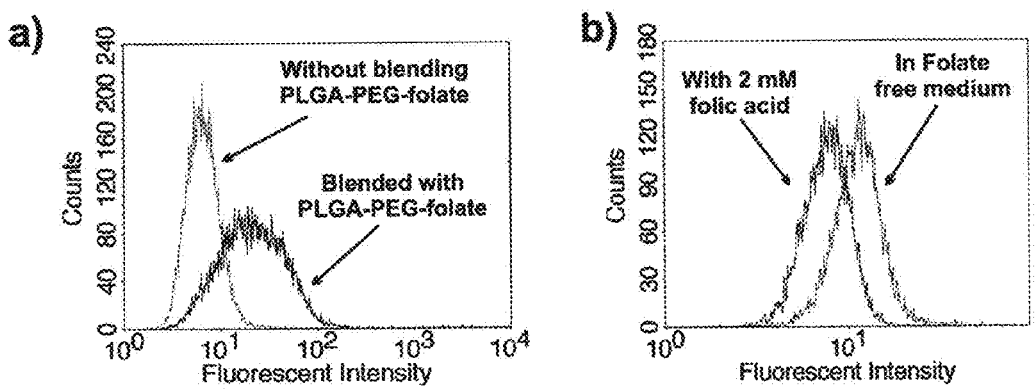

Figure S3. NP uptake is analyzed using flow cytometry by encapsulating PLGA-Alexa488. (a) NP formulated by blending 1.5 mg PLGA-mPEG and 1.5 mg PLGA-PEG-folate shows enhanced uptake, compared with NPs formulated by 3 mg PLGA-mPEG only. (b) NP is formulated by blending 1.5 mg PLGA-mPEG and 1.5 mg PLGA-PEG-folate. The uptake is inhibited by adding 2 mM folic acid to the cell culture medium. In all NP formulations, 0.3 mg PLGA-Alexa488 is blended. The incubation time is 6 hours.

FIG. 30

*Neutral lipids don't affect generation of cationic charge at low pH*

PH SENSITIVE BIODEGRADABLE POLYMERIC PARTICLES FOR DRUG DELIVERY

RELATED APPLICATIONS

This application claims the benefit under 35 U.S.C. §119 of U.S. provisional application 61/212,989, filed Apr. 18, 2009, the contents of which are incorporated herein by reference in their entirety.

GOVERNMENT FUNDING

This invention was made with Government support under Grant No. 5-U54-CA119349-03, awarded by the National Institutes of Health (NIH). The Government has certain rights in this invention.

FIELD OF INVENTION

The present invention generally relates to particles, such as nanoparticles, the polymers of which the particles are comprised, as well as to compositions thereof. The present invention also generally relates to methods of using the compositions provided for delivery of agents, such as one or more pharmaceutical agents (e.g., one or more drugs). The present invention also generally relates to compositions comprising particles with a cleavable bond component and a fluorescence resonance energy transfer (FRET) pair as well as to methods of detecting the cleavage of the cleavable bond component of such particles.

BACKGROUND

The delivery of a drug to a patient with controlled-release of the active ingredient has been an active area of research for decades and has been fueled by the many recent developments in polymer science and the need to deliver more labile pharmaceutical agents such as nucleic acids, proteins and peptides. Even so, there is an ongoing need for new particles that can provide improved drug delivery.

SUMMARY OF THE INVENTION

The present invention generally relates to particles, such as nanoparticles, as well as to polymers of which the particles may be comprised. The particles can, preferably, respond to both pH and redox changes. The subject matter of the present invention is also directed to various uses of these compositions. The subject matter of the present invention is also directed to compositions comprising particles with a cleavable bond component and a fluorescence resonance energy transfer (FRET) pair as well as to methods of detecting the cleavage of the cleavable bond component of such particles. The subject matter of the present invention involves, in some cases, interrelated products, alternative solutions to a particular problem, and/or a plurality of different uses of one or more systems and/or articles.

In some aspects, a particle or polymer comprising a buffering component is provided. In some embodiments, the buffering component is on the surface of the particle and/or is within the particle. In other embodiments, the buffering component is conjugated (covalently or noncovalently) to a particle or polymer, complexed to a particle or polymer or is encapsulated within a particle or by a polymer. In some embodiments, the particle further comprises one or more pharmaceutical agents (e.g., one or more drugs).

In some embodiments, the particle is organic. In other embodiments, the particle is inorganic. In still other embodiments, the particle is made up of both organic and inorganic materials.

In some embodiments, the particle comprises one or more lipids. In some embodiments, the one or more lipids are one or more lipidoids (i.e., lipid-like materials originally discovered for the delivery of RNAi therapeutics). Examples of lipidoids and lipid-based formulations are provided in U.S. Published Application 20090023673. In other embodiments, the one or more lipids are one or more cationic lipids.

In some embodiments, the particle further comprises one or more polymers. In some of these embodiments, one or more of the lipids are conjugated to or complexed to one or more of the polymers. In some embodiments, the conjugation is covalent. In other embodiments, the one or more lipids encapsulate the one or more polymers. In further embodiments, the one or more polymers encapsulate the one or more lipids.

In some embodiments, the particle comprises one or more polymers. In some embodiments, the particle comprises one or more cationic polymers. In some embodiments, the cationic polymer is chitosan, protamine, polylysine, polyhistidine, polyarginine or poly(ethylene)imine. In other embodiments, the one or more polymers contain the buffering component, degradable component, hydrophilic component, cleavable bond component or some combination thereof.

In other embodiments, the particle comprises one or more polymers. The polymers can be any of the polymers described herein.

In some embodiments, the particles or some portion thereof are degradable. In other embodiments, the lipids and/or polymers of the particles are degradable.

In some embodiments, any of these particles can comprise a buffering component. In other embodiments, any of the particles can comprise a buffering component and a degradable component. In still other embodiments, any of the particles can comprise a buffering component and a hydrophilic component. In yet other embodiments, any of the particles can comprise a buffering component and a cleavable bond component. In yet other embodiments, any of the particles can comprise a buffering component, a degradable component and a hydrophilic component. In still other embodiments, any of the particles can comprise a buffering component, a degradable component and a cleavable bond component. In further embodiments, any of the particles can comprise a buffering component, a hydrophilic component and a cleavable bond component. In yet another embodiment, any of the particles can comprise a buffering component, a degradable component, a hydrophilic component and a cleavable bond component. In some embodiments, the particle is composed of one or more polymers that contain any of the aforementioned combinations of components. Such polymers and compositions comprising the polymers are also provided herein.

In some embodiments, one or more of the polymers of a particle comprise a degradable component, buffering component, cleavable bond component and hydrophilic component in this order as recited. In other embodiments, one or more of the polymers comprise a degradable component, cleavable bond component, buffering component and hydrophilic component in this order as recited.

In some embodiments, the cleavable bond component is pH active, enzymatically active or redox-active.

In some embodiments, the zeta potential difference of the particle at physiological pH relative to at an endosomal pH or the pH at the site of a tumor is at least 5 millivolts (mV). In some embodiments, the zeta potential of the particle is more positive (or less negative) at an endosomal pH or the pH at the site of a tumor than at physiological pH. In some embodiments, the zeta potential is more positive (or less negative) by at least 5 mV, 10 mV, 15 mV, 20 mV, 25 mV, 30 mV, 35 mV, 40 mV, 45 mV, 50 mV, 55 mV, 60 mV, 65 mV, 70 mV, 75 mV, 80 mV, 85 mV, 90 mV, 95 mV, 100 mV or more. In some embodiments, the zeta potential of the particle is measured in water. In other embodiments, the zeta potential is measured in phosphate buffered saline (PBS). In some embodiments, the particle is neutral or negatively charged at physiological pH and positively charged at an endosomal pH or the pH at the site of a tumor. In other embodiments, the particle is more positively charged (or less negatively charged) at an endosomal pH or the pH at the site of a tumor than at physiological pH. In some embodiments, the particle or a portion thereof is also able to escape the endosome. In some embodiments, the escape from the endosome occurs after the cleavage of one or more hydrophilic components of the particle.

In some embodiments, the particle further comprises one or more pharmaceutical agents. In some embodiments, the one or more pharmaceutical agents are on the surface and/or within the particle. In other embodiments, the one or more pharmaceutical agents are conjugated to, complexed to or encapsulated within the particle. In further embodiments, the one or more pharmaceutical agents are conjugated to, complexed to or encapsulated by the one or more lipids or polymers of the particles. In some embodiments, the conjugation is covalent.

In some embodiments, the one or more pharmaceutical agents are negatively charged. In some embodiments, the negatively charged pharmaceutical agent is a nucleic acid. In some embodiments, the nucleic acid is an antisense oligonucleotide, aptamer or interfering RNA (RNAi). In some embodiments, the nucleic acid is a microRNA (miRNA), shRNA or siRNA. In further embodiments, one or more of the pharmaceutical agents are a protein or peptide. In some embodiments, the protein is an antibody. In some embodiments, one or more of the pharmaceutical agents are a hydrophobic agent or a hydrophilic agent (e.g., a hydrophobic drug or hydrophilic drug, respectively). In some embodiments, the one or more of the pharmaceutical agents are a hydrophobic agent and a hydrophilic agent (e.g., a hydrophobic drug and/or a hydrophilic drug).

In some embodiments, one or more pharmaceutical agents are released from the particle when the particle is in a cell or other desired location (e.g., within the endosome or at the site of a tumor).

In some embodiments, the buffering component comprises one or more chemical groups with a pKa between 5 and 7.6. In other embodiments, the buffering component comprises one or more chemical groups with a pKa of between 5.5 and 7.5. In some embodiments, such buffering components include an imidazole, pyridine, any molecule that contains imidazole and/or pyridine or a derivative thereof. Other examples are described elsewhere herein. In other embodiments, the buffering component comprises one or more histidines. In still other embodiments, the buffering component comprises one or more arginines. In further embodiments, the buffering component comprises one or more lysines. In some embodiments, the buffering component comprises a copolymer of histidine and arginine, histidine and lysine, or arginine and lysine. In some embodiments, the buffering component comprises 1-200 histidines. In other embodiments, the buffering component comprises 1-200 arginines. In further embodiments, the buffering component comprises 1-200 lysines. In some embodiments, the buffering component is not polylysine. In other embodiments, the buffering component does not comprise lysine.

In some embodiments, the degradable component is a polyester, poly(ortho ester), poly(ethylene imine), poly (caprolactone), polyanhydride, poly(acrylic acid), polyglycolide or poly(urethane). In some embodiments, the degradable component is poly(lactic acid) (PLA) or poly(lactic-co-glycolic acid) (PLGA).

In some embodiments, the ratio of the degradable component to buffering component is 1:1 to 100:1 by weight. In other embodiments, the ratio of the degradable component to buffering component is 1:100 to 1:1 by weight. In some embodiments, the ratio of the degradable component to buffering component is 5:1 by weight.

In some embodiments, the buffering component is conjugated to the degradable component via the cleavable bond component (e.g., in one or more of the polymers of a particle). In some embodiments, the conjugation is covalent. In some embodiments, the cleavable bond component is pH active, enzymatically active or redox-active.

In some embodiments, the hydrophilic component is a polyalkylene glycol or a polyalkylene oxide. In some embodiments, the polyalkylene glycol is polyethylene glycol (PEG). In other embodiments, the polyalkylene oxide is polyethylene oxide (PEO). In some embodiments, the hydrophilic component is conjugated to the buffering component via the cleavable bond component. In some embodiments, the cleavable bond component is cleaved (e.g., from one or more of the polymers of a particle) in an endosome or at an endosomal pH or at the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5.

In some embodiments, at least 0.1% to 50% of the particle weight is the weight of the one or more agents (e.g., one or more pharmaceutical agents).

In some embodiments, the one or more agents of the particle are encapsulated (e.g., by one or more of the lipids or polymers of the particle) at an efficiency of at least 10%, 20%, 30%, 40%, 50%, 60%, 70%, 80%, 90%, 95% or 99%.

In some embodiments, the particle targets a specific cell or tissue. In some embodiments, the particle (e.g., one or more of the polymers of a particle) further comprise a targeting moiety. In some embodiments, the targeting moiety is a small molecule, protein, glycoprotein, polynucleotide, polypeptide, peptide or carbohydrate. In other embodiments, the targeting moiety is an aptamer, affibody (simple proteins composed of a three-helix bundle based on the scaffold of one of the IgG-binding domains of Protein A), nanobody (single domain antibodies or VHH antibodies derived from camels), Adnectin™, antibody or antigen-binding fragment thereof. In some embodiments, the targeting moiety is a Spiegelmer®, a SMIP™ therapeutic or a SCORPION™ therapeutic.

In further embodiments, the antibody is a single chain antibody. In yet other embodiments, the antigen-binding fragment is Fab, $Fab_2$ or Fc. In some embodiments, the single chain antibody is a single chain Fab, single chain $Fab_2$ or single chain Fc.

In other embodiments, the particle does not comprise a targeting moiety. In some embodiments, the one or more polymers of a particle do not comprise a targeting moiety. In still other embodiments, the particle itself targets a specific cell or tissue without comprising a specific targeting moiety (i.e., the properties of the particle itself are such that the particle targets a specific cell or tissue without the addition of a targeting moiety that would be added solely or primarily for the purpose of targeting the particle to a specific cell or tissue or improving its ability to target thereto).

In some embodiments, the particle further comprises a blending polymer. In some embodiments, the blending polymer is a copolymer comprising a degradable component and hydrophilic component. In some embodiments, the degradable component of the blending polymer is a polyester, poly(ortho ester), poly(ethylene imine), poly(caprolactone), polyanhydride, poly(acrylic acid), polyglycolide or poly(urethane). In some embodiments, the degradable component of the blending polymer is poly(lactic acid) (PLA) or poly(lactic-co-glycolic acid) (PLGA). In some embodiments, the hydrophilic component of the blending polymer is a polyalkylene glycol or a polyalkylene oxide. In some embodiments, the polyalkylene glycol is polyethylene glycol (PEG). In other embodiments, the polyalkylene oxide is polyethylene oxide (PEO).

In some embodiments, when the particle comprises more than one polymer, the polymers are the same type of polymer. In other embodiments, when the particle comprises more than one polymer, at least two of the polymers are not the same type of polymer.

In some embodiments, the particle has an average characteristic dimension of less than about 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm or 20 nm. In other embodiments, the particle has an average characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm. In further embodiments, the particle has an average characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm.

In some aspects, a composition comprising one or more of the particles described herein are provided. In some embodiments, the composition further comprises a pharmaceutically acceptable carrier. In other embodiments, the composition is formulated for in vivo administration.

In some embodiments, the net charge of the particle or polymer is more positive (or less negative) at an endosomal pH or at the pH at the site of a tumor than at physiological pH. In some embodiments, the net charge of the particle or polymer is more positive (or less negative) at a pH in the range of 4-6.5 than at a pH in the range of 7-8. In other embodiments, the net charge of the particle or polymer is more positive (or less negative) at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 than at a pH of 7, 7.1, 7.2, 7.3, 7.4, 7.5, 7.6, 7.7, 7.8, 7.9 or 8. In other embodiments, the particle or polymer is neutral or is negatively charged at physiological pH and is positively charged at an endosomal pH or at the pH at the site of a tumor. In some embodiments, the particle or polymer is more positively charged (or less negatively charged) at an endosomal pH or at the pH at the site of a tumor than at physiological pH.

In some embodiments, the particle or polymer encapsulates one or more agents at an efficiency of at least 10%, 20%, 30%, 40%, 50%, 60%, 70%, 80%, 90%, 95% or 99%.

In other embodiments, the particle or polymer is also able to effect release of one or more pharmaceutical agents in a cell (e.g., in an endosome or at an endosomal pH) or at the site of a tumor.

In some embodiments, the particle or polymer further comprises a targeting moiety. In some embodiments, the targeting moiety is a small molecule, protein, glycoprotein, polynucleotide, polypeptide, peptide or carbohydrate. In other embodiments, the targeting moiety is an aptamer, affibody, nanobody, Adnectin™, antibody or antigen-binding fragment thereof. In further embodiments, the antibody is a single chain antibody. In some embodiments, the antigen-binding fragment is Fab, $Fab_2$ or Fc. In other embodiments, the single chain antibody is a single chain Fab, single chain $Fab_2$ or single chain Fc. In some embodiments, the targeting moiety is a Spiegelmer®, a SMIP™ therapeutic or a SCORPION™ therapeutic.

In some embodiments, the particle or polymer does not comprise a targeting moiety.

In some embodiments, the particle or polymer further comprises one or more pharmaceutical agents.

In further aspects, a composition comprising one or more of the particles or one or more of the polymers described herein is provided. In some embodiments, the composition further comprises a pharmaceutically acceptable carrier. Such compositions are, in some embodiments, formulated for in vivo administration.

In some embodiments, the composition further comprises one or more pharmaceutical agents. In some embodiments, one or more of the pharmaceutical agents are conjugated to the particle or polymer. In some embodiments, the conjugation is covalent. In other embodiments, one or more of the pharmaceutical agents are encapsulated within the particle or by the polymer. In further embodiments, one or more of the pharmaceutical agents are complexed to the particle or polymer.

In some embodiments, one or more of the pharmaceutical agents are a hydrophobic agent or a hydrophilic agent (e.g., a hydrophobic drug or hydrophilic drug, respectively). In other embodiments, the one or more pharmaceutical agents are a hydrophobic agent and a hydrophilic agent. In other embodiments, one or more of the pharmaceutical agents are negatively charged. In further embodiments, one or more of the pharmaceutical agents are a protein, peptide or nucleic acid. In some embodiments, the protein is an antibody. In other embodiments, the nucleic acid is an antisense oligonucleotide, aptamer or interfering RNA (RNAi). In further embodiments, the nucleic acid is a microRNA (miRNA), shRNA or siRNA.

In other aspects, a method comprising administering a composition described herein to a subject is provided. In some embodiments, the subject has cancer, an inflammatory disease, an infectious disease, a cardiovascular condition or a neurological condition.

In further aspects, a method comprising contacting one or more cells with a particle or composition comprising a particle is provided. In some embodiments, the method further comprises determining the level of delivery of one or more pharmaceutical agents. In some embodiments, the step of determining the level of delivery of one or more pharmaceutical agents comprises determining the amount of the one or more pharmaceutical agents that was introduced into the cell. In other embodiments, the step of determining the level of delivery of the one or more pharmaceutical agents, e.g., a nucleic acid, comprises determining the level of transfection and/or level of gene silencing.

In some embodiments, one or more of the pharmaceutical agents are a hydrophobic agent or a hydrophilic agent (e.g., a hydrophobic drug or hydrophilic drug, respectively). In other embodiments, the one or more of the pharmaceutical agents are a hydrophobic agent and a hydrophilic agent. In other embodiments, one or more of the pharmaceutical agents are negatively charged. In further embodiments, one or more of the pharmaceutical agents are a protein, peptide or nucleic acid. In some embodiments, the protein is an antibody. In other embodiments, the nucleic acid is an antisense oligonucleotide, aptamer or interfering RNA (RNAi). In further embodiments, the nucleic acid is a microRNA (miRNA), shRNA or siRNA.

In some aspects, a method comprising producing a particle or polymer with a buffering component and a degradable component and determining the charge of the particle or polymer at a pH in the range of pH 3-pH 9 is provided. In some embodiments, the pH is 4, 4.5, 5, 5.5, 6, 6.5, 7, 7.5, 8, 8.5 or 9. In some embodiments, the pH is physiological pH. In some embodiments, the pH is in the range of 7-8. In other embodiments, the pH is 7, 7.1, 7.2, 7.3, 7.4, 7.5, 7.6, 7.7, 7.8, 7.9 or 8. In other embodiments, the pH is an endosomal pH or the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5.

In some embodiments, the charge of the particle or polymer is determined at another pH in the range of pH 3-pH 9. In some embodiments, the pH is 4, 4.5, 5, 5.5, 6, 6.5, 7, 7.5, 8, 8.5 or 9. In some embodiments, the other pH is an endosomal pH or the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5. In other embodiments, the other pH is physiological pH. In some embodiments, the pH is in the range of 7-8. In other embodiments, the pH is 7, 7.1, 7.2, 7.3, 7.4, 7.5, 7.6, 7.7, 7.8, 7.9 or 8.

In any of the above embodiments, the method can further comprise selecting a particle or polymer that is more positive (or less negative) at an endosomal pH or the pH at the site of a tumor than at physiological pH. In some embodiments, the method comprises selecting a particle or polymer that is more positive (or less negative) at a pH in the range of 4-6.5 than in the range of 7-8. In other embodiments, the method comprises selecting a particle or polymer that is more positive (or less negative) at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 than 7, 7.1, 7.2, 7.3, 7.4, 7.5, 7.6, 7.7, 7.8, 7.9 or 8.

In some embodiments, the particle or polymer further comprises a hydrophilic component and/or a cleavable bond component.

In some embodiments, the particle or polymer has one or more pharmaceutical agents conjugated thereto. In some embodiments, the conjugation is covalent. In other embodiments, one or more of the pharmaceutical agents are encapsulated within the particle or by the polymer. In further embodiments, the particle or polymer is complexed to one or more of the pharmaceutical agents.

In some embodiments, one or more of the pharmaceutical agents is a hydrophobic agent or hydrophilic agent (e.g., a hydrophobic drug or hydrophilic drug, respectively). In other embodiments, one or more of the pharmaceutical agents are negatively charged. In further embodiments, one or more of the pharmaceutical agents are a protein, peptide or nucleic acid. In some embodiments, the protein is an antibody. In other embodiments, the nucleic acid is an antisense oligonucleotide, aptamer or interfering RNA (RNAi). In further embodiments, the nucleic acid is a microRNA (miRNA), shRNA or siRNA.

In further aspects a method comprising producing a particle with a buffering component and a degradable component, and determining the zeta potential of the particle at a pH in the range of pH 3-pH 9 is provided. In some embodiments, the pH is 4, 4.5, 5, 5.5, 6, 6.5, 7, 7.5, 8, 8.5 or 9. In some embodiments, the pH is physiological pH. In some embodiments, the pH is in the range of 7-8. In other embodiments, the pH is 7, 7.1, 7.2, 7.3, 7.4, 7.5, 7.6, 7.7, 7.8, 7.9 or 8. In other embodiments, the pH is an endosomal pH or the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5.

In some embodiments, the zeta potential of the particle is determined at another pH in the range of pH 3-pH 9. In some embodiments, the pH is 4, 4.5, 5, 5.5, 6, 6.5, 7, 7.5, 8, 8.5 or 9. In some embodiments, the other pH is an endosomal pH or the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5. In other embodiments, the other pH is physiological pH. In some embodiments, the pH is in the range of 7-8. In other embodiments, the pH is 7, 7.1, 7.2, 7.3, 7.4, 7.5, 7.6, 7.7, 7.8, 7.9 or 8.

In any of these embodiments, the method can further comprise selecting a particle with a zeta potential that is more positive (or less negative) at an endosomal pH or the pH at the site of a tumor than at physiological pH. In some embodiments, the method comprises selecting a particle with a zeta potential that is more positive (or less negative) at a pH in the range of 4-6.5 than in the range of 7-8. In other embodiments, the method comprises selecting a particle with a zeta potential that is more positive (or less negative) at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 than 7, 7.1, 7.2, 7.3, 7.4, 7.5, 7.6, 7.7, 7.8, 7.9 or 8.

In some embodiments, where the zeta potential is determined at two different pHs, the method can further comprise selecting a particle with a zeta potential difference of at least 5 mV, 10 mV, 15 mV, 20 mV, 25 mV, 30 mV, 35 mV, 40 mV, 45 mV, 50 mV, 55 mV, 60 mV, 65 mV, 70 mV, 75 mV, 80 mV, 85 mV, 90 mV, 95 mV, 100 mV or more. In some embodiments, the zeta potential is measured at an endosomal pH or the pH at the site of a tumor and at physiological pH. In other embodiments, the zeta potential is measured at a pH in the range of 4-6.5 and at a pH in the range of 7-8. In further embodiments, the pH is measured at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 and at a pH of 7, 7.1, 7.2, 7.3, 7.4, 7.5, 7.6, 7.7, 7.8, 7.9 or 8. In these embodiments, the zeta potential difference is the difference between the two zeta potentials that are measured.

In some embodiments, the zeta potential is measured in water or PBS.

In some embodiments, the particle further comprises a hydrophilic component and/or a cleavable bond component.

In some embodiments, the particle further comprises one or more pharmaceutical agents. In some embodiments, one or more of the pharmaceutical agents are a hydrophobic drug or hydrophilic drug. In other embodiments, the one or more pharmaceutical agents are a hydrophobic agent and a hydrophilic agent (e.g., a hydrophobic drug and a hydrophilic drug). In still other embodiments, one or more of the pharmaceutical agents is negatively charged. In further embodiments, one or more of the pharmaceutical agents is a protein, peptide or nucleic acid. In some embodiments, the protein is an antibody. In other embodiments, the nucleic acid is an antisense oligonucleotide, aptamer or interfering RNA (RNAi). In further embodiments, the nucleic acid is a microRNA (miRNA), shRNA or siRNA.

In another aspect, a composition comprising a particle that comprises a cleavable bond component and a fluorescence resonance energy transfer (FRET) pair is provided. In some embodiments, the donor of the FRET pair is Oregon Green-488 (OG-488), Alexa 488, Alexa 546, BODIPY 493, Oyster 556, Fluor (FAM), Cy3 or TMR (TAMRA) and the acceptor of the FRET pair is Dabcyl, Cy5, Alexa 594, Alexa 647 or Oyster 656. In other embodiments, the donor is OG488 and the acceptor is Dabcyl.

In some embodiments, the particle comprises the molecule of Formula 1.

In further embodiments, the particle is a microparticle, nanoparticle or picoparticle. In still other embodiments, the particle is a liposome, polymeric micelle, lipoplex or polyplex. In some embodiments, the particle comprises one or more lipids. In some embodiments, the one or more lipids are lipidoids. In other embodiments, the particle further comprises one or more polymers. In still other embodiments, one or more of the lipids are conjugated to one or more of the polymers. In some embodiments, the particle comprises one or more polymers. In some embodiments, one or more of the lipids or polymers are degradable.

In other embodiments, the one or more polymers comprise a polyester, poly(ortho ester), poly(ethylene imine), poly(caprolactone), polyanhydride, poly(acrylic acid), polyglycolide or poly(urethane). In still other embodiments, the one or more polymers comprise poly(lactic acid) (PLA) or poly(lactic-co-glycolic acid) (PLGA). In some embodiments, the one or more polymers comprise polyalkylene glycol or a polyalkylene oxide. In some embodiments, the polyalkylene glycol is polyethylene glycol (PEG) or the polyalkylene oxide is polyethylene oxide (PEO).

In some embodiments, the cleavable bond component is pH active, enzymatically active or redox-active.

In another aspect, a composition comprising the molecule of Formula 1 is provided.

In still another aspect, a method of detecting cleavage of a particle that comprises a cleavable bond component and a fluorescence resonance energy transfer (FRET) pair is provided. In some embodiments, the method comprises exposing the particle to conditions under which cleavage occurs, and detecting or measuring the level of fluorescent emission. In other embodiments, the cleavable bond component is pH active, enzymatically active or redox-active. In further embodiments, the conditions under which cleavage occurs are reducing conditions. In some embodiments, the particle is any of the particles that comprise a cleavable bond component and a FRET pair provided herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 10 illustrates endosomal delivery by "sponge effect" and enhanced delivery with PEG detachment, each in accordance with one embodiment of the invention.

FIG. 30 provides results from an analysis of NP uptake using flow cytometry by encapsulating PLGA-Alexa488, each in accordance with one embodiment of the invention. (A) NP formulated by blending 1.5 mg PLGA-mPEG and 1.5 mg PLGA-PEG-folate showed enhanced uptake compared with NPs formulated by 3 mg PLGA-mPEG only. (B) NP formulated by blending 1.5 mg PLGA-mPEG and 1.5 mg PLGA-PEG-folate. The uptake was inhibited by adding 2 mM folic acid to the cell culture medium. In all NP formulations, 0.3 mg PLGA-Alexa488 was blended. The incubation time was 6 hours.

DETAILED DESCRIPTION

Figure 1:
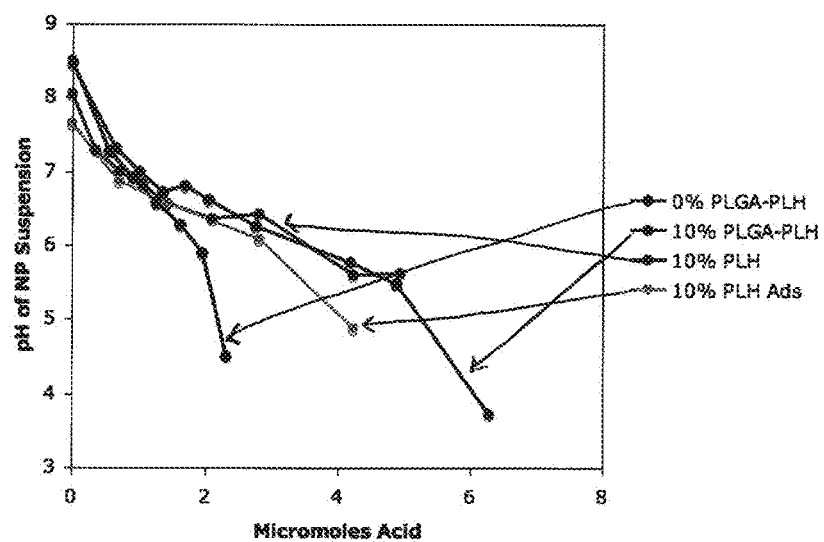
FIG. 1 shows an acid titration plot demonstrating the buffering capacity of various particle formulations, in accordance with one embodiment of the invention.

Compositions of particles that can deliver agents to cells or tissues are provided herein as are methods of using the compositions. Also provided are polymers that can form such particles. Specifically, the particles and polymers can respond to changes in pH and/or redox changes. In some embodiments, the particle is pH responsive and can escape the endosome. For example, in some embodiments, where the particle has a hydrophilic component, the hydrophilic component is shed in the endosome and the rest of the particle escapes the endosome. In some embodiments, the particle exhibits enhanced endosomal escape.

Enhanced endosomal escape can be measured relative to a like particle without the buffering component. As used herein, a "like particle without the buffering component" comprises the same components as the particle that contains the buffering component except for the buffering component. For example, when the particle is made up of the components, polyhistidine, PLGA and PEG, the like particle has PLGA and PEG but not the polyhistidine. In other embodiments, the endosomal escape can be measured relative to a like particle with a different amount of the buffering component. For example, when the particle is made up of the components, polyhistidine, PLGA and PEG, the like particle has PLGA and PEG and a different amount of polyhistidine. Endosomal escape can be measured by methods known to those of ordinary skill in the art or as otherwise described herein.

In further embodiments, the particle is pH responsive, can escape the endosome (or exhibit enhanced endosomal escape) and exhibits reduced toxicity. In still further embodiments, the particle can deliver one or more agents to and/or into a cell. The one or more agents, for example, can be one or more pharmaceutical agents. As used herein, a "pharmaceutical agent" is any agent that may provide some benefit to a subject when administered to the subject. Pharmaceutical agents, therefore, include therapeutic agents, such as drugs, as well as placebo agents. A particle provided herein, or one or more of the polymers of a particle provided, can in some embodiments encapsulate one or more pharmaceutical agents efficiently but can also appropriately release (e.g., in a controlled manner) one or more of the pharmaceutical agents in the cell or other desired location (e.g., at the site of a tumor). In some embodiments, the particle or one or more of the polymers of a particle can also be designed to have an accelerated drug release rate in certain environments (e.g., in a cell or at the site of a tumor).

The present invention, therefore, generally relates to particles and polymers that include a buffering component as described herein. The particles provided can be organic or inorganic. The particles provided can also be a combination of organic or inorganic materials.

The particles provided can be, for example, lipid-based. As used herein, "lipid-based particle" refers to a particle made up of one or more lipids, such as lipidoids. Such particles include liposomes, particles that comprise a lipid monolayer or bilayer, lipoplexes, lipid-based micelles, etc. In some embodiments, such particles are made up primarily of lipids (i.e., the core structure of the particle is the result of one or more lipids although other components may be present).

The particles provided can be, for example, polymer-based. As used herein, "polymer-based particle" refers to a particle that comprises one or more polymers. Such particles include particles with a polymeric core, particles that are composed of a polymeric matrix, polymeric micelles, polyplexes, etc. In some embodiments, such particles are composed primarily of polymers (i.e., the core structure of the particle is the result of one or more polymers although other components may be present).

The particles provided can also be, for example, lipid-polymer-based. A "lipid-polymer-based particle" is one made up of both lipids and polymers. The lipids and polymers may be conjugated to or complexed to each other. The lipids and polymers may also encapsulate each other. In some embodiments, such particles include those where a lipid layer surrounds a polymeric core.

The particles provided can also be, for example, those with a non-polymeric core (e.g., metal particles, quantum dots, ceramic particles, bone particles, viral particles, etc.). Such particles can be surrounded by a lipid layer (e.g., lipid bilayer, lipid monolayer, etc.) or by polymers or a combination thereof in some embodiments.

The components provided herein can be contained in and/or on the particle as separate molecules from the molecules that form the structure of the particle (e.g., the lipids, polymers, etc.). In some embodiments, the one or more components are separate from the molecules of which the particle is primarily composed. The components provided herein, however, may be conjugated to, contained within or are part of the molecules that form the structure of the particle. In some embodiments, the one or more components are conjugated to one or more of the lipids and/or polymers of the particle. In other embodiments, the one or more components are contained within or are part of one or more polymers of the particle.

The present invention also generally related to particles and polymers that comprise two or more components that impart useful properties, such as one or more or all of the properties discussed herein (or any combination thereof). The particles provided herein can also, in some embodiments, target a particular cell or tissue. Such targeting can be an innate property of the particle or it can be provided by specific targeting moieties added to the particle or the components of which the particle is comprised.

As mentioned above, the particles provided can be both pH and redox sensitive. These properties can be useful in settings where it is helpful to increase the drug release rate or to change the physicochemical properties of particles to improve drug delivery. Incorporation of a buffering component, such as polyhistidine, can enhance the encapsulation of agents, such as hydrophilic agents. The amount of such a component can also be varied to optimize the interplay between encapsulation and charge reversal. When the particles also comprise a biodegradable component, such as PLGA, the ratio of the degradable component to the buffering component can be also tuned to optimize the particle, as the degradable component can also play a role in encapsulation. The particles can also comprise a cleavable bond component, and in some embodiments, a hydrophilic component. Depending on the position of such a cleavable bond component, different release of the agent can be achieved. Therefore, the particles provided herein provide a way to optimize drug delivery for many different scenarios. Any of the aforementioned components or combinations thereof can be incorporated into the particle by their inclusion in one or more polymers of the particle in some embodiments.

Particles that respond to pH can be made by including chemical groups whose pKa lies within a physiologically relevant range, for example, between 3 and 9 or between 4 and 8. In other embodiments, the chemical group has a pKa that lies between 5 and 7.6 or between 5.5 and 7.5. As an example, such chemical groups can be part of polymers that make up the particles. These polymers may be incorporated into a drug formulation in such a way that the polymer is adsorbed onto, chemically grafted to or encapsulated into particles formed using these or, in some embodiments, other materials, such as other polymers. Preferably, the polymers are tightly associated with the particles. Under these conditions, at pH values below the pKa, the particle (or polymer) can be preferentially in a protonated state. This scenario can result in buffering of whatever medium in which the particles are suspended in a range that is close to the pKa of the chemical group (e.g., as a polymer side chain). It can also result in a change in the physicochemical characteristics of the particles or the polymers that, in some embodiments, make up the particle.

For example, if a particle were to comprise a polymer or other molecule that becomes positively charged at a pH below its pKa, the particles can become more positively charged (or less negatively charged), which can be desirable from a drug or delivery perspective, as the strength of the interaction of the particle with a cell membrane can be increased. As another example, if at a pH below the pKa, the particles transition from being hydrophobic to being hydrophilic, which can lead to improved drug delivery by enhancing the rate of drug release. In addition, buffering of subcellular compartments can result in improved cytosolic delivery, which can improve the activity of drugs that are active in the cytoplasm but cannot penetrate the plasma membrane.

In some embodiments, a hydrophilic component, such as polyethylene glycol, can also be present in the particles in a way that the hydrophilic component can detach in certain tissues or cellular environments. The hydrophilic component can maintain colloidal stability under physiological conditions. The hydrophilic component can also prevent immune evasion and increase particle circulation time. However, after the particle reaches the target, a hydrophilic component surrounding the particle could, in some embodiments, hamper drug release. Additionally, a hydrophilic layer surrounding the particle could also result in a larger particle size, which, in some embodiments, can hinder drug diffusion in some tissues or cellular environments. Therefore, in some embodiments, the particles provided herein comprise a hydrophilic component attached via a cleavable bond component. In some instances, the cleavable bond component is cleaved when the particle reaches a tumor or enters a cell. This detachment can be beneficial, in some embodiments, for any of the following reasons: (1) with a buffering component (e.g., PLH) in the particle core, after the detachment, the exposed cation segments can trigger a strong association to cells, which can increase the cellular uptake of the particles (the particles that remain without the detached hydrophilic component(s)); (2) the detachment can result in the interaction between the exposed cation segments and the cell compartment membrane (e.g., an endosomal or lysozomal membrane); (3) detachment can result in smoother release of the drug from the particle core. As a specific non-limiting example provided herein, the hydrophilic component (e.g., PEG) is grafted onto a particle through a cleavable bond component (e.g., a disulfide bond).

The particles provided herein can have or are comprised of components that have or confer to the particle any or all (or any combination) of the above-recited functionalities. In some embodiments, the components are contained within one or more polymers. As used herein, "a component" is meant to refer to a single unit or more than one unit (e.g., block or polymer). In some embodiments, the components allow the particles to have a zeta potential difference (i.e., the difference between two zeta potentials, or in other words, the difference between the zeta potential measured at one pH and the zeta potential measured at a different pH) at physiological pH (pH 7.4) relative to at an endosomal pH (pH 4-6.5) that is at least 5 mV. The zeta potential of a particle can be measured in water or PBS. An example of such an assay is provided below in the Examples. In some embodiments, the zeta potential is determined by a method provided in the Examples. Other assays for measuring zeta potential are known to those of ordinary skill in the art. As used herein "zeta potential" refers to a measurement of surface potential of a particle.

In some embodiments, the particles have a zeta potential difference at a pH in the range of 7-8 relative to a pH in the range of 4-6.5 that is at least 5 mV. In other embodiments, the particles have a zeta potential difference at a pH of 7, 7.1, 7.2, 7.3, 7.4, 7.5, 7.6, 7.7, 7.8, 7.9 or 8 relative to at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 that is at least 5 mV.

In any of the embodiments provided herein, the zeta potential difference can also be at least 10 mV, 15 mV, 20 mV, 25 mV, 30 mV, 35 mV, 40 mV, 45 mV, 50 mV, 55 mV, 60 mV, 65 mV, 70 mV, 75 mV, 80 mV, 85 mV, 90 mV, 95 mV or 100 mV or more.

In some embodiments, the zeta potential of the particles is more positive (less negative) at an endosomal pH than at physiological pH. In some embodiments, the zeta potential of the particle is more positive (less negative) at a pH in the range of 4-6.5 than at a pH in the range of 7-8. In other embodiments, the zeta potential of the particle is more positive (less negative) at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 than at a pH of 7, 7.1, 7.2, 7.3, 7.4, 7.5, 7.6, 7.7, 7.8, 7.9 or 8. In some embodiments, the zeta potential is more positive (less negative) by at least 5 mV, 10 mV, 15 mV, 20 mV, 25 mV, 30 mV, 35 mV, 40 mV, 45 mV, 50 mV, 55 mV, 60 mV, 65 mV, 70 mV, 75 mV, 80 mV, 85 mV, 90 mV, 95 mV or 100 mV or more.

In some embodiments, the particle has a zeta potential of −5 mV to 5 mV in the bloodstream or at physiological pH but a zeta potential of 5.1 mV to 100 mV in an endosome or at an endosomal pH or at the site of a tumor. In other embodiments, the particle has a charge of −100 mV to −5.1 mV in the bloodstream or at physiological pH but a zeta potential of 5.1 mV to 100 mV in an endosome or at endosomal pH or at the site of a tumor. In any of these embodiments, the zeta potential difference of the particle in the bloodstream or at physiological pH relative to in an endosome or at an endosomal pH or at the site of a tumor is, preferably, at least 5 mV. The zeta potential difference can also be at least 10 mV, 15 mV, 20 mV, 25 mV, 30 mV, 35 mV, 40 mV, 45 mV, 50 mV, 55 mV, 60 mV, 65 mV, 70 mV, 75 mV, 80 mV, 85 mV, 90 mV, 95 mV or 100 mV or more, in some embodiments.

In some embodiments, the particle (or polymer is some embodiments) is neutral or negatively charged in the bloodstream or at physiological pH but is positively charged in an endosome or at endosomal pH or at the site of a tumor. In other embodiments, the particle (or polymer is some embodiments) is more protonated (or more positively charged or less negatively charged) in an endosome or at endosomal pH or at the site of a tumor than at physiological pH. In some embodiments, the particle (or polymer is some embodiments) is more protonated (or more positively charged or less negatively charged) at a pH in the range of 4-6.5 than at a pH in the range of 7-8. In other embodiments, the particle (or polymer is some embodiments) is more protonated (or more positively charged or less negatively charged) at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 than at a pH of 7, 7.1, 7.2, 7.3, 7.4, 7.5, 7.6, 7.7, 7.8, 7.9 or 8.

In some embodiments, the net charge of a particle or polymer is determined in water or PBS. Methods of determining the net charge of a particle or polymer are known in the art.

The particles and polymers provided herein have been found to be particularly effective when used for delivery. The particles and polymers have been found to efficiently encapsulate an agent (e.g., siRNA) and/or provide increased drug loading. In some embodiments, the particle (or polymer is some embodiments) exhibits an encapsulation efficiency (i.e., the ratio of encapsulated agent to total amount of the agent available for encapsulation) of at least 10%, 15%, 20%, 25%, 30%, 35%, 40%, 45%, 50%, 55%, 60%, 65%, 70%, 75%, 80%, 85%, 90%, 95%, 97%, 99% or more. In some embodiments, the total amount of agent for encapsulation is that amount added to a double emulsion or some precipitation or solvent evaporation step. In some embodiments, the encapsulation efficiency is determined by a method provided in the Examples. In other embodiments, the particles exhibit 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45 or 50% or more drug loading (i.e., the percentage of total particle weight that is the encapsulated agent). In some embodiments, the drug loading is determined by a method provided in the Examples. In still other embodiments, the particles provided herein exhibit a level of encapsulation efficiency of at least 10%, 15%, 20%, 25%, 30%, 35%, 40%, 45%, 50%, 55%, 60%, 65%, 70%, 75%, 80%, 85%, 90%, 95%, 97%, 99% or more and 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45 or 50% or more drug loading.

A "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In one embodiment, the polymer has at least 2 repeat units. In other embodiments, the polymer has at least 4 repeat units, at least 7 repeat units, at least 12 repeat units, at least 17 repeat units, at least 44 repeat units, or at least 100 repeat units.

If more than one type of repeat unit is present within the polymer, then the polymer is said to be a "copolymer." It is to be understood that in any embodiment employing a polymer, the polymer being employed can be a copolymer in some cases. The repeat units forming the copolymer may be arranged in any fashion. For example, the repeat units may be arranged in a random order, in an alternating order, or as a "block" copolymer, i.e., comprising one or more regions each comprising a first repeat unit (e.g., a first block) and one or more regions each comprising a second repeat unit (e.g., a second block), etc. Block copolymers may have two (a diblock copolymer), three (a triblock copolymer) or more numbers of distinct blocks.

It should be understood that, although the terms "first," "second," etc. may be used herein to describe various elements, including polymeric components, these terms should not be construed as being limiting (e.g., describing a particular order or number of elements), but rather, as being merely descriptive, i.e., labels that distinguish one element from another. Thus, for example, although one embodiment of the invention may be described as having a "first" element present and a "second" element present, other embodiments of the invention may have a "first" element present but no "second" element present, a "second" element present but no "first" element present, two (or more) "first" elements present, and/or two (or more) "second" elements present, etc., and/or additional elements such as a "first" element, a "second" element, and a "third" element, without departing from the scope of the present invention.

Various embodiments of the present invention are directed to polymeric conjugates. As used herein, a "polymeric conjugate" describes two or more polymers (such as those described herein) that have been associated with each other usually by covalent bonding of the two or more polymers together or via a covalently bonded linker. Thus, a polymeric conjugate may comprise a first polymer and a second polymer, which have been conjugated together to form a block copolymer where the first polymer is a first block of the block copolymer and the second polymer is a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, a particle or polymer comprises two or more components selected from the group consisting of a buffering component, a degradable component and a hydrophilic component. The particles and polymers provided herein can further comprise a cleavable bond component. These components can be conjugated to each other (e.g., as part of a polymer conjugate with each contained in a separate portion (as a block) of the polymer conjugate).

A particle can be formed with such polymer conjugates in some embodiments. For example, a first polymer can be prepared that lacks one or more of the components and a second polymer comprising one or more components lacking in the first polymer may be blended with the first polymer to create a particle comprising all four components. Polymers that can be used to form particles in this manner are also referred to herein as "blending polymers". For example, the first polymer can be a conjugate of a buffering component and a degradable component, and the second polymer can be a conjugate of a degradable component and a hydrophilic component. Particles formed from such polymers are also provided herein.

As another non-limiting example, a block copolymer of a degradable component, such as PLGA, and a buffering component, such as PLH, can be synthesized to form PLGA-block-PLH. Once dissolved into an organic solution, such as DMSO, the PLGA-block-PLH can be mixed with other polymers that impart other desirable characteristics to the resulting particle. For example, the other polymer with a degradable component and a hydrophilic component polymer, such as PLGA-block-PEG. The resulting particles can, in some embodiments, exhibit enhanced particle stability, reduced clearance by immune cells and have improved pharmacokinetics in the body.

The ratio of a first polymer to a second polymer, third polymer, fourth polymer, etc. may be varied until a combination having the desired properties is obtained. It should be understood that additional combinations and/or polymers may be used to combine the components in a composition. It should also be understood that one or more of the above components may be excluded.

As used herein, a buffering component can control the net charge of the particle (or polymer is some embodiments). The buffering component also preferably binds to an agent and, when the agent is, for example, a nucleic acid, can condense the nucleic acid. The buffering component can be a unit or block in a particle or polymer that is capable of being protonated and deprotonated. Such a unit or block will have a pKa associated with a proton that participates in the buffering action. In some cases, the pKa may be less than 8, less than 7, less than 6, etc. In other cases, the pKa may be between 4.5 and 6.5, between 5 and 7, between 5 and 7.6 or between 5.5 and 7.5. Examples of suitable buffering components include components having an amine, an imidazole, a pyridine, an imine, and the like. For example, the component can be one or more amino acids such as histidine, lysine, arginine, etc. The buffering component, therefore, can be polyhistidine, polylysine, polyarginine or copolymers of histidine and lysine, histidine and arginine, and lysine and arginine. Other polymers such as poly(ethylene imine), poly(beta amino esters), and the like can also be used. In some instances, the buffering component is one or more histidine residues within a chain of other amino acid residues. The buffering component can also include non-peptidic polymers in some embodiments.

A degradable component generally provides controlled release functionality to the particle or polymer and is one that degrades preferably within a physiological environment, such as within the body. In general, the degradable component is hydrophobic. The degradable component includes organic molecules, such as a lipid or polymer as provided elsewhere herein. A degradable component can be, for example, a biodegradable polymer. For instance, the polymer can be one that hydrolyzes spontaneously upon exposure to water (e.g., within a subject) and/or degrade upon exposure to heat (e.g., at temperatures of about 37° C.). Degradation of a polymer can occur at varying rates, depending on the polymer or copolymer used. For example, the half-life of the polymer (the time at which 50% of the polymer is degraded into monomers and/or other nonpolymeric moieties) can be on the order of days, weeks, months, or years, depending on the polymer.

The degradable components can be biologically degraded, e.g., by enzymatic activity or cellular machinery, in some cases, for example, through exposure to a lysozyme (e.g., having relatively low pH). In some cases, the degradable components, such as polymers, can be broken down into monomers and/or other nonpolymeric moieties that cells can either reuse or dispose of without significant toxic effect on the cells (for example, polylactide can be hydrolyzed to form lactic acid, polyglycolide may be hydrolyzed to form glycolic acid, etc.).

Examples of biodegradable polymers include, but are not limited to, poly(lactic acid), derivatives of poly(lactic acid), poly(lactic-co-glycolic acid), derivatives of poly(lactic-co-glycolic acid), polyanhydrides, poly(ortho esters), derivatives of poly(ortho esters), poly(caprolactones), derivatives of poly(caprolactone), poly(ethylene imine), derivatives of poly(ethylene imine), poly(acrylic acid), derivatives of poly(acrylic acid), poly(urethane), derivatives of poly(urethane), and combinations thereof.

As used herein, a hydrophilic component can be a component that is able to control properties such as immunogenicity, interaction with cellular components, drug release rate, and the like. Such components include polymers, such as, a poly(alkylene glycol) or poly(alkylene oxide), such as poly(propylene glycol), or poly(ethylene oxide), poly(ethylene glycol), having the formula —$(CH_2-CH_2-O)_n$—, where n is any positive integer or modified versions thereof. The poly(ethylene glycol) can be present within a polymeric conjugate in any suitable form. For instance, a polymeric conjugate may be a block copolymer where one of the blocks is poly(ethylene glycol). A polymeric conjugate containing poly(ethylene glycol) repeat units is also referred to as a "PEGylated" polymer. Such polymers can control inflammation and/or immunogenicity (i.e., the ability to provoke an immune response, due to the presence of the poly(ethylene glycol) groups.

PEGylation can also be used, in some cases, to decrease charge interaction, for example between a polymer and a biological moiety, e.g., by creating a hydrophilic layer on the surface of the polymer, which may shield the polymer from interacting with the biological moiety. In some cases, the addition of poly(ethylene glycol) repeat units may increase plasma half-life of the conjugate, for instance, by decreasing the uptake of the conjugate by the phagocytic system while decreasing transfection/uptake efficiency by cells. Those of ordinary skill in the art will know of methods and techniques for PEGylation, for example, by using EDC (1-ethyl-3-(3-dimethylaminopropyl)carbodiimide hydrochloride) and NHS (N-hydroxysuccinimide) to react a polymer to a PEG group terminating in an amine, as discussed in the examples below, by ring opening polymerization techniques (ROMP), or the like.

In some embodiments, a particle or polymer has a cleavable bond component. "A cleavable bond component", as used herein can be a cleavable bond itself or a component that comprises a cleavable bond. Examples of cleavable bond components include those that are pH active, redox-active or enzymatically active. As used herein, "pH active" refers to a cleavable bond component that can be cleaved at a certain pH. "Redox-active" refers to a cleavable bond component that can be cleaved under oxidizing or reducing conditions. "Enzymatically active" refers to a cleavable bond component that can be cleaved by an enzyme.

Examples of pH active cleavable bond components include diorthoester, orthoester, vinylether, phosphoramidate, hydrazone, beta-thiopropionate, and low pKa polyplex. Examples of redox-active cleavable bond components include disulfide and redox-sensitive chimeric polypeptide linkers (e.g., alpha-helical linkers with redox sensitive motifs, alpha-helices with embedded adjacent or dispersed vicinal cysteine residues). Redox sensitive motifs can be found in the thioredoxin family of oxidoreductases. Examples of enzymatically active cleavable bonds include peptide bonds that can be cleaved by a protease. Other examples of cleavable bond components are known to those of ordinary skill in the art.

In some embodiments, a disulfide can be formed by reacting two thiol groups together in an oxidation reaction. In some embodiments, a disulfide can be added by modification with a protected disulfide such as an orthopyridyl disulfide (OPSS) group. For example, a polymer can be reacted with 3-(2-pyridyldithio)proprionic acid hydrazide HCl (PDPH) to yield a polymer with an attached OPSS group. The protected disulfide can then be reacted with a thiol group on another polymer to create a conjugate of the two polymers.

In some instances, a cleavable bond component can be used to form a chemical bond between two species. For example, a block copolymer can be formed by reacting two polymers such that a cleavable bond component bonds the two polymers together. In some embodiments, a redox-active cleavable bond component can be cleaved under reducing conditions, such as those found in cellular environments (i.e., inside an endosome).

The particles and polymers, for example, can include a buffering component and a degradable component. The particles and polymers, as another example, can include a buffering component, a degradable component and a hydrophilic component. In some embodiments, the degradable component and/or the hydrophilic component is conjugated to the buffering component via a cleavable bond component. Therefore, in some embodiments, the hydrophilic component is detachable in a reducing environment (e.g., in the endosome). As described in more detail elsewhere herein, the hydrophilic component can provide stability to particles and be released in an appropriate environment (e.g., in the endosome) to change the properties of the remaining portion of the particles advantageously (e.g., to expose a positively charged core and allow for increased drug release).

In the above embodiments, the ratio of biodegradable component to buffering component (by weight) can be 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:60, 1:70, 1:80, 1:90 or 1:100. In other embodiments, the ratio of biodegradable component to buffering component (by weight) is 100:1, 90:1, 80:1, 70:1, 60:1, 50:1, 45:1, 40:1, 35:1, 30:1, 25:1, 20:1, 15:1, 10:1, 9:1, 8:1, 7:1, 6:1, 5:1, 4:1, 3:1, 2:1 or 1:1. In some embodiments, the ratio is 5:1. In other embodiments, the polymer comprises 1-200 buffering component units and 5-1000 biodegradable component units. In some embodiments, poly(lactide-co-glycolide) is the degradable component. In some embodiments, a polymer comprises the poly (lactide-co-glycolide) (e.g., 5 kD to 50 kD). In other embodiments, polyethylene glycol is the hydrophilic component. In some embodiments, a polymer comprises polyethylene glycol (e.g., 3-5 kD).

In some embodiments, a polymer as provided herein is amphiphilic, i.e., having a hydrophilic portion and a hydrophobic portion, or a relatively hydrophilic portion and a relatively hydrophobic portion. A hydrophilic polymer is one generally that attracts water and a hydrophobic polymer is one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers can be measured relative to each other, i.e., a first polymer can be more hydrophilic than a second polymer. For instance, the first polymer can have a smaller contact angle than the second polymer.

Certain embodiments of the invention are directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer containing carboxylic acid groups can be conjugated with poly(ethylene glycol) repeat units to form a poly(ester-ether). In other embodiments, copolymers may contain poly(ester-amide)s, e.g., polymers having repeat units joining by ester bonds (e.g., R—C(O)—)—R' bonds) and amide bonds (e.g., R—C(O)—NH—R' bonds). For example, a polypeptide (e.g., poly(histidine)) can be joined with a polyester (e.g., PLGA). Various combinations of these bonds will be known to those skilled in the art. For example, copolymers can contain poly(amide-ether)s, e.g., polymers having repeat units joined by amide bonds and ether bonds.

In some cases, particles and polymers can be modified with a linker that provides an additional functional group. For example, poly(histidine) can be conjugated to a cysteine residue to introduce thiol functional group. Various other modifications, including a targeting moiety, an imaging moiety, a chelating moiety, a moiety having multiple charge groups, a neutral moiety, a therapeutic moiety, etc. can be conjugated to the polymer and are discussed in more detail below.

Particles comprising such moieties are, therefore, also provided. In some embodiments, however, the particles have encapsulated therein or complexed thereto a targeting moiety, an imaging moiety, a chelating moiety, a moiety having multiple charge groups, a neutral moiety or a therapeutic moiety, etc. In some of these embodiments, the encapsulated or complexed moiety are not comprised within a polymer.

A targeting moiety, as used herein, is a moiety able to bind to or otherwise associate with a biological entity, for example, a membrane component, a cell surface receptor, tumor antigen (e.g., prostate specific membrane antigen), or the like. The term "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has a specificity (as measured via a disassociation constant) of less than about 1 micromolar, at least about 10 micromolar, or at least about 100 micromolar.

Non-limiting examples of biological moieties that can be included in the particles or polymers provided include a peptide, polypeptide, a protein, glycoprotein, an enzyme, a nucleic acid, polynucleotide, a fatty acid, a hormone, an antibody, a carbohydrate, a peptidoglycan, a glycopeptide, or the like. In some cases, the biological moiety can be relatively large, for example, for peptides, nucleic acids, or the like. For example, the biological moiety can have a molecular weight of at least about 1,000 Da, at least about 2,500 Da, at least about 3000 Da, at least about 4000 Da, or at least about 5,000 Da, etc. Relatively large targeting moieties may be useful, in some cases, for differentiating between cells. For instance, in some cases, smaller targeting moieties (e.g., less than about 1000 Da) may not have adequate specificity for certain applications, such as targeting applications. In contrast, larger molecular weight targeting moieties can offer a much higher targeting affinity and/or specificity. For example, a targeting moiety can offer smaller dissociation constants, e.g., tighter binding. However, in other embodiments, the targeting moiety can be relatively small, for example, having a molecular weight of less than about 1,000 Da or less than about 500 Da.

In one embodiment, the targeting moiety includes a protein or a peptide. "Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids and can, in some embodiments, be a polypeptide. The use of "protein" is not intended to require, but does not exclude, full-length protein. A protein can be, for example, a protein drug, an antibody, an antibody fragment, a recombinant antibody, a recombinant protein, an enzyme, or the like. In some cases, one or more of the amino acids of the protein or peptide can be modified in some instances, for example, by the addition of a chemical entity such as a carbohydrate group, a phosphate group, a farnesyl group, an isofarnesyl group, a fatty acid group, a linker for conjugation, functionalization, or other modification, etc.

Other examples of peptides or proteins include, but are not limited to, ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor alpha, transforming growth factor beta, interferon (IFN), and hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, lymphocyte function-associated antigen, intercellular adhesion molecule, vascular cell adhesion molecule, Thy-1, antiporters, CA-15-3 antigen, fibronectins, laminin, myelin-associated glycoprotein, GAP, GAP-43.

As used herein, an "antibody" refers to a protein or glycoprotein consisting of one or more polypeptides encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases.

The term "antigen-binding fragment" of an antibody as used herein, refers to one or more portions of an antibody that retain the ability to specifically bind to an antigen. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). Furthermore, although the two domains of the Fv fragment, V and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883).

Non-limiting examples of antibodies and other suitable targeting moieties include those that target tumor/cancer-associated antigens, antigens that are differentially expressed on inflamed tissue (e.g., EGFR, ICAM-1 VCAM-1), antigens that are differentially expressed during cell maturation or antigens that are expressed on diseased tissues, pathogens or bacteria (e.g., sugar moieties).

Tumor-antigens include Melan-A/MART-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, and c-erbB-2.

As other examples, the targeting moieties include peptides that comprise Arg-Gly-Asp motifs (or RGD peptides) that target integrin present on angiogenic tumor vasculature.

In another embodiment, the targeting moiety includes a nucleic acid. The term "nucleic acids," or "oligonucleotides," as used herein, refers to a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide may be, for example, ribose sugars (a "ribonucleic acid," or "RNA"), or deoxyribose sugars (a "deoxyribonucleic acid," or "DNA"). In some cases, the polymer may comprise both ribose and deoxyribose sugars. Examples of bases include, but not limited to, the naturally-occurring bases (e.g., adenosine or "A," thymidine or "T," guanosine or "G," cytidine or "C," or uridine or "U"). In some cases, the polymer may also comprise nucleoside analogs (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitropyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynyl-cytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate moieties (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. In some cases, the polynucleotide may include DNA, RNA, modified DNA, modified RNA, antisense oligonucleotides, expression plasmid systems, nucleotides, modified nucleotides, nucleosides, modified nucleosides, aptamers, intact genes, or combinations thereof. Other examples of polynucleotides include interfering RNA, natural or unnatural siRNAs, shRNAs, microRNAs, ribozymes, DNA plasmids, aptamers, antisense oligonucleotides, randomized oligonucleotides, or ribozymes. The targeting moiety can also be an Adnectin™ (a biologic derived from fibronectin).

Other nucleic acid targeting moieties include Spiegelmers® (mirror-image oligonucleotides that can bind to a target molecule), SMIP™ therapeutics (single chain polypeptides comprising one binding domain, one hinge domain and one effector domain) or SCORPION™ therapeutics (single chain polypeptides that is multi-specific and/or multivalent).

As a specific non-limiting example, the targeting moiety can include an aptamer, i.e., a nucleic acid able to specifically bind a specific target molecule, such as a biological moiety. Non-limiting examples of aptamers include RNA aptamers and DNA aptamers. For example, the size of the aptamer may be at least about 5 kDa, at least about 10 kDa, at least about 15 kDa, or at least about 20 kDa. A non-limiting example of a particular aptamer is the PSMA aptamer described below in the Examples. The PSMA aptamer can have the sequence GGGAGGACGAUGCG-GAUCAGCCAUGUUUACGUCACUCCUUGUCAAUC-CUCAUC GGC (SEQ ID NO: 1).

Surprisingly, it was discovered in an aspect of the invention that substantial uptake of untargeted particles can occur. Data demonstrating this are provided in FIGS. 16-20 and are described further in the Examples. Therefore, the particles and polymers provided herein, do not in some embodiments comprise a targeting moiety.

An "imaging moiety", as used herein, refers to a moiety that can be determined in some fashion, either directly or indirectly. For instance, the imaging entity may be fluorescent, radioactive, electron-dense, a member of a binding pair, a substrate for an enzymatic reaction, an antigen for an antibody, etc. In some cases, the imaging entity itself is not directly determined, but instead interacts with a second entity in order to effect determination; for example, coupling of the second entity to the imaging entity may result in a determinable signal. Non-limiting examples of imaging moieties includes fluorescent compounds such as FITC or a FITC derivative, fluorescein, GFP, etc; a radioactive atom, for example, $^{3}H$, $^{14}C$, $^{33}P$, $^{32}P$, $^{125}I$, $^{131}I$, $^{35}S$, etc.; or a heavy metal species, for example, gold or osmium. As a specific example, an imaging moiety may be a gold nanoparticle.

As used herein, a "chelating moiety" is a moiety that can bind one or more ions, typically divalent (or higher) ions such as $Ca^{2+}$, $Mg^{2+}$, or $Fe^{2\pm}$. An example of such a moiety is ethylenediamine tetraacetic acid.

In some cases, a particle or polymer is part of a controlled release system. A controlled release system, as used herein, is a particle or polymer combined with an agent or other payload, such as a drug, a therapeutic agent, a diagnostic agent, a prognostic agent, a prophylactic agent, etc., and the agent is released from the controlled release system in a predesigned or controlled manner. For example, the agent can be released in a constant manner over a predetermined period of time, the agent can be released in a cyclic manner over a predetermined period of time, or an environmental condition or external event can trigger the release of the agent. Preferably, in some embodiments the agent is released in an acidic (low pH) environment (e.g., in an endosome or at endosomal pH or at the site of a tumor). The controlled release particle or polymer system can include a component that is biocompatible, and in some cases, biodegradable.

In some embodiments, particles are formed from the polymers provided herein using methods known to those skilled in the art or as described in more detail below in the Examples.

In certain embodiments, the components or polymers that comprise them can affect the interactions of a particle with a biological system. For example, a particle can be substantially neutral or negatively charged outside of a cell, which can provide stability to the particle and impart reduced toxicity. In some instances, particles having a neutral or negative charge have a longer circulation lifetime in the bloodstream than particles with a positive charge.

A particle can be internalized into a cell by several mechanisms known to those skilled in the art. Without wishing to be bound by any theory, a particle can be internalized by endocytosis and contained within an endosome. As known to those in the art, an endosome is a membrane bound vesicle having an aqueous core. The core can be acidified, leading to a decrease in pH, and can also facilitate reduction reactions by maintaining a reducing environment. In some embodiments, therefore, a particle can become positively (or less negatively) charged inside a cell (e.g., within an endosome) or at the site of a tumor. For example, a particle having a buffering component may buffer the core of an endosome by sequestering protons entering the endosome. Without wishing to be bound by any theory, the buffering action of a particle within an endosome can lead to osmotic swelling of the endosome and subsequent rupturing of the endosome. In some cases, such mechanisms can be advantageous. For example, if the particle is carrying a pharmaceutically active payload, rupture of the endosome can facilitate delivery of the pharmaceutically active payload within the cell. Preferably, the particles provided herein become positively charged (or less negatively charged) inside a cell. In some embodiments, therefore, altering the sign and magnitude of the charge of a particle can be advantageous for drug delivery. For example, a particle can be hydrophobic between pH 7 and pH 8, but can be hydrophilic between pH 4 and pH 6.5. In certain instances, a particle can acquire a positive charge (or less negative charge) between pH 4 and pH 6.5 that increases the hydrophilicity of the particle and facilitates drug release from the particle.

In some cases, the buffering capacity of the particle can improve delivery of an agent by reducing the degradation of the agent in the cell. For instance, the ability of a particle to buffer an endosome and thus reduce the decrease in pH in the endosome can result in a pH environment that is more benign for a particular agent.

In certain instances, the charge character of a particle (or polymer) is reversible. For example, a particle (or polymer) can acquire a charge (i.e., a positive charge or less negative charge) in an endosome or at endosomal pH or at the site of a tumor as the pH decreases that facilitates disruption of the endosome membrane thereby releasing the particle (or polymer) into the cytosol. In the higher pH environment of the cytosol, the particle (or polymer) can then revert to having less positive (more negative) charge character thereby preventing further disruption of the cell. Particles and polymers exhibiting these features are provided. The particles and polymers can have a buffering component and a degradable component. In some embodiments, these particles and polymers also have a cleavable bond component and a hydrophilic component. The hydrophilic component can be bound to the buffering component via the cleavable bond component. In this embodiment, the cleavable bond component is cleaved in an endosome or at an endosomal pH or at the site of a tumor such that the hydrophilic component is detached from the particle. The remaining particle (comprising the buffering component and degradable component) can then escape the endosome. Particles and polymers with the features or that confer these features are also provided.

In some embodiments, therefore, a portion of a particle can be detached under cleavable conditions (e.g., at a certain pH, under oxidizing conditions, under reducing conditions, or in the presence of an enzyme). For example, when the conditions are redox conditions, an endosome can have a reducing environment sufficient for cleaving reducible bonds. Such functionality can be advantageous for drug delivery. For instance, a particle can have a detachable hydrophilic component, the detachment of which facilitates drug release. Detachment can also expose a buffering component of the particle to the cell, which can lead to increased interactions as described above. Sufficient redox conditions can also exist extracellularly, for example within tumor tissue. In such instances, cleavage of a reducible bond can decrease the size of a particle thereby allowing the particle to penetrate the cell, tissue or subcellular compartment more easily.

In some cases, a particle (or polymer) having a neutral or negative charge (or more negative or less positive charge) can have a first association strength with a biological entity and upon acquiring a positive charge (or more positive or less negative charge) can have a second association strength with a biological entity, the second association strength being greater than the first association strength. For example, the strength of interaction with the cell membrane can be increased by increasing the positive charge character of the particle (or polymer).

A conjugate of the present invention can be formed using any suitable conjugation technique. For instance, conjugation can be performed using techniques such as EDC-NHS chemistry (1-ethyl-3-(3-dimethylaminopropyl)carbodiimide hydrochloride and N-hydroxysuccinimide) or a reaction involving a maleimide or a carboxylic acid, which can be conjugated to one end of a thiol, an amine, or a similarly functionalized polyether. The conjugation, for instance, the conjugation of a poly(ester) and a poly(ether) to form a poly(ester-ether), can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer or other moiety that comprises a carboxylic acid functional group (e.g., a poly(ester-ether) compound) with a polymer or other moiety (such as a targeting moiety) comprising an amine. For instance, a targeting moiety, such as an aptamer, can be reacted with an amine to form an amine-containing moiety, which can then be conjugated to the carboxylic acid of a polymer or other moiety. Such a reaction may occur as a single-step reaction, i.e., the conjugation is performed without using intermediates such as N-hydroxysuccinimide or a maleimide. The conjugation reaction between the amine-containing moiety and the carboxylic acid-terminated polymer (such as a poly(ester-ether) compound) or other moiety can be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethysulfoxide, to a solution containing the carboxylic acid-terminated polymer or other moiety. The carboxylic acid-terminated polymer or other moiety may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer or other moiety may occur spontaneously, in some cases. Unconjugated macromers can be washed away after such reactions, and the polymer or other moiety may be precipitated in solvents such as, for instance, ethyl ether, hexane, methanol, or ethanol.

As a specific example, a nuclease-stable oligonucleotide, for instance, a prostate specific membrane antigen (PSMA) aptamer, can be prepared as a targeting moiety in a particle as follows. Carboxylic acid modified poly(lactide-co-glycolide) (PLGA-COOH) can be conjugated to an amine-modified heterobifunctional poly(ethylene glycol) ($NH_2$-PEG-COOH) to form a copolymer of PLGA-PEG-COOH. By using an amine-modified PSMA aptamer ($NH_2$-Apt), a triblock polymer of PLGA-PEG-Apt can be formed by conjugating the carboxylic acid end of the PEG to the amine functional group on the aptamer. The multiblock polymer can then be used, for instance, as discussed herein, e.g., for therapeutic, imaging, and/or diagnostic applications. For example, the PSMA aptamer may become localized to PSMA on surface of prostate cancer cells or present on endothelial cells of the neovasculature of other solid tumors.

Those of ordinary skill in the art will be able to identify targeting moieties specific to a target of interest.

The particles can comprise any of the components or polymers containing one or more of the components as described herein. The particles can have a substantially spherical (i.e., the particles generally appear to be spherical) or non-spherical configuration. For instance, the particles, upon swelling or shrinkage, can adopt a non-spherical configuration. In some cases, the particles can include polymeric blends. By controlling the ratio of a first and second polymer in the final polymer, the concentration and location of a component in the final polymer may be readily controlled to any suitable degree. Thus, in certain embodiments, a library of such particles may be created.

In some cases, the particle is a microparticle, nanoparticle (NP) or picoparticle. As used herein, a "nanoparticle" is a particle has a characteristic dimension of less than about 1 micrometer, where the characteristic dimension of a particle is the diameter of a perfect sphere having the same volume as the particle. For example, the particle may have a characteristic dimension that is less than 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm or 20 nm. In some embodiments, the particle has a characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm. In other embodiments, the particle has a characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm.

In some cases, a population of particles may be present, and the population of particles has an average characteristic dimension as described above. A population of particles can include at least 20 particles, at least 50 particles, at least 100 particles, at least 300 particles, at least 1,000 particles, at least 3,000 particles, or at least 10,000 particles. Various embodiments of the present invention are directed to such populations of particles. For instance, in some embodiments, the particles can each be substantially the same shape and/or size ("monodisperse"). For example, the particles can have a distribution of characteristic dimensions such that no more than about 5% or about 10% of the particles have a characteristic dimension greater than about 10% greater than the average characteristic dimension of the particles, and in some cases, such that no more than about 8%, about 5%, about 3%, about 1%, about 0.3%, about 0.1%, about 0.03%, or about 0.01% have a characteristic dimension greater than about 10% greater than the average characteristic dimension of the particles. In some cases, no more than about 5% of the particles have a characteristic dimension greater than about 5%, about 3%, about 1%, about 0.3%, about 0.1%, about 0.03%, or about 0.01% greater than the average characteristic dimension of the particles.

In one set of embodiments, the particles can have an interior and a surface, where the surface has a composition different from the interior, i.e., there can be at least one compound present in the interior but not present on the surface (or vice versa), and/or at least one compound is present in the interior and on the surface at differing concentrations. For example, in one embodiment, a compound, such as a targeting moiety (e.g., an aptamer), can be present in both the interior and the surface of the particle, but at a higher concentration on the surface than in the interior of the particle, although in some cases, the concentration in the interior of the particle can be essentially nonzero, i.e., there is a detectable amount of the compound present in the interior of the particle.

In some cases, the interior of the particle is more hydrophobic than the surface of the particle. For instance, the interior of the particle can be relatively hydrophobic with respect to the surface of the particle, and an agent or other payload can be hydrophobic, and readily associates with the relatively hydrophobic center of the particle. In other cases, the interior of the particle is positively charged, and an agent or other payload can be negatively charged or hydrophilic. The agent or other payload may thus be contained within the interior of the particle, which may thus shelter it from the external environment surrounding the particle (or vice versa). For instance, an agent or other payload contained within a particle administered to a subject can be protected from a subject's body, and the body can also be isolated from the drug. A targeting moiety present on the surface of the particle may allow the particle to become localized at a particular targeting site, for instance, a tumor, a disease site, a tissue, an organ, a type of cell, etc. The agent or other payload may then, in some cases, be released from the particle and allowed to interact locally with the particular targeting site.

Another aspect of the present invention is directed to a "payload," or an agent (or more than one agent) contained within a particle, such as those described herein. The agent or other payload can be hydrophilic, hydrophobic or negatively charged. Surprisingly, it has been found that both a hydrophilic agent and a hydrophobic agent can be co-delivered with the compositions provided herein. Therefore, in some embodiments the payload comprises both a hydrophilic agent and a hydrophobic agent. The particles provided here can, in some embodiments, target or become localized at specific portions within a subject, and the payload can be delivered to those portions. The targeting can be an innate function of the particle (i.e., without the addition of a specific targeting moiety) or it can be the result of a targeting moiety that is present in the particle. The particles, for example, can become localized to a tumor, a disease site, a tissue, an organ, a type of cell, etc. within the body of a subject. In some embodiments, the targeting depends on the nature of the particle itself or it depends on the targeting moiety added to the particle.

The subject can be a human or non-human animal Examples of subjects include, but are not limited to, a mammal such as a dog, a cat, a horse, a donkey, a rabbit, a cow, a pig, a sheep, a goat, a rat, a mouse, a guinea pig, a hamster, a primate, or the like.

The subject can be any subject in need of administration of an agent as provided herein. In some embodiments, the subject has cancer, an infectious disease, and inflammatory disease, a cardiovascular disease or neurological disease.

Examples of cancer include, but are not limited to, biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; nasopharyngeal cancer; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

Examples of inflammatory disease includes, but are not limited to, Alzheimer's, arthritis, asthma, atherosclerosis, Crohn's disease, colitis, dermatitis, diverticulitis, hepatitis, irritable bowel syndrome (IBS), lupus erythematous, nephritis, Parkinson's and ulcerative colitis.

Examples of infectious disease include, but are not limited to, viral infectious diseases, such as AIDS, Chickenpox (Varicella), Common cold, Cytomegalovirus Infection, Colorado tick fever, Dengue fever, Ebola hemorrhagic fever, Hand, foot and mouth disease, Hepatitis, Herpes simplex, Herpes zoster, HPV, Influenza (Flu), Lassa fever, Measles, Marburg hemorrhagic fever, Infectious mononucleosis, Mumps, Norovirus, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease and Yellow fever; bacterial infectious diseases, such as Anthrax, Bacterial Meningitis, Botulism, Brucellosis, Campylobacteriosis, Cat Scratch Disease, Cholera, Diphtheria, Epidemic Typhus, Gonorrhea, Impetigo, Legionellosis, Leprosy (Hansen's Disease), Leptospirosis, Listeriosis, Lyme disease, Melioidosis, Rheumatic Fever, MRSA infection, Nocardiosis, Pertussis (Whooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus and Urinary Tract Infections; parasitic infectious diseases, such as African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trichomoniasis and Trypanosomiasis; fungal infectious disease, such as Aspergillosis, Blastomycosis, Candidiasis, Coccidioidomycosis, Cryptococcosis, Histoplasmosis, Tinea pedis (Athlete's Foot) and Tinea cruris; prion infectious diseases, such as Alpers' disease, Fatal Familial Insomnia, Gerstmann-Sträussler-Scheinker syndrome, Kuru and Variant Creutzfeldt-Jakob disease.

Examples of cardiovascular disease include, but are not limited to, cardiac hypertrophy, myocardial infarction, stroke, arteriosclerosis, and heart failure.

Examples of neurological disease include, but are not limited to, headache disorders such as migraine, cluster headache and tension headache; epilepsy and seizure disorders; neurodegenerative disorders, including Alzheimer's disease, Parkinson's disease, Lou Gehrig's disease and ataxia; cerebrovascular diseases such as transient ischemic attacks (TIA) and cerebrovascular accidents (CVA) also known as strokes or brain attack which is either ischemic or hemorrhagic in nature; sleep disorders (insomnia); cerebral palsy (CP), a non-progressive disorder of voluntary and posture control; CNS infections such as encephalitis, meningitis and peripheral neuritis; brain abscess; herpetic meningoencephalitis, aspergilloma and cerebral hydatic cyst; PNS infections, such as tetanus and botulism; neoplasms such as glioblastoma multiforme, spinal cord tumors, peripheral nerves tumor (acoustic neuroma); movement disorders such as Parkinson's disease, chorea, hemiballismus, tic disorder, and Gilles de la Tourette syndrome; CNS demyelinating disease such as multiple sclerosis, and of the peripheral nervous system, such as Guillain-Barre syndrome (GBS) and chronic inflammatory demyelinating polyneuropathy (CIDP); spinal cord disorders e.g., tumors, infections, trauma, malformations such as myelocele, meningomyelocele, myelomeningocele; peripheral nerve disorders like Bell palsy (CN VII) and carpal tunnel syndrome (CTS) involving the median nerve, myopathy and neuromuscular junctions problem (e.g., myasthenia gravis); traumatic injuries to the brain, spinal cord and peripheral nerves; altered mental status, encephalopathy, stupor and coma; and speech and language disorders (expressive or receptive aphasia).

In one set of embodiments, the payload is an agent or a combination of more than one agent. In some embodiments, the agent is a hydrophobic drug or hydrophilic drug. In other embodiments, the agent is negatively charged. Particles may be useful, for example, to direct a particle containing a drug to a particular localized location within a subject, e.g., to allow localized delivery of the drug to occur. Examples of payloads include, but are not limited to, nucleic acids, oligonucleotides, proteins, glycoproteins, polypeptides, peptides, carbohydrates or small molecules (e.g., having a molecular weight of less than about 1000 Da). Nucleic acids include DNA or RNA. Examples of which are antisense oligonucleotides, aptamers and RNAi (e.g., siRNAs, shRNAs, microRNAs (miRNAs)). Examples of proteins, include enzymes and antibodies.

As used herein, a "siRNA molecule" is a double stranded RNA molecule (dsRNA) consisting of a sense and an antisense strand, which are complementary (Tuschl, T. et al., 1999, Genes & Dev., 13:3191-3197; Elbashir, S. M. et al., 2001, EMBO J., 20:6877-6888). As used herein, a "shRNA molecule" is a sequence of RNA that makes a tight hairpin turn, and a "miRNA molecule" is a single-stranded RNA molecule of about 21-23 nucleotides in length.

In some embodiments the nucleic acid (e.g., siRNA) targets a JC virus gene, MLL-AF4, PCSK9, a respiratory virus (e.g., RSV, PIV) gene, Nav1.8, ApoB, an anti-apoptotic gene, a Huntingtin gene, AML-1/MTG8 fusion, Factor V Leiden, MYC, Factor VII, a gene from Ebola, BCR-ABL fusion, CCR5, or an influenza virus gene.

In other embodiments the nucleic acid (e.g., siRNA) targets a protein tyrosine phosphatase (PTP-1B) gene or a MAP kinase gene, such as ERK1, ERK2, JNK1, JNK2, p38; an MDR, Myc, Myb, c-Myc, N-Myc, L-Myc, c-Myb, a-Myb, b-Myb, v-Myb, cyclin D1, Cyclin D2, cyclin E, CDK4, cdc25A, CDK2, or CDK4 gene; a G72 or DAAO gene; a gene of the telomerase pathway, such as a TERT or TR/TERC; an interleukin gene, such as IL-1, IL-2, IL-5, IL-8, IL-10, IL-15, IL-16, IL-17, or IL-18; an interleukin receptor gene, or a chromosomal translocation, such as BCR-ABL, TEL-AML-1, EWS-FLI1, EWS-ERG, TLS-FUS, PAX3-FKHR, or AML-ETO; a GRB2 associated binding protein; a growth factor or growth factor receptor, such as a TGFbeta or TGFbeta Receptor; PDGF or PDGFR; VEGF or VEGFr1, VEGFr2, or VEGFr3; or IGF-1R, DAF-2, or 1nR; PRL1, PRL2, PRL3, protein kinase C (PKC), PKC receptor, MDR1, TERT, TR/TERC, cyclin D1, NF-KappaB, REL-A, REL-B, PCNA, CHK-1, c-fos, jun, or BCL-2; a viral gene, for example, such as a hepatitis viral gene (e.g., a gene of an HAV, HBV, or HCV); a reporter gene, such as GFP or beta galatosidase and the like; any gene in any one of a number of cell lines including, but not limited to, a 3T3, DLD2, THP1, Raw264.7, IC21, P388D1, U937, HL60, SEM-K2, WEHI-231, HB56, TIB55, Jurkat, J45.01, K562, EL4, LRMB, Bcl-1, BC-3, TF1, CTLL-2, C1R, Rath, VERO, MRCS, CV1, Cos 7, RPTE, A10, T24, J82, A549, A375, ARH-77, Calu1, SW480, SW620, SKOV3, SK-UT, CaCo2, A375, C8161, CCRF-CEM, MCF-7, MDA-MB-231, MOLT, mIMCD-3, NHDF, HeLa, HeLa-S3, Huh1, Huh4, Huh7, HUVEC, HASMC, HEKn, HEKa, MiaPaCell, Panel, PC-3, LNCaP, HepG2, or U87 cell line.

In still other embodiments, the nucleic acid (e.g., siRNA) is used to silence genes in a/an fibroblast cell, epithelial cell, mesodermal cell, neural cell, keratinocyte, lymphoma cell, leukemia cell, mast cell, adherent tumor cell line.

In yet other embodiments, the nucleic acid (e.g., siRNA) targets an exogenous gene of a genetically modified cell. An exogenous gene can be, for example, a viral or bacterial gene from an organism that has invaded or infected the cell, or the exogenous gene can be any gene introduced into the cell by natural or artificial means, such as by a genetic recombination event.

The particles or polymer provided can include one or more of the agents provided herein. The one or more agents can be one or more pharmaceutical agents (e.g., one or more drugs).

Non-limiting examples of potentially suitable drugs include antimicrobial agents, analgesics, antinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable medicaments may be selected from contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics;

xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Specific non-limiting examples of drugs include doxorubicin, mitomycin, cisplatin, daunorubicin, bleomycin, actinomycin D, neocarzinostatin, carboplatin, stratoplatin, Ara-C. Other examples include Capoten, Monopril, Pravachol, Avapro, Plavix, Cefzil, Duricef/Ultracef, Azactam, Videx, Zerit, Maxipime, VePesid, Paraplatin, Platinol, Taxol, UFT, Buspar, Serzone, Stadol NS, Estrace, Glucophage (Bristol-Myers Squibb); Ceclor, Lorabid, Dynabac, Prozac, Darvon, Permax, Zyprexa, Humalog, Axid, Gemzar, Evista (Eli Lily); Vasotec/Vaseretic, Mevacor, Zocor, Prinivil/Prinizide, Plendil, Cozaar/Hyzaar, Pepcid, Prilosec, Primaxin, Noroxin, Recombivax HB, Varivax, Timoptic/XE, Trusopt, Proscar, Fosamax, Sinemet, Crixivan, Propecia, Vioxx, Singulair, Maxalt, Ivermectin (Merck & Co.); Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer); Vantin, Rescriptor, Vistide, Genotropin, Micronase/Glyn./Glyb., Fragmin, Total Medrol, Xanax/alprazolam, Sermion, Halcion/triazolam, Freedox, Dostinex, Edronax, Mirapex, Pharmorubicin, Adriamycin, Camptosar, Remisar, Depo-Provera, Caverject, Detrusitol, Estring, Healon, Xalatan, Rogaine (Pharmacia & Upjohn); Lopid, Accrupil, Dilantin, Cognex, Neurontin, Loestrin, Dilzem, Fempatch, Estrostep, Rezulin, Lipitor, Omnicef, FemHRT, Suramin, or Clinafloxacin (Warner Lambert).

The drug can be an anti-cancer drug such as 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cisporphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, siRNA, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

The drug can be an anti-infective such as Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); or Ciprofloxacin (Cipro).

The drug can be an anti-inflammatory agent such as Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin or Zomepirac Sodium.

The drug can be one for treating cardiovascular disease. Such drugs include anti-thrombotic and/or fibrinolytic agents, such as plasminogen; Streptokinase; Urokinase: Anisoylated Plasminogen-Streptokinase Activator Complex; Pro-Urokinase; (Pro-UK); rTPA (alteplase or activase; "r" denotes recombinant); rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; Retaplase; Trifenagrel; Warfarin; and Dextrans. Such drugs also include anti-platelet agents such as Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; and Anagrelide. Such drugs also include lipid reducing agents such as gemfibrozil, cholystyramine, colestipol, nicotinic acid, probucol lovastatin, fluvastatin, simvastatin, atorvastatin, pravastatin, and cirivastatin. Such drugs include direct thrombin inhibitors such as hirudin, hirugen, hirulog, agatroban, PPACK, and thrombin aptamers. Such drugs also include calcium channel blockers such as dihydropyridines, such as nifedipine, the phenyl alkyl amines, such as verapamil, and the benzothiazepines, such as diltiazem. Other calcium channel blockers include amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin. Such drugs also include beta-adrenergic receptor blocking agents such as atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropyl-methoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyethiazol, 7-(2-hydroxy-3-t-butylaminpropoxy)phthalide. Such drugs also include anticoagulant agents such as Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bivalirudin; Bromindione; Dalteparin Sodium; Desirudin; Dicumarol; Heparin Calcium; Heparin Sodium; Lyapolate Sodium; Nafamostat Mesylate; Phenprocoumon; Tinzaparin Sodium; and Warfarin Sodium.

The drug can be one for treating a neurological disease. Such drugs include, but are not limited to, Diazepam, Valium, Clonazepam, Methamphetamine, Adderall, Neurontin, K-Dur, Gabapentin, Klonopin, Methylphenidate, Provigil, Ritalin, Lamictal, Modafinil, Abilify, Aripiprazole, Azmacort, Concerta, Depakote, Dilantin, Divalproex sodium, Klor-Con, Lamotrigine, Lithium, Natalizumab, Phenergan, Phenytoin, Prednisone, Promethazine, Risperdal, Risperidone, Temazepam, Topamax, Topiramate, Triamcinolone, Tysabri and Verapamil.

Further specific non-limiting examples of drugs that can be included within a particle of the present invention include acebutolol, acetaminophen, acetohydoxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, betha nechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, 6× chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfiram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecainide, fluphenazine, fluprednisolone, flurazepam, folic acid, furosemide, gemfibrozil, glipizide, glyburide, glycopyrrolate, gold compounds, griseofiwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenytoin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulos, methyidopa, methylergonovine, methylphenidate, methylprednisolone, methysergide, metoclopramide, matolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystafin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin-v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenytoin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, syllium, pyridostigmine, pyridoxine, pyrilamine, pyrvinium, quinestrol, quinethazone, uinidine, quinine, ranitidine, rauwolfia alkaloids, riboflavin, rifampin, ritodrine, alicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocainide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B12, vitamin C, vitamin D, vitamin E, vitamin K, xanthine, and the like.

In another set of embodiments, the payload is a diagnostic agent. For example, the payload may be a fluorescent molecule; a gas; a metal; a commercially available imaging agents used in positron emissions tomography (PET), computer assisted tomography (CAT), single photon emission computerized tomography, x-ray, fluoroscopy, and magnetic resonance imaging (MRI); or a contrast agents. Non-limiting examples of suitable materials for use as contrast agents in MRI include gadolinium chelates, as well as iron, magnesium, manganese, copper, and chromium. Examples of materials useful for CAT and x-ray imaging include, but are not limited to, iodine-based materials.

As another example, the payload may include a radionuclide, e.g., for use as a therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming use with various embodiments of the present invention include, but are not limited to, $^{123}$I, $^{125}$I, $^{130}$I, $^{131}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{14}$C, $^{13}$N, $^{15}$O, $^{32}$P, $^{33}$P, or $^{18}$F.

The agents provided herein can be present in the particle. In some embodiments, the agent is conjugated to the particle or to one or more of the polymers of the particle (generally via a covalent bond or via a covalently bonded linker). In other embodiments, the agent is complexed to the particle or to one or more of the polymers of the particle (generally by a charge or electrostatic and/or hydrophobic interaction). In further embodiments, the agent is encapsulated within the particle or by one or more of the polymers of the particle (generally by being trapped by one or more of the polymers during particle formation).

Another aspect of the invention is directed to systems and methods of making particles. Such systems and methods include nanoprecipitation, single and double emulsion, and salting out. Examples of methods for forming the particles provided herein are also described below in the Examples.

In one set of embodiments, the particles can be formed by double emulsion. For example, polymers and/or other hydrophobic agents are dissolved in organic (oil) phase. Hydrophilic agents, such as siRNAs, are dissolved in water phase. Emulsions are formed in which an emulsion (water/oil or oil/water) is dispersed in a continuous phase (water or oil, respectively) to produce water/oil/water or oil/water/oil.

In another set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles, such as nanoparticles.

Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethylsulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles, such as nanoparticles, may be formed as the first solution contacts the immiscible second liquid, e.g., precipitation of the polymer upon contact causes the polymer to form nanoparticles while the first solution poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

In further aspects, a method comprising contacting one or more cells with a particle or composition comprising a particle is provided. In some embodiments, the method further comprises determining the level of delivery of an agent. In some embodiments, the determining the level of delivery is determining the level of transfection efficiency and/or the level of gene silencing. Such methods are described in detail below in the Examples. In some embodiments, the level of transfection efficiency and/or gene silencing is determined by a method provided in the Examples. In other embodiments, determining the level of delivery comprises determining the amount of an agent in a cell or cells after contact with the particle or composition comprising the particle.

In some aspects, a method comprising producing a particle or polymer with a buffering component and a degradable component and determining the charge of the particle or polymer at a pH in the range of pH 3-pH 9 is provided. In some embodiments, the pH is 4, 4.5, 5, 5.5, 6, 6.5, 7, 7.5, 8, 8.5 or 9.

In some embodiments, the pH is physiological pH. In some embodiments, the pH is in the range of 7-8. In other embodiments, the pH is 7, 7.1, 7.2, 7.3, 7.4, 7.5, 7.6, 7.7, 7.8, 7.9 or 8. In other embodiments, the pH is an endosomal pH or the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5.

In some embodiments, the charge of the polymer is determined at another pH in the range of pH 3-pH 9. In some embodiments, the pH is 4, 4.5, 5, 5.5, 6, 6.5, 7, 7.5, 8, 8.5 or 9. In some embodiments, the other pH is an endosomal pH or the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5. In other embodiments, the other pH is physiological pH. In some embodiments, the pH is in the range of 7-8. In other embodiments, the pH is 7, 7.1, 7.2, 7.3, 7.4, 7.5, 7.6, 7.7, 7.8, 7.9 or 8.

In any of the above embodiments, the method can further comprise selecting a particle or polymer that is more positive (or less negative) at an endosomal pH or the pH at the site of a tumor than at physiological pH. In some embodiments, the method comprises selecting a particle or polymer that is more positive (or less negative) at a pH in the range of 4-6.5 than in the range of 7-8. In other embodiments, the method comprises selecting a particle or polymer that is more positive (or less negative) at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 than 7, 7.1, 7.2, 7.3, 7.4, 7.5, 7.6, 7.7, 7.8, 7.9 or 8.

In some embodiments, the particle or polymer further comprises a hydrophilic component and/or a cleavable bond component.

In some embodiments, the particle or polymer has an agent conjugated thereto. In other embodiments, an agent is encapsulated within the particle or by the polymer. In further embodiments, the particle or polymer is complexed to an agent.

In further aspects a method comprising producing a particle with a buffering component and a degradable component, and determining the zeta potential of the particle at a pH in the range of pH 3-pH 9 is provided. In some embodiments, the pH is 4, 4.5, 5, 5.5, 6, 6.5, 7, 7.5, 8, 8.5 or 9. In some embodiments the zeta potential of the particle is measured in water or PBS.

In some embodiments, the pH is physiological pH. In some embodiments, the pH is in the range of 7-8. In other embodiments, the pH is 7, 7.1, 7.2, 7.3, 7.4, 7.5, 7.6, 7.7, 7.8, 7.9 or 8. In other embodiments, the pH is an endosomal pH or the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5.

In some embodiments, the zeta potential of the particle is determined at another pH in the range of pH 3-pH 9. In some embodiments, the pH is 4, 4.5, 5, 5.5, 6, 6.5, 7, 7.5, 8, 8.5 or 9. In some embodiments, the other pH is an endosomal pH or the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5. In other embodiments, the other pH is physiological pH. In some embodiments, the pH is in the range of 7-8. In other embodiments, the pH is 7, 7.1, 7.2, 7.3, 7.4, 7.5, 7.6, 7.7, 7.8, 7.9 or 8.

In any of the above embodiments, the method can further comprise selecting a particle that has a more positive (or less negative) zeta potential at an endosomal pH or the pH at the site of a tumor than at physiological pH. In some embodiments, the method comprises selecting a particle that has a more positive (or less negative) zeta potential at a pH in the range of 4-6.5 than in the range of 7-8. In other embodiments, the method comprises selecting a particle that has a more positive (or less negative) zeta potential at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 than 7, 7.1, 7.2, 7.3, 7.4, 7.5, 7.6, 7.7, 7.8, 7.9 or 8.

In some embodiments, the particle that is selected is more positive (or less negative) by at least 5 mV, 10 mV, 15 mV, 20 mV, 25 mV, 30 mV, 35 mV, 40 mV, 45 mV, 50 mV, 55 mV, 60 mV, 65 mV, 70 mV, 75 mV, 80 mV, 85 mV, 90 mV, 95 mV, 100 mV or more.

In other embodiments, where the zeta potential is determined at two different pHs, the method can further comprise selecting a particle with a zeta potential difference of at least 5 mV, 10 mV, 15 mV, 20 mV, 25 mV, 30 mV, 35 mV, 40 mV, 45 mV, 50 mV, 55 mV, 60 mV, 65 mV, 70 mV, 75 mV, 80 mV, 85 mV, 90 mV, 95 mV, 100 mV or more. In some embodiments, the zeta potential is measured at an endosomal pH or the pH at the site of a tumor and at physiological pH. In other embodiments, the zeta potential is measured at a pH in the range of 4-6.5 and at a pH in the range of 7-8. In further embodiments, the pH is measured at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 and at a pH of 7, 7.1, 7.2, 7.3, 7.4, 7.5, 7.6, 7.7, 7.8, 7.9 or 8. In these embodiments, the zeta potential difference is the difference between the two zeta potentials that are measured.

In some embodiments, the particle or polymer further comprises a hydrophilic component and/or a cleavable bond component.

In some embodiments, the particle or polymer further comprises an agent.

The particles (or polymers) can be combined with pharmaceutically acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc. In some embodiments, the administration is oral, parenteral, nasal, intravenous, transdermal, intraarterial, intraarticular, subcutaneous, intramuscular, rectal or vaginal administration.

As used herein, the term "pharmaceutically acceptable carrier" means a non-toxic, inert solid, semi-solid or liquid filler, diluent, encapsulating material or formulation auxiliary of any type. Remington's Pharmaceutical Sciences Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. If filtration or other terminal sterilization methods are not feasible, the formulations can be manufactured under aseptic conditions.

The compositions provided herein can be formulated for in vivo administration to a subject. In some embodiments, the compositions are sterile.

The pharmaceutical compositions of this invention can be administered to a patient by any means known in the art. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive composition is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be suppositories which can be prepared by mixing the inventive composition with suitable non-irritating excipients or carriers such as cocoa butter, polyethylene glycol, or a suppository wax which are solid at ambient temperature but liquid at body temperature and therefore melt in the rectum or vaginal cavity and release the inventive composition.

Dosage forms for topical or transdermal administration of an inventive pharmaceutical composition include ointments, pastes, creams, lotions, gels, powders, solutions, sprays, inhalants, or patches. The inventive composition can be admixed under sterile conditions with a pharmaceutically acceptable carrier and any needed preservatives or buffers as may be required. Ophthalmic formulations, ear drops, and eye drops are also contemplated as being within the scope of this invention. The ointments, pastes, creams, and gels may contain, in addition to the inventive compositions of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof. Transdermal patches have the added advantage of providing controlled delivery of a compound to the body. Such dosage forms can be made by dissolving or dispensing the inventive compositions in a proper medium. Absorption enhancers can also be used to increase the flux of the compound across the skin. The rate can be controlled by either providing a rate controlling membrane or by dispersing the inventive compositions in a polymer matrix or gel.

Powders and sprays can contain, in addition to the inventive compositions of this invention, excipients such as lactose, talc, silicic acid, aluminum hydroxide, calcium silicates, and polyamide powder, or mixtures thereof. Sprays can additionally contain customary propellants such as chlorofluorohydrocarbons.

When administered orally, the inventive compositions can be, but are not necessarily, encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer J. Control. Release 5:13, 1987; Mathiowitz et al. Reactive Polymers 6:275, 1987; Mathiowitz et al. J. Appl. Polymer Sci. 35:755, 1988; Langer Acc. Chem. Res. 33:94, 2000; Langer J. Control. Release 62:7, 1999; Uhrich et al. Chem. Rev. 99:3181, 1999; Zhou et al. J. Control. Release 75:27, 2001; and Hanes et al. Pharm. Biotechnol. 6:389, 1995). The inventive compositions may be encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides.

Pharmaceutical compositions for oral administration can be liquid or solid. Liquid dosage forms suitable for oral administration of inventive compositions include pharmaceutically acceptable emulsions, microemulsions, solutions, suspensions, syrups, and elixirs. In addition to an encapsulated or unencapsulated composition, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants, wetting agents, emulsifying and suspending agents, sweetening, flavoring, and perfuming agents.

Solid dosage forms for oral administration include capsules, tablets, pills, powders, and granules. In such solid dosage forms, the encapsulated or unencapsulated composition is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

It will be appreciated that the exact dosage of the composition is chosen by the individual physician in view of the patient to be treated. In general, dosage and administration are adjusted to provide an effective amount of the composition to the patient being treated. As used herein, the "effective amount" of a composition refers to the amount necessary to elicit the desired biological response. As will be appreciated by those of ordinary skill in this art, the effective amount of a composition may vary depending on such factors as the desired biological endpoint, the drug to be delivered, the target tissue, the route of administration, etc. For example, the effective amount of the composition containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The compositions of the invention may be formulated in dosage unit form for ease of administration and uniformity of dosage. The expression "dosage unit form" as used herein refers to a physically discrete unit of composition appropriate for the patient to be treated. It will be understood, however, that the total daily usage of the compositions of the present invention will be decided by the attending physician within the scope of sound medical judgment. For any composition, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of composition can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

The present invention also provides any of the above-mentioned compositions in kits, optionally with instructions for administering any of the compositions described herein by any suitable technique as previously described, for example, orally, intravenously, pump or implantable delivery device, or via another known route of drug delivery. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, but can also include the composition of the invention and instructions of any form that are provided in connection with the composition in a manner such that a clinical professional will clearly recognize that the instructions are to be associated with the specific composition. In some embodiments, the kits can contain one or more of the polymers provided herein with instructions for mixing (e.g., to produce a particle as provided herein). In other embodiments, the kits can contain one or more of the components provided herein with other reagents and instructions for producing a particle or polymer as provided herein. In some embodiments, the kits further contain an agent.

The kits described herein may also contain one or more containers, which may contain an inventive composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

The invention also involves, in another aspect, promotion of the administration of any of the compositions described herein. In some embodiments, one or more compositions of the invention are promoted for the prevention or treatment of various diseases such as those described herein via administration of any one of the compositions of the present invention. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

In another aspect, a composition comprising a particle that comprises a cleavable bond component and a fluorescence resonance energy transfer (FRET) pair is provided. In some embodiments, the donor of the FRET pair is Oregon Green-488 (OG-488), Alexa 488, Alexa 546, BODIPY 493, Oyster 556, Fluor (FAM), Cy3 or TMR (TAMRA) and the acceptor of the FRET pair is Dabcyl, Cy5, Alexa 594, Alexa 647 or Oyster 656. In other embodiments, the donor is OG488 and the acceptor is Dabcyl. Generally, the cleavable bond component is present between the two molecules of the FRET pair. In some embodiments, the cleavable bond component is pH active, enzymatically active or redox-active. Such component can, therefore, be cleaved under certain pH, redox or enzymatic conditions. The composition can also comprise a moiety that conjugated to the cleavable bond component such that when the cleavable bond component is cleaved under certain conditions, the moiety is separated from the rest of the particle. An example of such a moiety is PEG, and such particles are described below in more detail in the Examples. The particles, therefore, can comprise the molecule of Formula 1.

The particles can be any of the particles provided herein. For example the particles can be lipid-based, polymer-based or a combination of the two. The particles can also be a microparticle, nanoparticle or picoparticle. The particles can also be organic or inorganic. In still other embodiments, the particle is a liposome, polymeric micelle, lipoplex or polyplex. In some embodiments, the particle comprises one or more lipids. In some embodiments, the one or more lipids are lipidoids. In other embodiments, the particle further comprises one or more polymers. In still other embodiments, one or more of the lipids are conjugated to one or more of the polymers. In some embodiments, the particle comprises one or more polymers. In some embodiments, one or more of the lipids or polymers are degradable.

In other embodiments, the one or more polymers comprise a polyester, poly(ortho ester), poly(ethylene imine), poly(caprolactone), polyanhydride, poly(acrylic acid), polyglycolide or poly(urethane). In still other embodiments, the one or more polymers comprise poly(lactic acid) (PLA) or poly(lactic-co-glycolic acid) (PLGA). In some embodiments, the one or more polymers comprise polyalkylene glycol or a polyalkylene oxide. In some embodiments, the polyalkylene glycol is polyethylene glycol (PEG) or the polyalkylene oxide is polyethylene oxide (PEO).

In FRET, the "donor fluorescent moiety" and the "acceptor fluorescent moiety" are selected so that the donor and acceptor moieties exhibit FRET when the donor moiety is excited. One factor to be considered in choosing the donor/acceptor fluorescent moiety pair is the efficiency of FRET between the two moieties. In some embodiments, the efficiency of FRET between the donor and acceptor moieties is at least 10%, in some embodiments, at least 50%, and in other embodiments, at least 80%. The efficiency of FRET can be tested empirically using the methods described herein and known in the art.

FRET is the transfer of photonic energy between fluorophores and is a tool for characterizing molecular detail because it allows determination of changes in distance between two ends of the fusion protein reporter. The design of the fusion protein reporter, as described above, incorporates a core covalently attached to a donor fluorescent moiety at one end and an acceptor fluorescent moiety at the core's other end (including quencher pairs as described above). Thus, changes in the conformation of the core result in changes in the distance between the donor and acceptor molecules thereby resulting in alterations in FRET.

The high resolution of FRET has been used in many studies of molecular dynamics and biophysical phenomena. Additional information relating to FRET methods can be found in Forster, T. Ann Physik 2:55-75 (1948). Tables of spectral overlap integrals are also available (for example, Berlman, I. B. Energy transfer parameters of aromatic compounds, Academic Press, New York and London (1973)). FRET is a nondestructive spectroscopic method that can monitor proximity and relative angular orientation of fluorophores in living cells and/or in real time. See, for example, Adams, S. R., et al., Nature 349:694-697 (1991), and Gonzalez, J. & Tsien, R. Y. Biophy. J. 69:1272-1280 (1995).

To undergo FRET, the emission spectrum of the donor overlaps with the excitation spectrum of the acceptor. A laser is tuned to the excitation wavelength of the donor fluorophore. The donor fluorophore emits its characteristic wavelength and with modifications such as acetylation, methylation, and/or phosphorylation of the core, the distance between the donor and acceptor changes. As the acceptor fluorophore moves into interactive proximity with the donor fluorophore, the acceptor fluorophore is excited by the energy from the donor fluorophore. The consequence of this interaction is that the emission of the donor fluorophore may be quenched and that of the acceptor fluorophore may be enhanced.

Once a fluorescence signal is generated it can then be detected and the detected signals from FRET may be analyzed in real time and/or stored in a database for analysis. The particular type of detection means will depend on the type of signal generated. Most of the interactions involved in the method will produce an electromagnetic radiation signal. Many methods are known in the art for detecting electromagnetic radiation signals. Preferred devices for detecting signals are two-dimensional imaging systems that have, among other parameters, low noise, high quantum efficiency, proper pixel-to-image correlation, and efficient processing times. An example of a device useful for detecting signals is a two-dimensional fluorescence imaging system which detects electromagnetic radiation in the fluorescent wavelength range.

There are several categories of fluorescence imaging devices based on the type of fluorescence signal measured, either intensity, lifetime, or spectra. Intensity signals can be captured by a variety of methods including charge coupled device (CCD) camera, streak cameras, and silicon diode arrays. In addition, fluorometers can be used to measure the fluorescence of samples contacted with the fusion protein reporters of the invention. Alternative imaging devices known to those of skill in the art may also be used in the methods of the invention. After the detectable signals are generated and detected the signals can be analyzed.

Various factors may be balanced to optimize the efficiency and detectability of FRET from the fluorescent indicator. The emission spectrum of the donor fluorescent moiety should overlap as much as possible with the excitation spectrum of the acceptor fluorescent moiety to maximize the signal. Also, the quantum yield of the donor fluorescent moiety and the extinction coefficient of the acceptor fluorescent moiety should be as large as possible. In addition, the excitation spectra of the donor and acceptor moieties should overlap as little as possible so that a wavelength region can be found at which the donor moiety can be excited selectively and efficiently without directly exciting the acceptor moiety. In some cases, direct excitation of the acceptor moiety may be avoided because it can be difficult to distinguish direct emission from fluorescence arising from FRET. Similarly, the emission spectra of the donor and acceptor moieties should have minimal overlap so that the two emissions can be distinguished.

The degree of FRET can be determined by any spectral or fluorescence lifetime characteristic of the excited donor moiety. For example, intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor can be monitored.

In some embodiments, changes in the degree of FRET are determined as a function of the change in the ratio of the amount of fluorescence from the donor and acceptor moieties, a process referred to as "ratioing". Changes in the absolute amount of indicator, excitation intensity, and turbidity or other background absorbances in the sample at the excitation wavelength affect the intensities of fluorescence from both the donor and acceptor approximately in parallel.

In another aspect, a composition comprising the molecule of Formula 1 is provided.

In still another aspect, a method of detecting cleavage of the aforementioned particle that comprises a cleavable bond component and a fluorescence resonance energy transfer (FRET) pair is provided. In some embodiments, the method comprises exposing the particle to conditions under which cleavage occurs (as described above and below in the Examples), and detecting or measuring the level of fluorescent emission. The level of fluorescent emission can be detected by fluorescence emission spectroscopy. As mentioned above, the cleavable bond component is pH active, enzymatically active or redox-active. Therefore, cleavage can be detected under certain pH, redox or enzymatic conditions. As the particle can also comprise a moiety conjugated to the cleavable bond component such that when the cleavable bond component is cleaved under certain conditions, the moiety is separated from the rest of the particle, the method can also be used to determine the separate of the moiety from the particle. The moiety can be any the conjugation of which to or separation from the particle is desired. Such moieties include agents, such as pharmaceutical agents, any of the components provided herein (e.g., hydrophilic components), targeting moieties, etc.

The following examples are intended to illustrate certain embodiments of the present invention, but do not exemplify the full scope of the invention.

EXAMPLES

Example 1

Materials and Methods

PLH that contains 20 histidine units and one cysteine unit at the C terminal was synthesized using solid-phase peptide synthesis by Biopolymers Laboratory at MIT's Koch Institute. OPSS-PEG-OCH$_3$ and OPSS-PEG-COOH were purchased from Laysan Bio Inc (Arab, Ala.). The PEG was conjugated to PLH at 1:1 molar ratio in water to form PLH-SS-PEG-COOH. The reaction progress was monitored by UV spectroscopy at 360 nm wavelength of 2-thiopyridinyl leaving group from the OPSS. After the reaction finished, the solution was freeze-dried for 48 hours. PLGA-COOH (purchased from DURECT Corporation, Cupertino, Calif.) was activated using EDC/NHS in dry DMF (both purchased from Sigma-Aldrich, St. Louis, Mo.) to form PLGA-NHS. Activated PLGA-NHS was precipitated using cold methanol (−20° C.) and vacuum dried. Afterwards, it was dissolved in dry DMSO and reacted towards the amine group on PLH-SS-PEG-COOH. The final product was precipitated using cold methanol (−20° C.).

In order to synthesize PLGA-SS-PLH-PEG-OCH$_3$ and PLGA-SS-PLH-PEG-COOH, PLGA-COOH first reacted with PDPH (Pierce Biotechnology Inc., Rockford, Ill.) in dry DMSO with the presence of EDC and NHS at room temperature for 24 hours. The product was precipitated using cold methanol and was then dissolved in dry DMSO. PLH at a molar ratio 1:1 was added. The mixture was stirred at room temperature and monitored by UV spectroscopy at 360 nm wavelength of 2-thiopyridinyl leaving group from the PDPH. After the reaction stopped, SVA-PEG-OCH$_3$ or SVA-PEG-COOH (Laysan Bio Inc.) at 1:1 molar ratio was added and reacted at room temperature for 24 hours. The final product was obtained by precipitating the reaction mixture in cold methanol (−20° C.) and vacuum dried.

Nanoparticle was formed by using double emulsion method. 0.5-2 mg polymer was dissolved in 0.6 mL chloroform. 10 nmol siRNA or DNA was dissolved in 20 uL water and added to the chloroform. The mixture was emulsified by using Misonix Sonicator S-4000 at 40% power for 45 seconds. 2 mL water was added to the emulsion and emulsified at the same power for another 45 seconds. The double emulsion was added to another 8 mL water. The organic phase was evaporated while stirring in a chemical hood for 6 hours.

Nanoparticle was also formed by using nanoprecipitation. 2.5 mg polymer was dissolved in 0.5 mL acetonitrile (Sigma-Aldrich) and then was added drop-wise to 3 mL water while stirring. Acetonitrile in the mixture was evaporated after stirring in a chemical hood for 6 hours.

The RNA aptamer-NH$_2$ was activated by mixing EDC/NHS in water to convert the amine group to NHS. This activation took ~20 minutes. After the activation, the aptamer was added to nanoparticle suspension and reacted at room temperature for 2 hours. Before placed on the cell, the nanoparticle was washed and concentrated using Amicon ultra-4 100K Da centrifuge tube.

Nanoparticle size, size distribution and zeta potential were measured by dynamic light scattering (Brookhaven Instruments Corporation 90 plus particle sizer, 676 nm laser) at 25° C. and at a scattering angle of 90 degree at a concentration of approximately 1 mg NP/mL water. The intensity-weighted mean value was recorded as the average of three measurements.

23-mer DNA (5'-TGGTTTACATGTTCCAATATTTT) conjugated with rhodamine was purchased from Operon Biotechnologies Inc (Huntsville, Ala.). The DNA was encapsulated by double emulsion as described above. A 4-well chamber slide purchased from BD Bio Inc. (San Jose, Calif.) was used for imaging. Cell surface was stained by using anti EGFR-Alexa Fluor 488 purchased from Santa Cruz Biotechnology Inc. (Santa Cruz, Calif.). Cells were fixed using 4% formaldehyde and mounted using Vectashield mounting medium containing DAPI from Vector Laboratories Inc. (Burlingame, Calif.). Florescent microscope images were taken by using Delta Vision Microscope at MIT's Koch Institute with 60× magnification.

For the siRNA transfection experiment, 22RV1 prostate cancer cells were cultured in 96-well plate. Human GAPDH siRNA was purchased from Ambion Inc. (Austin, Tex.) and encapsulated by using double emulsion methods as described above. Transfection efficiency was evaluated at day 2, day 3 and day 4 by using the KDalert GAPDH Assay Kit purchased from Ambion Inc.

Results pH Responsiveness of Particles

FIG. 1 depicts titration curves for suspensions of nanoparticles formed by nanoprecipitation and show the buffering capacity of PLGA-block-PLH nanoparticles. The polymers in FIG. 1 were blended with PLGA-block-PEG (PLGA-PEG) prior to nanoprecipitation, and the 10% indicates that 10% (mol/mol) of the total polymer content was the appropriate polymer, with the other 90% being PLGA-PEG in all instances. Other methods of incorporating PLH are shown as a comparison: encapsulation of PLH (PLH) and adsorbing PLH (PLH Ads).

Figure 2A:
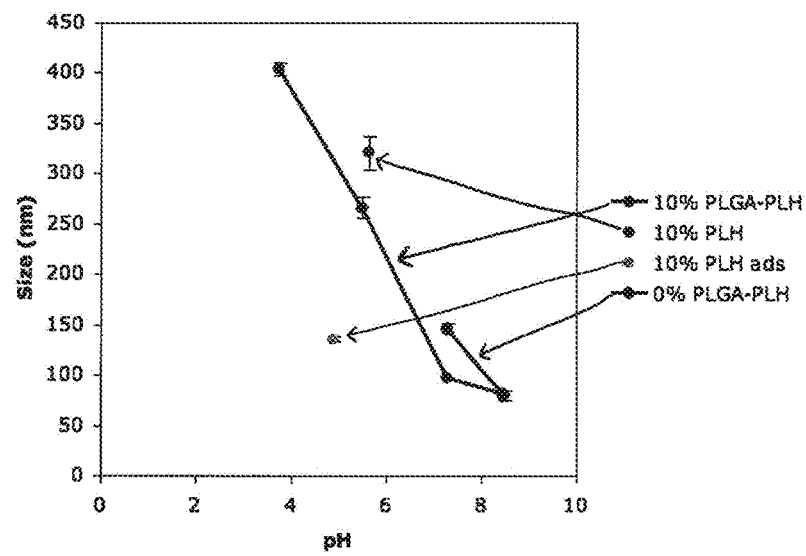
FIG. 2 shows a plot of particle size as a function of pH (A) and a plot of zeta potential varying with pH (B) for various particle formulations, each in accordance with one embodiment of the invention.
Figure 2B:
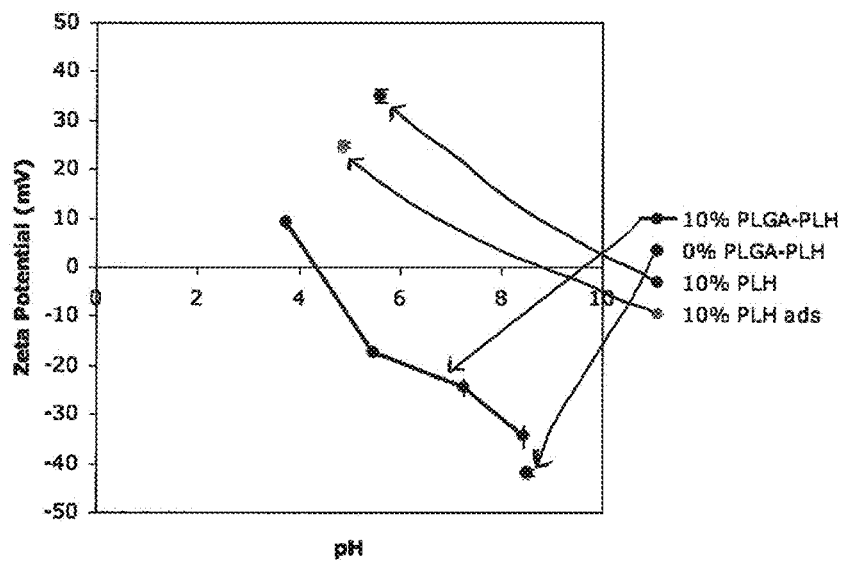

FIG. 2 shows nanoparticle size varying with pH. The pH in which the nanoparticles were suspended was adjusted using 0.047 N HCl dropwise. At each point, the size of the nanoparticles was measured using dynamic light scattering.

As in FIG. 1, the polymers in FIG. 2 were blended with PLGA-block-PEG (PLGA-PEG) prior to nanoprecipitation, and the 10% indicates that 10% (mol/mol) of the total polymer content was the appropriate polymer, with the other 90% being PLGA-PEG in all instances. Other methods of incorporating PLH are again shown as a comparison: encapsulation of PLH (PLH) and adsorbing PLH (PLH Ads).

Figure 3:
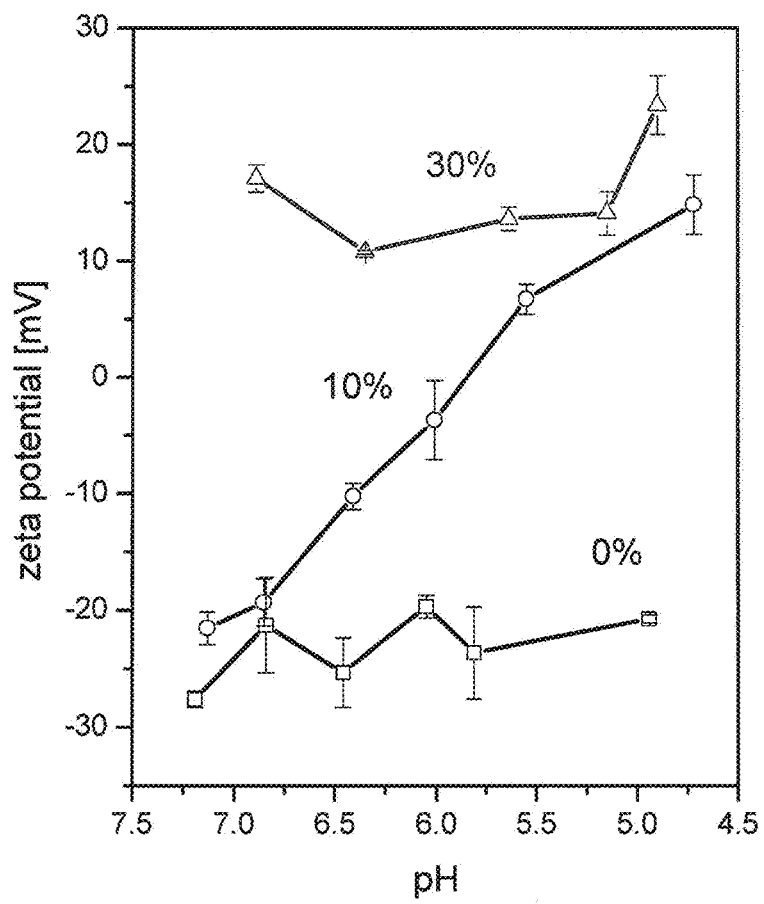
FIG. 3 shows a plot of zeta potential as a function of pH for various particle formulations, in accordance with one embodiment of the invention.

FIG. 3 shows how the zeta potential of the particles formed with the polymers indicated varied with pH. The particles containing PLH became significantly more positively charged than those without PLH when lowering the pH. The particles in FIG. 3 were formed by blending PLGA-block-PEG (PLGA-PEG) with PLGA-block-PLH (PLGA-PLH) prior to nanoprecipitation, and the 10% indicates that 10% (mol/mol) of the total polymer content was the PLGA-PLH, with the rest being PLGA-PEG in all instances. In addition, particles with 10% PLGA-PLH showed transition from negative charge to positive charge. Those with 30% PLGA-PLH remained positively charged. This indicates that the particle responsive behavior is sensitive to the ratio of PLGA to PLH.

Particle Response to Redox Potential

Figure 4:
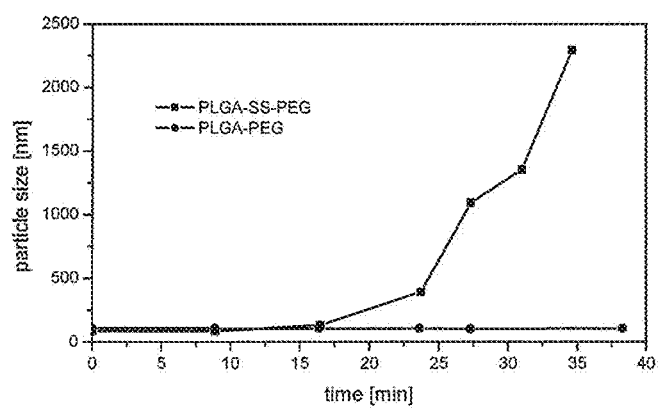
FIG. 4 shows a plot of particle size as a function of time of exposure to a dithiothreitol, in accordance with one embodiment of the invention.

FIG. 4 compares the nanoparticle size change as a function of time under a reducing environment containing 10 mM dithiothreitol (DTT). A control PLGA-PEG nanoparticle did not respond to the reducing environment. However, the size of nanoparticles formed from PLGA and PEG linked through a disulfide bond increased dramatically after 15 minutes indicating that PEG detachment occurred under the reducing environment.

Reversible Response of Nanoparticles

Figure 5:
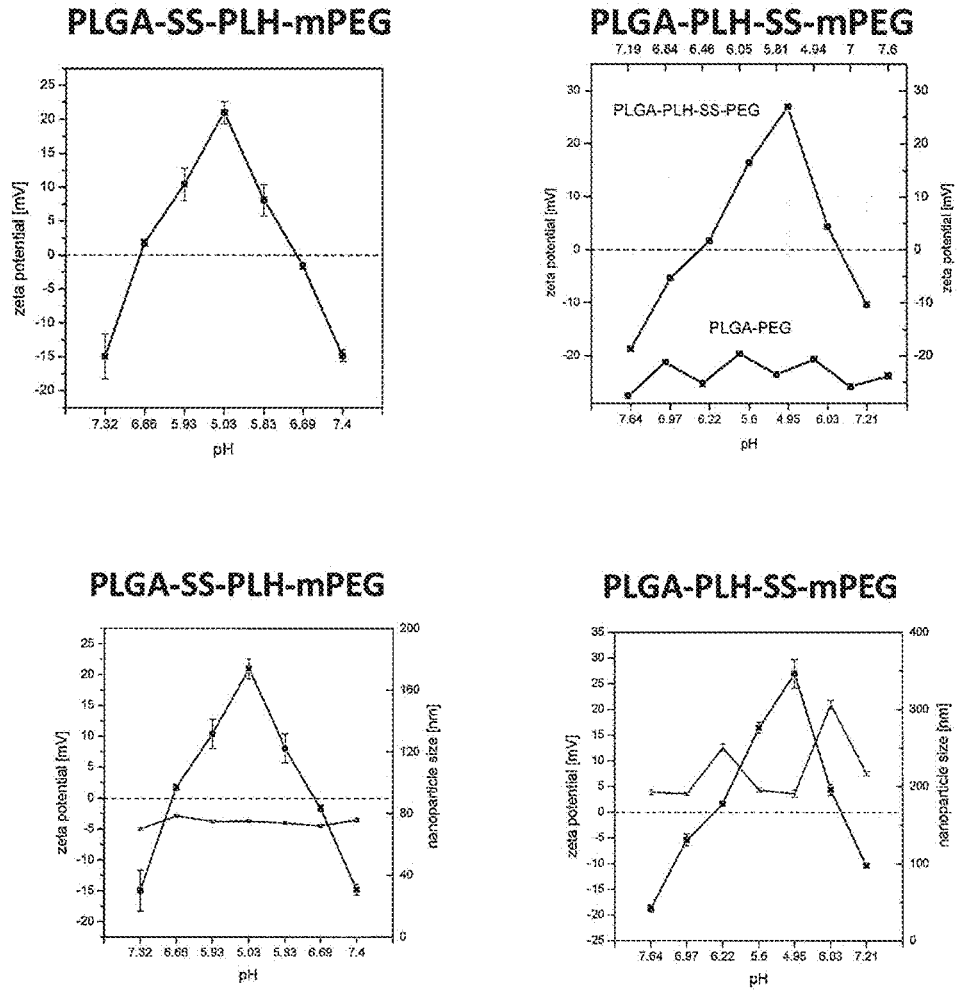
FIG. 5 shows plots of zeta potential (and nanoparticle size in two of the panels) as a function of pH, each in accordance with one embodiment of the invention.

As shown in FIGS. 5A and 5B, with the pH decrease from approximate pH 7.3 to approximate pH 5.0, the nanoparticle zeta potential changed from negative to positive. As a control, the curve (PLGA-PEG) in FIG. 5B shows the behavior of PLGA-PEG nanoparticles. The zeta potential of these nanoparticles remained essentially unchanged as the pH changes.

Ability of Nanoparticles to Encapsulate Hydrophilic Agents

Figure 6:
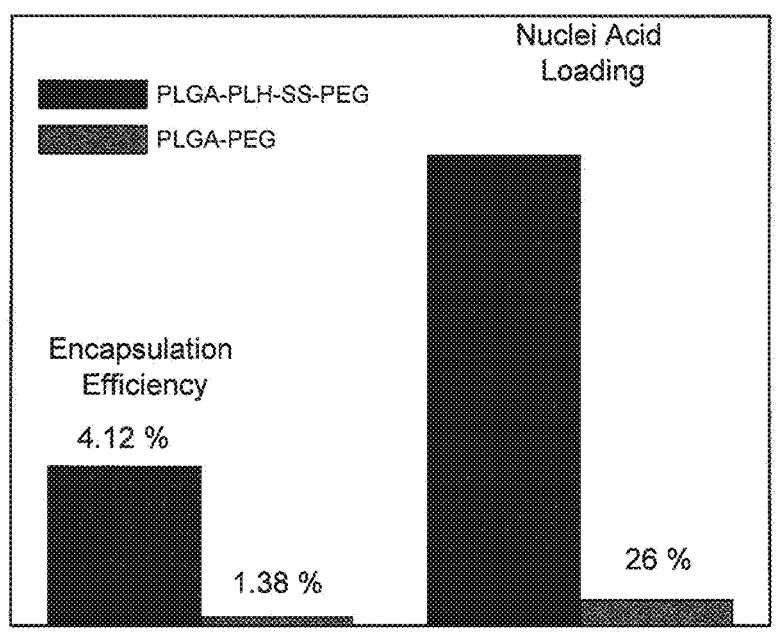
FIG. 6 compares the encapsulation efficiency of DNA by PLGA-PLH-SS-PEG versus PLGA-PEG, in accordance with one embodiment of the invention.

A 23-mer double stranded DNA was used as a model agent for the encapsulation experiment. Incorporating PLH into the nanoparticle can improve drug encapsulation ability, particularly for hydrophilic drugs. FIG. 6 compares the ability of PLGA-PLH-SS-PEG nanoparticles and PLGA-PEG nanoparticles to encapsulate siRNA. Particles containing both PLH and PLGA showed an increased encapsulation ability of nearly 3-fold. Using a single component, e.g. either PLGA or PLH, this high ability to encapsulate hydrophilic agents, particularly siRNA, could not be achieved.

Nanoparticle siRNA Delivery and Transfection Efficiency

Figure 7:
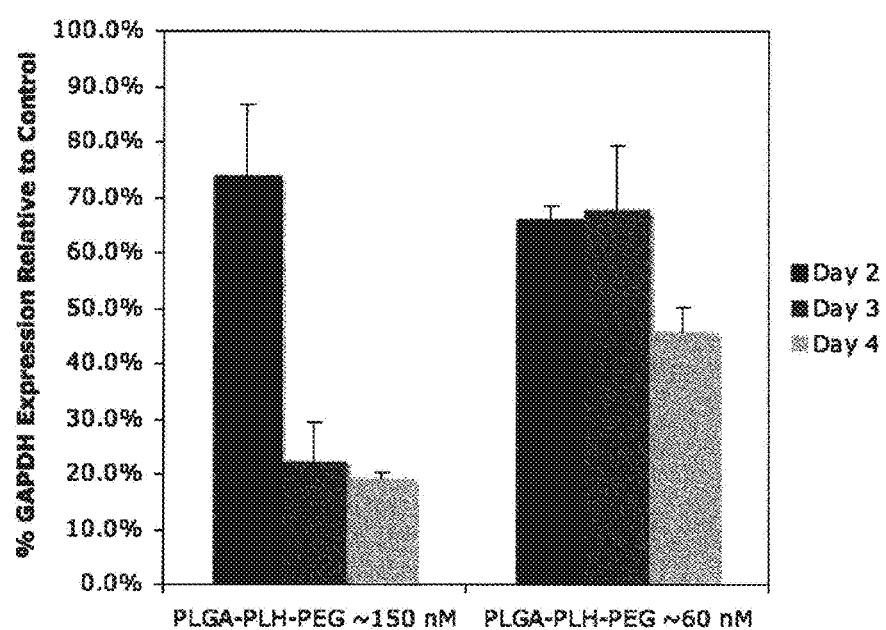
FIG. 7 compares the transfection efficiency of two concentrations of PLGA-PLH-PEG as a function of time, in accordance with one embodiment of the invention.
Figure 8:
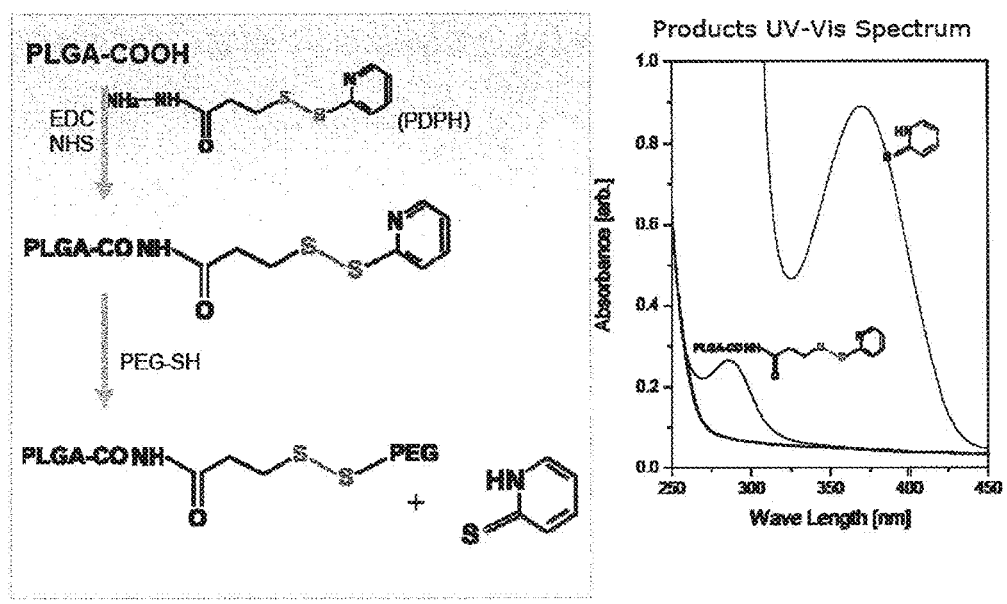
FIG. 8 illustrates the synthesis of disulfide-linked nanoparticles, in accordance with one embodiment of the invention.
Figure 9:
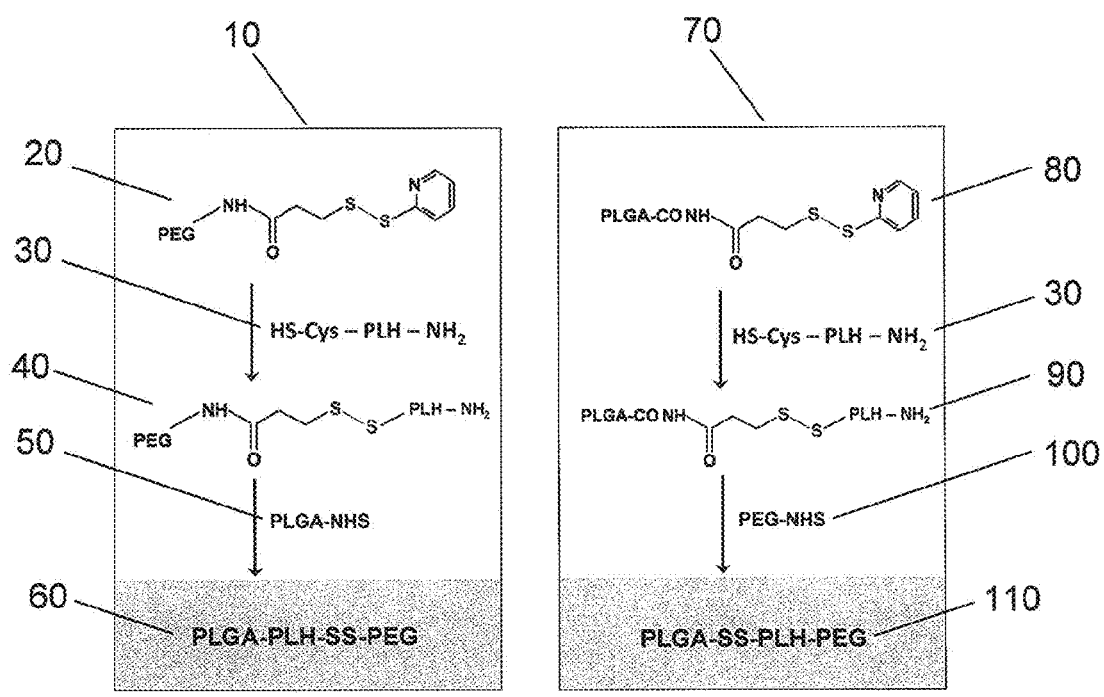
FIG. 9 shows synthetic schemes for producing PLGA-PLH-SS-PEG and PLGA-SS-PLH-PEG, in accordance with one embodiment of the invention. Non-limiting schemes 10 and 70 show the synthesis of two polymer conjugates according to embodiments of the present invention. PDPH-modified PEG 20 can be prepared by reacting NHS-activated PEG-COOH with PDPH. Reacting cysteine-terminated PLH 30 with the PDPH-modified PEG results in displacement of the 2-thiopyridinyl group of the PDPH with the cysteine thiol to form the PEG-SS-PLH conjugate 40. NHS-activated PLGA 50 can be reacted with the terminal amine on the PEG-SS-PLH conjugate to form the PLGA-PLH-SS-PEG conjugate 60. Alternatively, PDPH-modified PLGA 80 can be prepared by reacting NHS-activated PLGA with PDPH. The PDPH-modified PLGA can then be reacted with cysteine-terminated PLH 30 to yield the PLGA-SS-PLH conjugate (90). Subsequent reaction of the PLGA-SS-PLH with NHS-activated PEG-COOH (PEG-NHS) 100 to give the PLGA-SS-PLH-PEG conjugate 110. Modifications to these schemes will be apparent to those skilled in the art.
Figure 11:
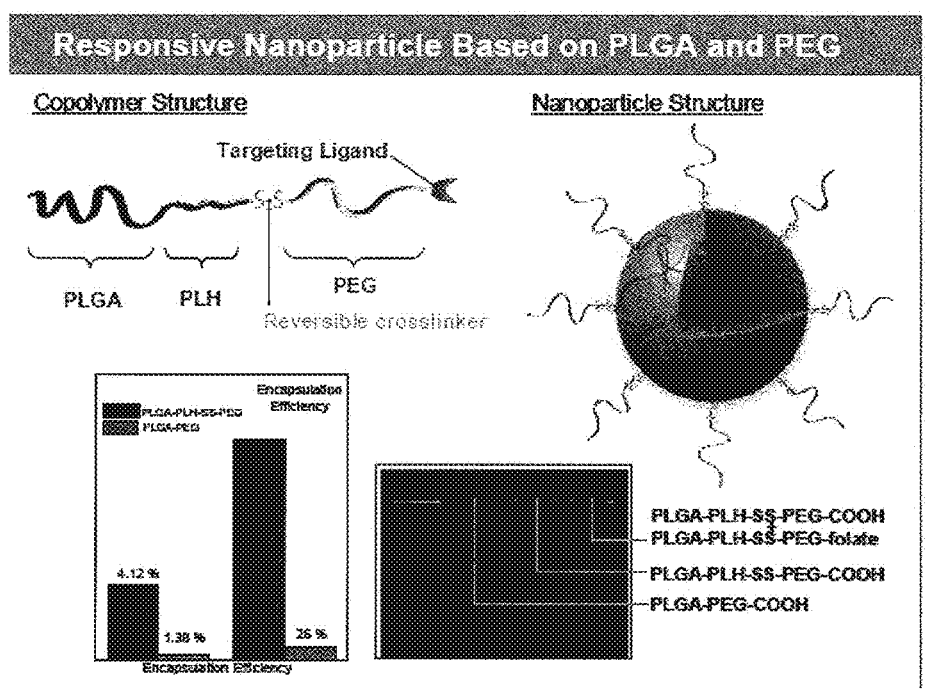
FIG. 11 exemplifies a copolymer structure, a nanoparticle structure and provides encapsulation efficiency and relative size data of exemplary polymers, each in accordance with one embodiment of the invention.
Figure 12:
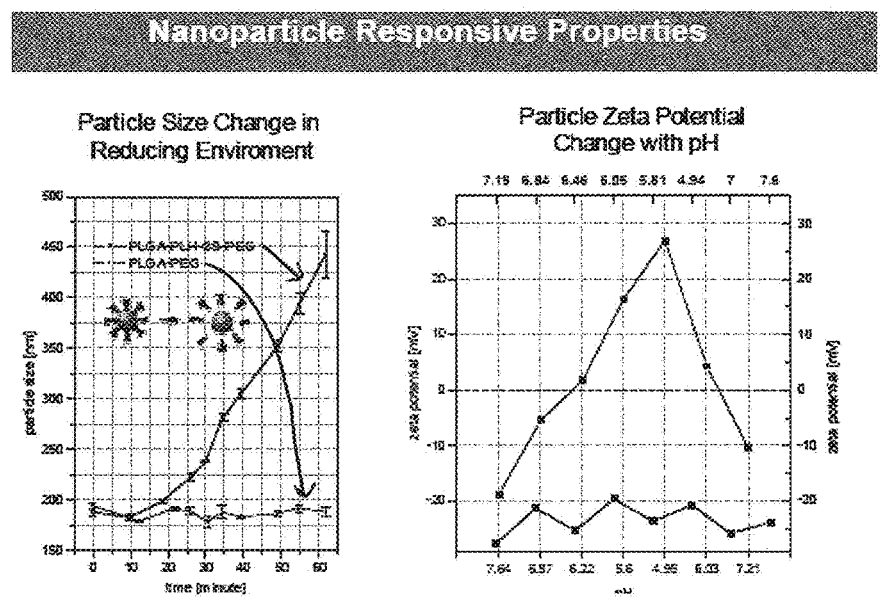
FIG. 12 shows the responsive properties of exemplary particles, in accordance with one embodiment of the invention.
Figure 13:
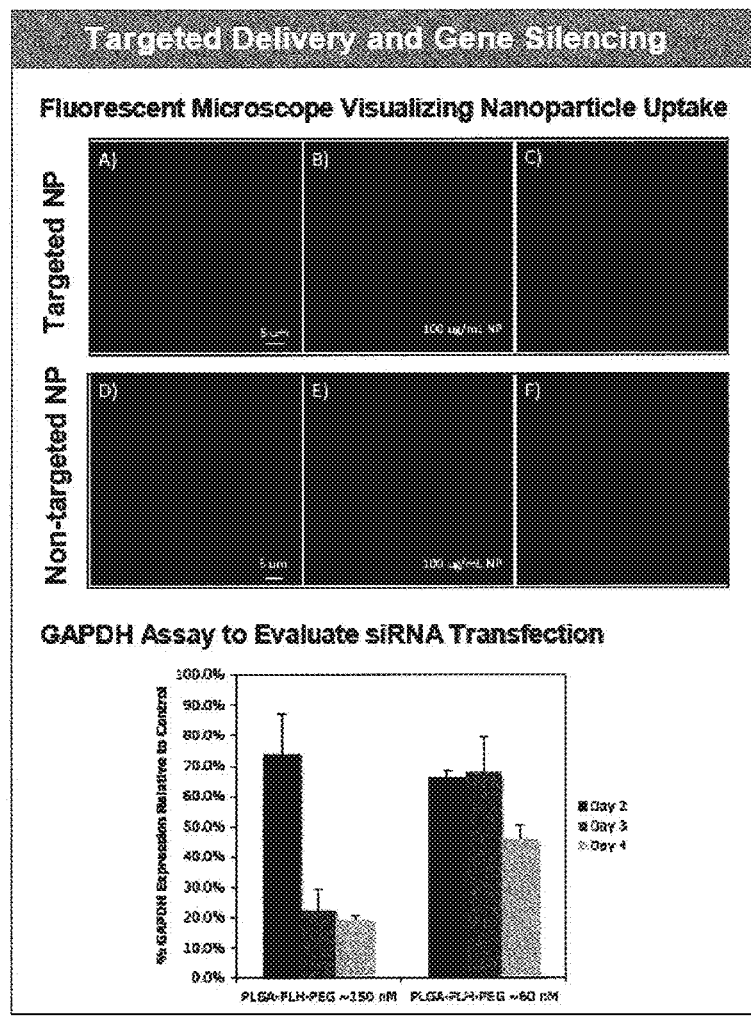
FIG. 13 demonstrates that targeted delivery and gene silencing was achieved with exemplary nanoparticles, in accordance with one embodiment of the invention.

GAPDH siRNA was encapsulated in PLGA-PLH-SS-PEG nanoparticles, and the ability of these nanoparticles to transfect prostate cancer cells was evaluated. As shown in FIG. 7, dramatic gene silencing (~80% decrease) was observed after dosing 150 nmol polymer nanoparticles to the prostate cancer cells.

The small interfering (siRNA) was successfully packaged, targeted and delivered into the cytoplasm of oral cancer (KB cells) and prostate cancer (22RV1 cells). The particles provided herein can be used as efficient carriers for nucleic acid (e.g., siRNA) delivery and gene silencing in, for example, cancer cells. This delivery system can be used to regulate androgen protein and improve prostate cancer treatment, as an example.

Example 6

Figure 14:
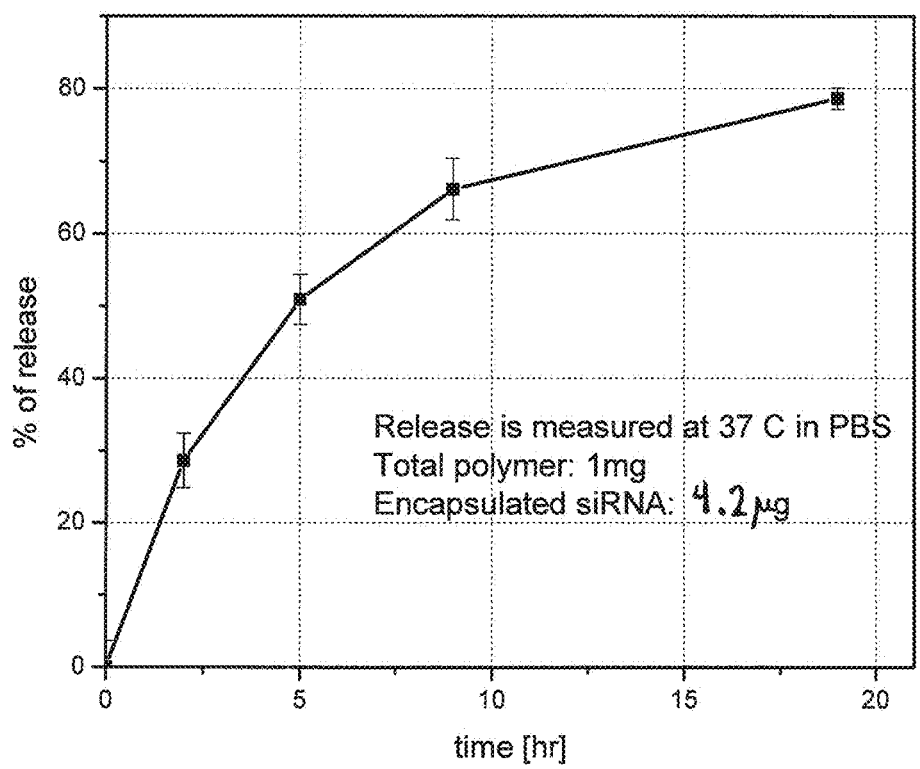
FIG. 14 provides a RNA release profile from PLGA-PLH-mPEG nanoparticles, in accordance with one embodiment of the invention.

To encapsulate a 23-mer GAPDH siRNA, 1 mg PLGA-PLH-mPEG polymer was dissolved in 0.6 mL chloroform to form the oil phase. 20 ug siRNA was dissolved in 0.02 mL water to form aqueous phase and was consequently emulsified in the oil phase. The obtained emulsion was further emulsified in 10 mL pH=7.5 water. The emulsion was stirred at room temperature for 5 hrs followed by the addition of 1.1 mL 10× PBS. Then the nanoparticle solution was transferred to 37° C. incubator. At each time point, 0.5 mL nanoparticle solution was taken from the original solution. Nanoparticle was removed by ultracentrifuge. The DNA concentration of the supernatant was analyzed by using PicoGreen assay (Invitrogen, Carlsbad, Calif.). The release of siRNA from PLGA-PLH-mPEG nanoparticles was evaluated. FIG. 14 shows that 50% of siRNA was released at 5 hrs after organic solvent evaporation. The experiment was carried out at 37° C. in PBS. The information provided by FIG. 14 can be used to adjust the timing of solvent evaporation, particle wash and siRNA delivery both in vivo and in vitro.

Example 7

In this experiment, 0.1 mg PLGA-Alexa488 (Invitrogen) and 1 mg PLGA-PLH-mPEG polymer were dissolved in 0.6 mL chloroform to form the oil phase. 0.2 mg Dextran-Rhodamine (Sigma-Aldrich) was dissolved in 0.02 mL water to form aqueous phase and was consequently emulsified in the oil phase. The obtained emulsion was further emulsified in 10 mL pH=7.5 water. The emulsion was stirred at room temperature for 5 hrs. The nanoparticles were then concentrated using Millipore-Amicon Ultra-4 Centrifugal Filter.

HUVEC cells were purchased from BD Biosciences and cultured HUVEC culture medium (Lonza, Basel, Switzerland) at 37° C. and 5% CO2. Cells were routinely passaged by treatment with trypsin (0.05%)/EDTA. For fluorescence microscopy imaging, HUVEC cells were seeded on a 4-well chamber slide with 15,000 cells/well and incubated at 37° C. and 5% CO2 for 24 hrs.

Next, the cells were incubated in fresh complete medium with NPs, followed by a 6-hr incubation at 37° C. and 5% CO2. After the incubation, the cells were washed three times in PBS and fixed in 4% paraformaldehyde at room temperature. For imaging, slides were mounted with a coverslip using H-1000 Vectorshield mounting medium with DAPI.

Figure 15:
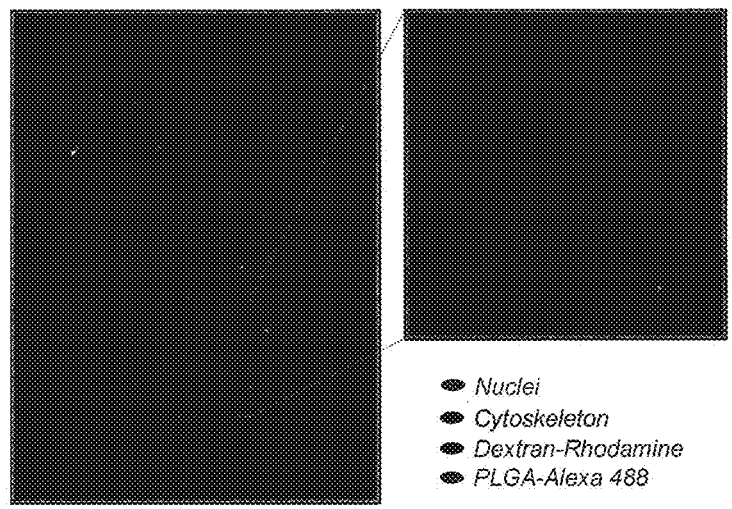
FIG. 15 demonstrates that co-delivery of both hydrophilic and hydrophobic agents can be accomplished with the compositions provided herein, in accordance with one embodiment of the invention.

Fluorescent analysis was carried out using an Applied Precision DeltaVision Spectris Microscope. As shown in the fluorescent image (FIG. 15), both hydrophobic and hydrophilic agents were successfully delivered into the cells.

Example 8

Materials and Methods
Cell Culture

On the day before the experiments, LNCaP prostate adenocarcinomas cells were plated at a density yielding 70% confluence on Corning CellBIND 6 well plates. Cells were grown in RPMI-1640 medium supplemented with 10% fetal bovine serum and 1% penicillin/streptomycin.

Nanoparticle Preparation

Nanoparticles were prepared by blending poly(lactic-co-glycolic acid)-block-poly(L-histidine)-block-poly(ethylene glycol) (PLGA-PLH-PEG) with poly(lactic acid)-block-poly(ethylene glycol)-targeting moiety (PLA-PEG-targeting moiety) and poly(lactic-co-glycolic acid)-Alexa-488 (PLGA-Alexa-488) at different weight % in a total volume of 600 uL of chloroform organic phase of the double emulsion. These 600 uL of polymer-containing chloroform were emulsified into 2 mL of water using a probe tip sonicator for 45 seconds in pulsed mode. The organic solvent was evaporated over a period of 6 hours, yielding 200 nm nanoparticles suspended in water.

Incubation of Nanoparticles with Cells and Flow Cytometry

Nanoparticles were incubated with LNCaP cells either in the presence or absence of a targeting moiety. The total incubation time for nanoparticles with cells was 14 hours, which was sufficient to produce significant acidification of the cell growth medium.

Right before flow cytometry analysis, the cells were trypsinized, collected, then resuspended in PBS. The cells were run in a BD FACSCalibur flow cytometer in order to detect fluorescence from the Alexa-488 conjugated to the nanoparticles.

Results

Figure 16:
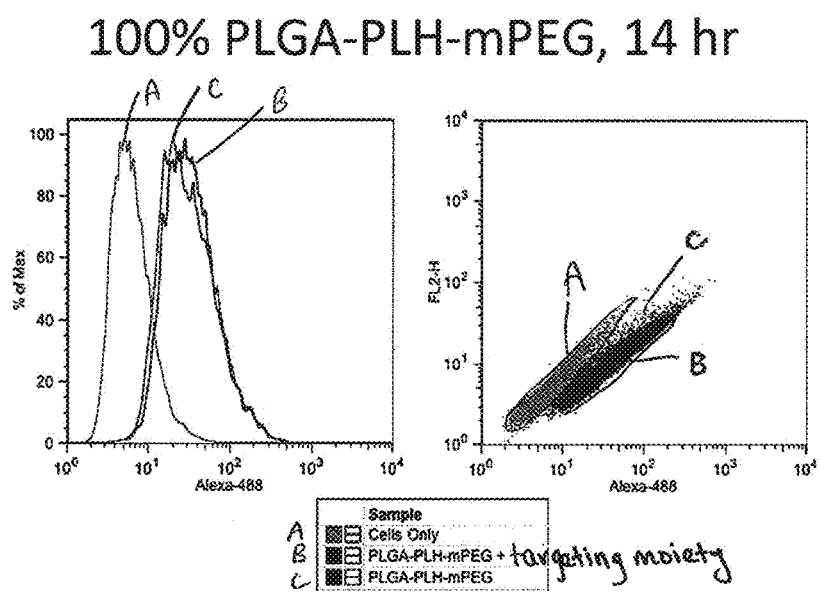
FIG. 16 shows the uptake of 100% PLGA-PLH-mPEG, in accordance with one embodiment of the invention.

FIG. 16 demonstrates that at a pH<6, considerable uptake of untargeted PLGA-PLH-mPEG nanoparticles occurred. This result is secondary to the cationic charge that is produced on the nanoparticle surface at low pH as a result of the presence of the PLH. Cationic nanoparticles have been shown previously to bind to the surface of negatively charged cells and, in some cases, to lead to internalization. In addition, these data show that uptake can occur without the use of a targeting moiety but simply through a charge-charge interaction at low pH (pH<6). In some embodiments, therefore, the particles, polymers and any of the compositions provided herein do not include a targeting moiety.

Figure 17:
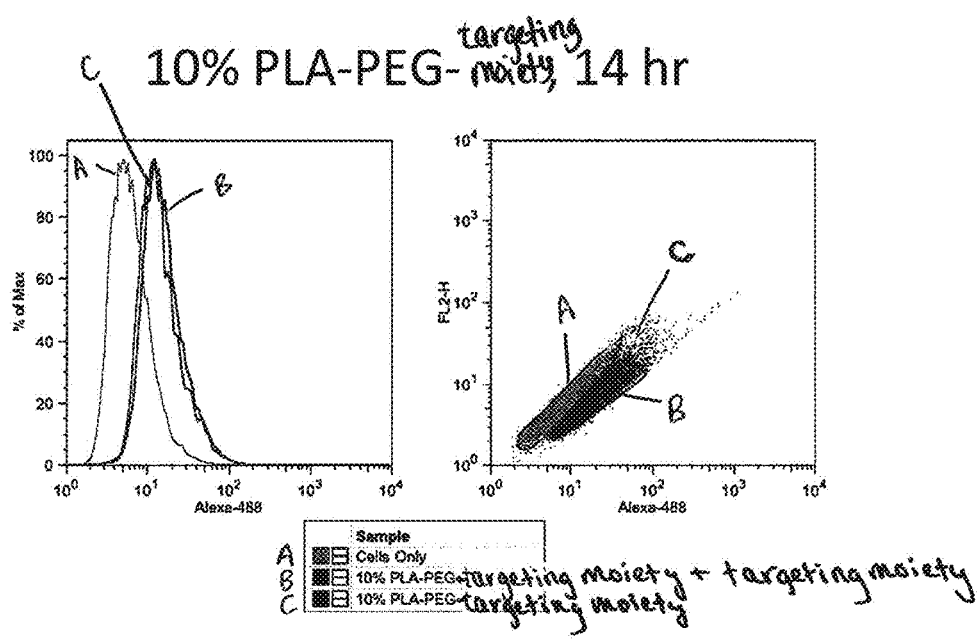
FIG. 17 shows the uptake of a 10% PLA-PEG-targeting moiety formulation, in accordance with one embodiment of the invention.
Figure 18:
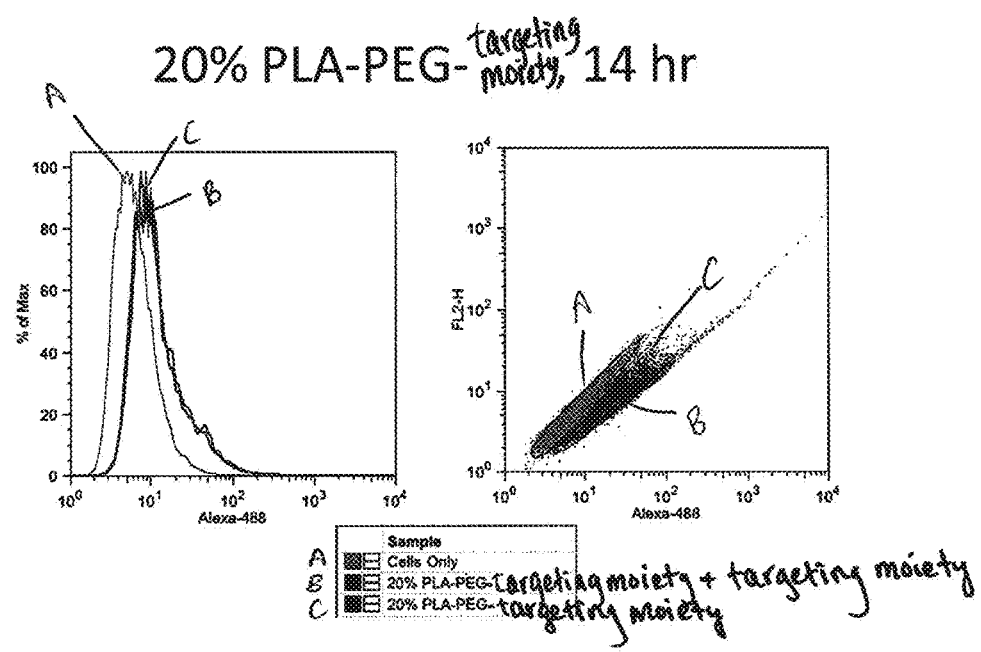
FIG. 18 shows the uptake of a 20% PLA-PEG-targeting moiety formulation, in accordance with one embodiment of the invention.

FIGS. 17 and 18 show that blended nanoparticles also showed non-specific pH-dependent uptake. In fact, this low pH targeted effect dominates for the particular nanoparticle formulations tested.

Figure 19:
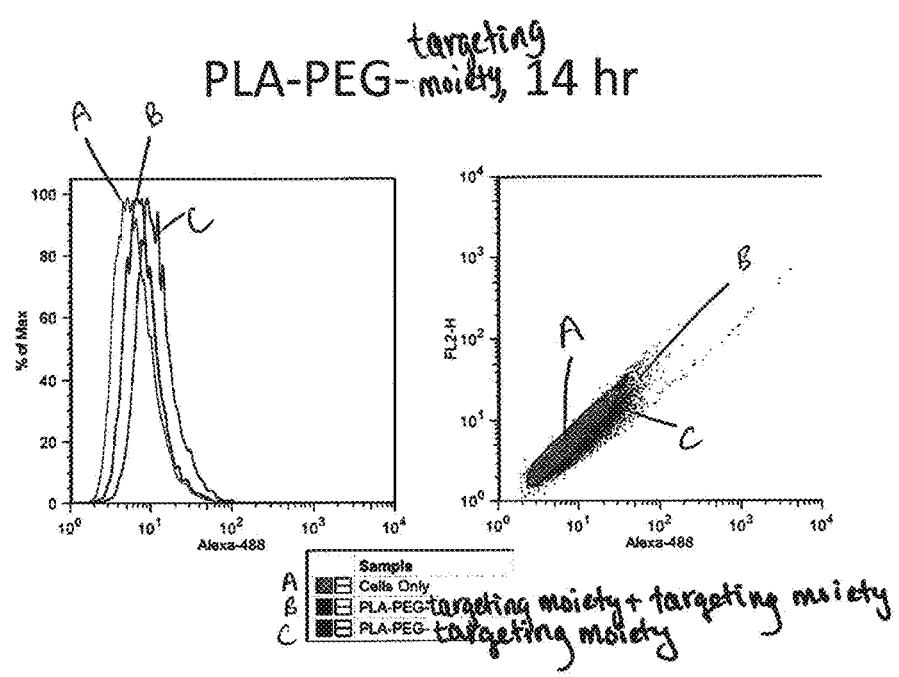
FIG. 19 shows the uptake of PLA-PEG-targeting moiety, in accordance with one embodiment of the invention.
Figure 20:
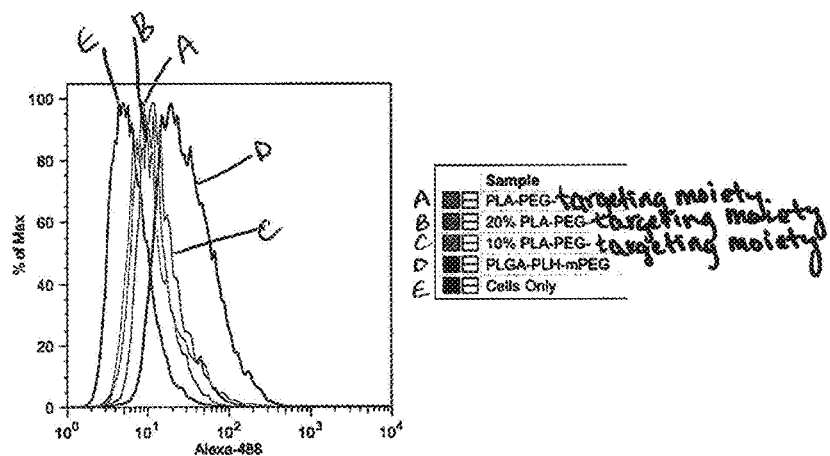
FIG. 20 illustrates how untargeted nanoparticle uptake dominates in this assay, in accordance with one embodiment of the invention.

FIGS. 19 and 20 further illustrate the above results.

Figure 32:
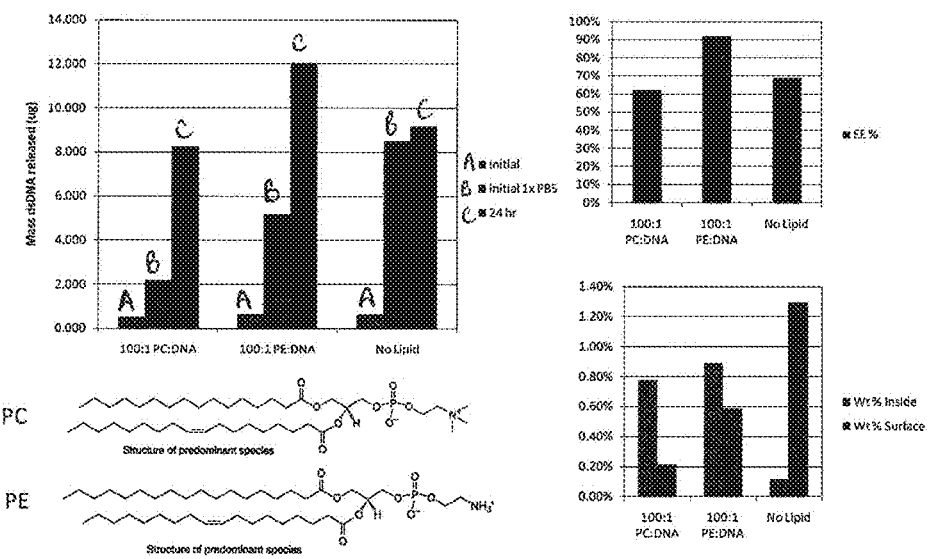
FIG. 32 shows how neutral lipids shift loading towards the interior of the particle, in accordance with one embodiment of the invention.
Figure 33:
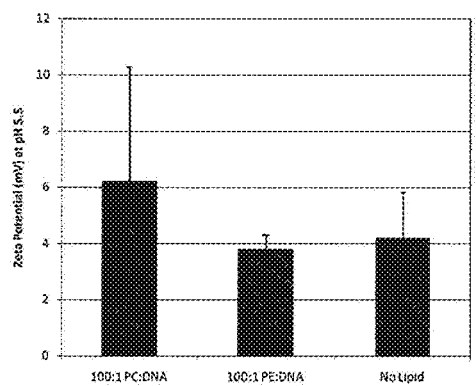
FIG. 33 demonstrates that neutral lipids do not affect generation of cationic charge at low pH. This shows that neutral lipids can be used to produce the particles provided herein, in accordance with one embodiment of the invention.

FIGS. 32 and 33 demonstrate that addition of neutral lipids can enhance drug encapsulation by shifting the encapsulation of negatively charged nucleic acids to the interior. Inclusion of neutral lipids to enhance nucleic acid encapsulation did not adversely affect the positive surface charge that is produced at low pH.

Example 9

Materials and Methods

PEG reagents (mPEG-NH—$NH_2$ and tBoc-NH-PEG-$NH_2$) were purchased from LaysanBio Inc. SPDP was purchased from Thermo Fisher Scientific Inc. (Waltham, Mass.). (Benzotriazol-1-yloxy)tripyrrolidinophosphonium hexafluorophosphate (pyBOP), N-Hydroxybenzotriazole (HOBt), and Boc-Lys(Dabcyl)-COOH were purchased from Anaspec Inc. (Fremont, Calif.). OG488 was purchased from Invitrogen Inc. O-Bis-(aminoethyl)ethylene glycol trityl resin was purchased from EMD Chemicals Inc. (Darmstadt, Germany). All other chemicals including folic acid, 1-ethyl-3-[3-dimethyl-aminopropyl]carbodiimide hydrochloride (EDC), N-Hydroxysuccinimide (NHS), and N,N-diiso-propylethylamine (DIEA) were purchased from Sigma-Aldrich.

Dialysis was performed using 2K Slide-A-Lyzer® cassettes, and the gel filtration was carried out on D-Salt Dextran desalting columns, both from Thermo Fisher Scientific. MALDI-TOF analysis was performed on an Applied Biosystems Model Voyager DE-STR instrument in the Biopolymer Laboratory at the Massachusetts Institute of Technology (MIT). UV-Vis measurements were performed using a Varian Cary 100 UV-Vis spectrophotometer.

Synthesis of (4) mPEG-(Dabcyl)-$NH_2$ Boc-Lys(Dabcyl)-COOH (23 mg, 0.046 mmol), NHS (26 mg, 0.23 mmol) and EDC (44 mg, 0.23 mmol) were dissolved in 1 mL DMF, to which 0.5 mL DMF containing 29 mg mPEG-NHNH$_2$ (0.0058 mmol) and 20 µL DIEA (0.11 mmol) was added. The mixture was stirred in the dark at room temperature. After 14 hrs, the mixture was precipitated in 50 mL diethyl ether to produce a bright red solid, followed by washing using diethyl ether. After a standard BOC deprotection using TFA, the product was purified by dialysis and gel filtration. After lyophilizing, the compound (4) was collected as a bright yellow powder. The conjugation was confirmed using MALDI-TOF.

Synthesis of (5) mPEG-(Dabcyl)-OPSS SPDP (7.8 mg, 0.025 mmol) was dissolved into DMF (0.2 mL). The solution was then added to 25 mg mPEG-(Dabcyl)-$NH_2$ (4, 0.005 mmol). After the solid was dissolved, 10 µL DIEA (0.055 mmol) was added. The mixture was stirred in the dark at room temperature. After 14 hrs, the reaction was terminated by adding 2 mL water. After dialysis and lyophilization, the compound (5) was collected as a brown powder. The conjugation was confirmed by MALDI-TOF.

Synthesis of (10) OG488-Cys(Trt)-ONH—$CH_2CH_2OCH_2CH_2O$—NH-trityl resin Bis-(2-aminoethyl)-ether trityl resin (30 mg) was loaded into an solid phase reactor and pre-swelled in DMF for 4 hrs at room temperature. Fmoc-Cys(Trt)-OH (94 mg, 0.16 mmol), pyBOP (124.8 mg, 0.24 mmol) and HOBt (37 mg, 0.24 mmol) were dissolved into 0.5 mL dry DMF and added to the resin together with DIEA (20 µL, 0.11 mmol). The reaction was carried out in the dark for 16 hrs, followed by DMF wash and piperidine treatment (1 mL, 20% in DMF) to deprotect the amine of the cysteine. The conjugation and deprotection were confirmed by the ninhydrin test. After washing in DMF, OG488-NHS (10 mg, 0.02 mmol) and DIEA (20 µL, 0.11 mmol) in 0.5 mL DMF was added to the resin. The mixture was stirred in the dark for 16 hrs, followed by DCM wash. The functionalized resin was then dried under vacuum.

Synthesis of (12) mPEG-(Dabcyl)-SS-(OG488)-$NH_2$ 30 mg functionalized resin (10) was treated with the mixture of 0.1 mL TFA, 0.4 mL DCM, 30 µL water and 10 µL triisopropylsilane for 2 hrs. The solvent was evaporated at room temperature under vacuum. Water (2 mL) was added to the dried product to extract the cleaved molecule. The extraction was then added to 25 mg (2). The solution was stirred in the dark at room temperature for 12 hrs. The product (12) was purified by dialysis and gel filtration, followed by lyophilization, and was collected as a dark brown powder. The conjugation was confirmed by MALDI-TOF.

Synthesis of PLGA-(OG488)-SS-(Dabcyl)-mPEG PLGA-COOH was activated to form PLGA-NHS through EDC/NHS chemistry as reported.[9] Briefly, 100 mg PLGA-COOH was dissolved into DCM (1 mL), to which 0.5 mL DCM containing EDC (5 mg, 0.027 mmol) and NHS (3 mg, 0.027 mmol) was added. The mixture was stirred at room temperature for 2 hrs. PLGA-NHS was then precipitated by addition of cold methanol (50 mL) and dried under vacuum. The collected polymer was dissolved in 1 mL dry DMSO, to which 25 mg mPEG-(Dabcyl)-SS-(OG488)-$NH_2$ (compound 12, ~0.0042 mmol) and 10 µL DIEA (0.055 mmol) was added. The mixture was stirred in the dark for 16 hrs. The product was precipitated by the addition of 50 mL cold methanol. As a final purification, the polymer was repeatedly dissolved in DMF followed by precipitation in cold methanol, and finally dried in vacuum.

To synthesize folate-targeted NPs by nanoprecipitation and self-assembly, PLGA-PEG-folate (1.5 mg in 0.15 mL acetonitrile), PLGA-(FRET)-PEG (1.5 mg in 0.15 mL acetonitrile) and acetonitrile (0.2 mL) were mixed and added dropwise into a 7 mL vial of DI H₂O under gentle stirring. The organic solvent phase was allowed to evaporate in the dark for 16 hrs under gentle stirring. The NPs were washed with ultra pure water using 100 kDa Amicon Ultra centrifugal filters and concentrated to 0.2 mL. The NPs were transferred into buffered solutions by a slow addition of 0.022 mL 10× PBS before the NPs were added to cells.

KB cells were purchased from ATCC and cultured in RPMI medium (RPMI-1640 containing 1 mg/L FA, Invitrogen) with 10% fetal bovine serum, 2 mM glutamine, 50 units/mL penicillin and 50 ug/mL streptomycin at 37° C. and 5% $CO_2$. Cells were routinely passaged by treatment with trypsin (0.25%)/EDTA. Before the cells were incubated with NPs, cells were cultured overnight in FA-free RPMI medium with the same additives.

For fluorescence microscopy studies, KB cells were seeded on a 4-well chamber slide with 15,000 cells/well and incubated at 37° C. and 5% $CO_2$ for 24 hrs. Next, the cells were incubated in fresh complete medium with NPs, followed by a 6-hr incubation at 37° C. and 5% $CO_2$. After the incubation, the cells were washed three times in PBS and fixed in 4% paraformaldehyde at room temperature. For imaging, slides were mounted with a coverslip using H-1000 Vectorshield mounting medium with DAPI. Fluorescent analysis was carried out using an Applied Precision DeltaVision Spectris Microscope.

Flow cytometry analysis was performed on a BD Biosciences FACSCalibur HTS at the MIT Koch Institute flow cytometry core facility. KB and HUVEC cells were seeded on 6-well plates with a density of 200,000 cells/well and incubated overnight. To allow nanoparticle uptake, cells were incubated with 0.5 mg/mL NPs for 4 hrs at 37° C. and 5% $CO_2$. Before flow cytometry analysis, cells were washed with PBS, trypsinized, and re-suspended in PBS containing 0.4% BSA. Each flow cytometry result was collected from 12,000 live cells.

Figure 27:
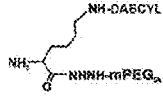
FIG. 27 shows results from a MALDI-TOF analysis of intermediates in PEG conjugation to form the FRET-bearing PEG, in accordance with one embodiment of the invention.

MALDI-TOF analysis of (2) mPEG-NH—NH₂, (4) mPEG-(Dabcyl)-NH₂, (6) mPEG-(Dabcyl)-OPSS, and (12) mPEG-(Dabcyl)-SS-(OG488)-NH₂ The conjugation products (2), (3), (4) and (10) to form FRET bearing PEG molecule were confirmed using MALDI-TOF (FIG. 27). The starting material mPEG-NH—NH₂ gives maximum intensity at m/e=5586. The first step conjugation introduces a lysine-Dabcyl molecule to the PEG, followed by standard BOC deprotection. The maximum intensity is found at m/e=5960. The molecule is further conjugated with SPDP and the molecular weight (MW) increases to m/e=6158. In the final step of conjugation, thiol replacing reaction forms the FRET pair, which gives m/e=6690.

Synthesis and characterization of PEG-folate conjugation Folic acid (8.8 mg, 0.02 mmol) was dissolved in 1 mL dry DMSO, to which 0.5 mL DMSO containing pyBOP (26 mg, 0.05 mmol) and HOBT (7.2 mg, 0.05 mmol) was added. After mixing, the solution was added to tBOC-NH-PEG-NH₂ (50 mg, 0.01 mmol) with DIEA (20 μL, 0.11 mmol). The solution was stirred in the dark at room temperature for 16 hrs. The reaction mixture was added dropwise to diethyl ether (50 mL) to precipitate a yellow solid. After BOC deprotection, the product was purified using dialysis and gel filtration. The product was collected as a light yellow solid after lyophilization.

Figure 28:
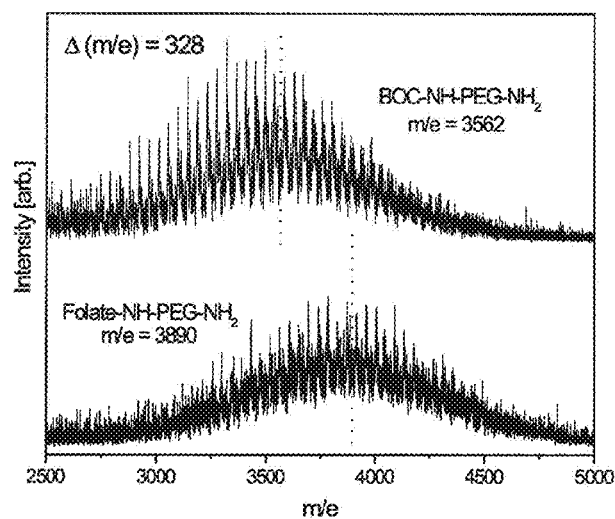
FIG. 28 shows results from a MALDI-TOF analysis of folate conjugation to PEG, in accordance with one embodiment of the invention. The starting material was BOC-NH-PEG-NH$_2$. The conjugation introduced a folic acid molecule to the PEG chain, followed by the BOC deprotection. The molecular weight increase of 328 Da from the spectra is consistent with the theoretical calculation.

The PEG-folate conjugation was first confirmed using MALDI-TOF (FIG. 28). The starting material BOC-NH-PEG-NH₂ gives maximum intensity at m/e=3562. The conjugation introduces a folic acid molecule to the PEG chain (folate MW: 441), followed by BOC deprotection (BOC MW: 110). The MALDI-TOF gave maximum intensity at m/e=3890. The net molecular weight increase is 328.

Figure 29:
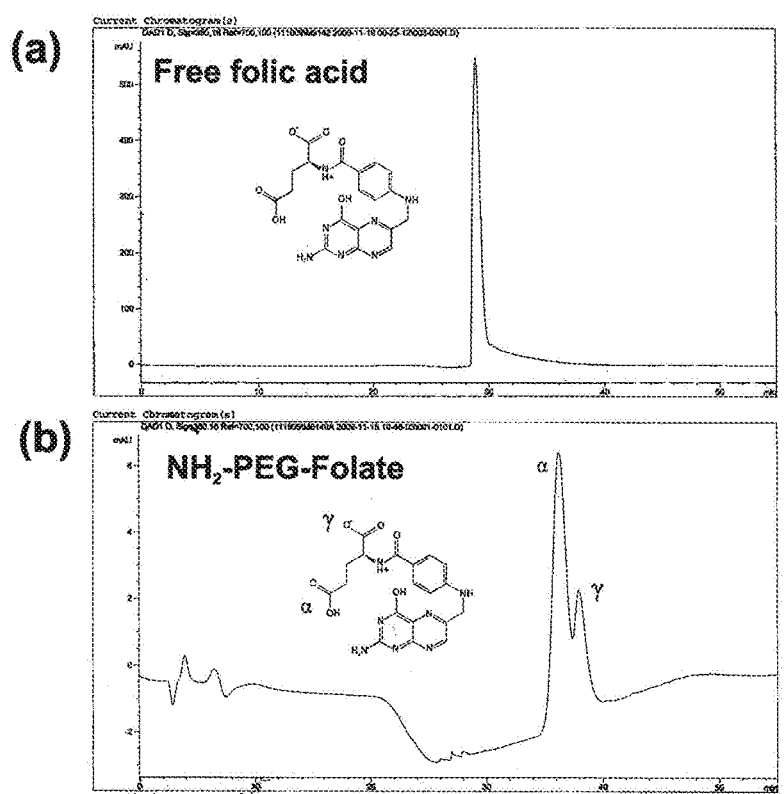
FIG. 29 shows results of a HPLC analysis of folate conjugation with PEG. (A) free folic acid elutes at 29 minutes. After conjugation in (B), folate elutes at 36 and 38 minutes, respectively, corresponding to the two conjugation isomers, each in accordance with one embodiment of the invention.
Figure 31:
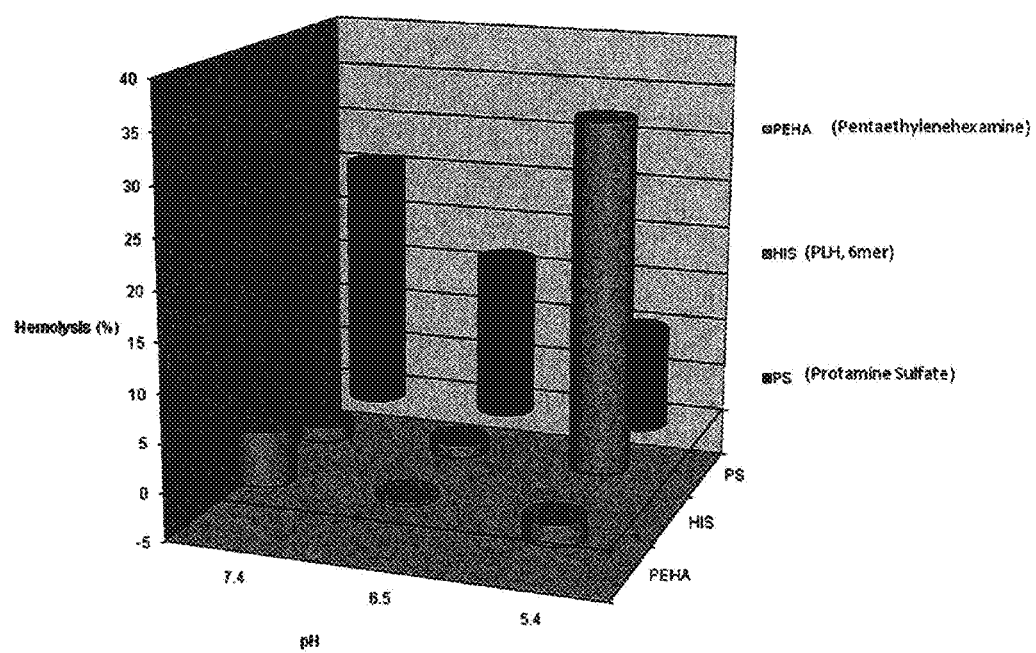
FIG. 31 provides results from a pH dependent hemolytic assay, in accordance with one embodiment of the invention.

The conjugation was further analyzed using HPLC. The retention time of the free folate was 29 minutes (FIG. 29A). After the conjugation, the folate eluted with two peaks at 36 minutes and 38 minutes, respectively (FIG. 29B). The retention time shift indicates the conjugation of folate to the PEG. The two-peak profile of the products results from the conjugation at β and γ carboxyl groups on folic acid, respectively.

NH₂-PEG-folate was conjugated with PLGA using the same procedure described above.

Verification of receptor mediated NP uptake NP uptake mediated by the targeting ligand was first verified using PLGA-PEG-folate NPs. In order to analyze the uptake using flow cytometry, PLGA-Alexa488 was blended for encapsulation. The NPs blended with 1.5 mg PLGA-mPEG, 1.5 mg PLGA-PEG-folate and 0.3 mg PLGA-Alexa488 showed enhanced uptake compared with the NPs that have no PLGA-PEG-folate (FIG. 30A). In another uptake experiment, the NPs were formulated using 1.5 mg PLGA-mPEG, 1.5 mg PLGA-PEG-folate and 0.3 mg PLGA-Alexa488. The uptake was inhibited by the addition of 2 mM free folic acid into the culture medium (FIG. 30B).

Results

A novel FRET-bearing poly(ethylene glycol) (PEG) conjugate fluoresces at 520 nm when it is cleaved off from nanoparticles (NPs). When the NPs were targeted to cancer cell lines, the reducing redox of the endosomal compartment caused disulfide bond cleavage and shedding of the PEG layer. The fluorescence emission can be suppressed by N-ethylmaleimide to inhibit disulfide cleavage and restored by dithiothreitol, a disulfide cleavage reagent, indicating a direct correlation between fluorescence emission and PEG shedding.

The surface functionalization of nanoparticle (NP) drug delivery systems with poly(ethylene glycol) (PEG) has become a preferred coating strategy to increase NP circulation time by reducing protein opsonization and macrophage uptake.[1, 2] Indeed, several clinically-approved therapeutics rely on PEG for improved in vivo profiles, including PEG-liposomes (e.g., Doxil®), PEG-drug conjugates (e.g., Oncaspar®) and polymeric NPs (e.g., Genexol-PM®).[3] However, it has been reported that the benefit from using PEG to increase circulation half-time may be compromised by PEG which may cause steric and electrostatic hindrance to the entry of NPs at target sites.[4] Even after the NPs are endocytosed at these target sites, the PEG layer can still act as a diffusion barrier to NPs for the efficient release of their payloads.[5] To overcome this 'PEG dilemma', it has been proposed that PEG-sheddable NPs may be formulated by crosslinking PEG using disulfide bond that is cleaved in response to the reducing conditions.[6]

Research has shown that some NP delivery systems, when equipped with disulfide-linked sheddable PEG, show cell-responsive dynamics and improved delivery of therapeutic molecules. For example, Takae et al. reported poly(aspartamide) based plasmid gene delivery NPs that showed enhanced gene expression by using cleavable disulfide bonds to crosslink the stealth PEG layer.[7] In another example, Cerritelli et al. observed faster cytoplasm release of calcein from NPs formed using PEG-SS-poly(propylene sulfide) co-polymers when compared with a non-cleavable formulation.[8] However, so far, currently known assays to evaluate PEG shedding are end-point focused and yield no information of the PEG shedding process during NP-cell interactions. In addition, these functional assays are unique to the delivery of the specific payloads, and thus may not be generalized across NP systems. In an effort to rationally design PEG-sheddable NPs for efficient and environment-sensitive delivery, a method to directly observe PEG-shedding across various NP systems and conditions was developed.

Figure 21:
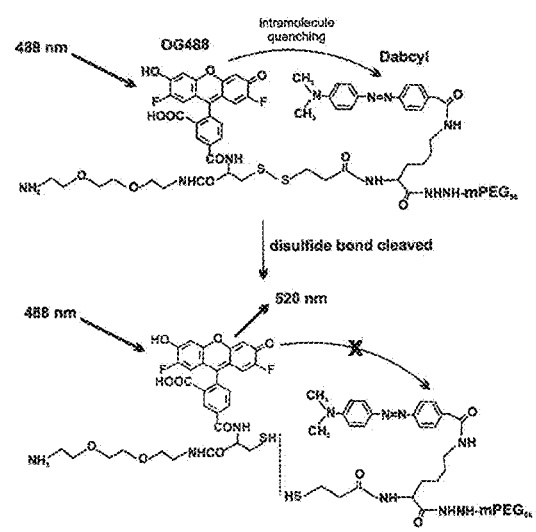
FIG. 21 shows the design of FRET-bearing PEG that allows the direct observation of its shedding, in accordance with one embodiment of the invention.

A PEG molecule that bears a disulfide-based fluorescence resonance energy transfer (FRET) pair was designed and synthesized containing an Oregon Green-488 (OG-488) as donor and a Dabcyl molecule as quencher (FIG. 21). When the disulfide bond is intact, only minimal fluorescence from OG-488 can be detected due to intramolecular quenching. However, if the PEG chain is shed due to disulfide cleavage, intramolecular quenching is abolished and increased fluorescence can be measured. Notably, the design preserves a reactive amine group in the FRET-bearing PEG molecule, which allows for conjugation to different NP systems. In this study, the FRET-bearing PEG molecule was conjugated with poly(lactic-co-glycolic acid) (PLGA) to form PLGA-(FRET)-PEG NPs as a model polymeric NP platform. Using this NP formulation, intracellular PEG shedding during NP endocytosis was directly visualized.

Figure 22:
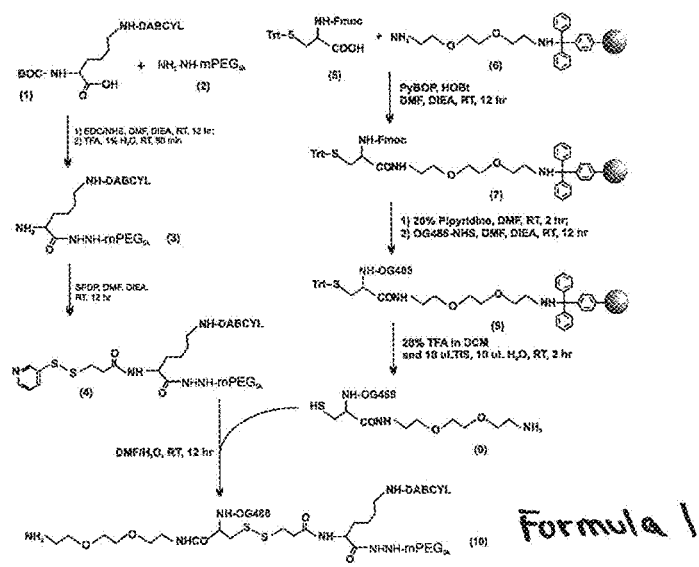
FIG. 22 shows a scheme for the chemical synthesis of FRET-bearing PEG, in accordance with one embodiment of the invention.

The chemical synthesis to form the FRET-bearing PEG molecule is illustrated in FIG. 22. Specifically, Dabcyl was introduced by conjugating BOC-Lysine(COOH)-Dabcyl (1) to PEG-hydrazide (2) using EDC/NHS coupling. After standard BOC deprotection using trifluoroacetic acid (TFA), a disulfide bond was introduced by a heterofunctional cross-linker, N-succinimidyl-3-(2-pyridyldithio)-propionate (SPDP), which allows for subsequent disulfide coupling to thiol-containing molecules. The products in each conjugation step were purified using dialysis and gel filtration. Next, solid phase synthesis was used to assemble a small molecule (9) that contains a free thiol, amine and OG488 dye. Here, Fmoc-Cys(Trt)-OH was first conjugated to Bis-(2-aminoethyl)-ether trityl resin through pyBOP/HOBt coupling, followed by Fmoc deprotection using 20% (v/v) piperidine in DMF. Both conjugation and deprotection reactions were confirmed by the ninhydrin test. The resin was then reacted with amine-reactive OG488 dyes to assemble (8). Since the thiol of cysteine is protected by a trityl group, thiol deprotection and resin cleavage could thus be carried out in a single TFA treatment. After the solvent was removed by vacuum, the molecule (9) was immediately mixed with (4) in water to avoid potential thiol oxidation. The coupling reaction between thiol and pyridyl disulfide resulted in the formation of the final FRET-bearing PEG molecule (10). Notably, the amine group preserved in the final molecular structure provided a functional end-group for further conjugation of FRET-bearing PEG to different NP systems.

Figures 23A, 23B:
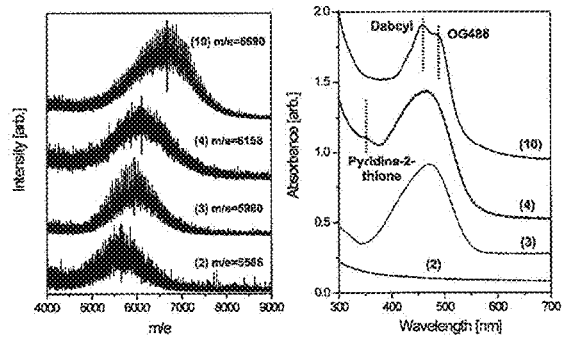
FIG. 23(A) provides results of a MALDI-TOF analysis and (B) provides results of UV-Vis spectroscopy of conjugation products to form the FRET-bearing PEG, each in accordance with one embodiment of the invention.

To confirm the conjugation reactions in FIG. 22, matrix-assisted laser desorption and ionization time-of-flight (MALDI-TOF) mass spectrometry was used to analyze key products 1, 3, 4 and 10, and plotted in FIG. 23A. The molecular weight of each product measured from the spectra matches the predicted values. UV-Vis spectroscopy provided a simple and direct method to further confirm the MALDI-TOF analysis. As shown in FIG. 23B, the initial mPEG-hydrazide molecule (1) did not show obvious absorption at 300-700 nm. After conjugation with BOC-Lysine-(COOH)-Dabcyl (2), an absorption maximum at 460 nm was observed which matches the adsorption of the Dabcyl molecule. Further conjugation with SPDP led to the formation of (4), which showed an additional absorption peak at 340 nm, originating from the 2-pyridyldithio group of the SPDP molecule. This 340 nm absorption diminished after the final reaction between (4) and (9) due to the replacement of 2-pyridyldithio by the thiol group in (9). Moreover, an additional peak at 490 nm was observed, which is consistent with the absorption wavelength of OG488. This double-peak feature of the UV absorption spectrum confirmed FRET pair formation in the final product (10).

Figure 24:
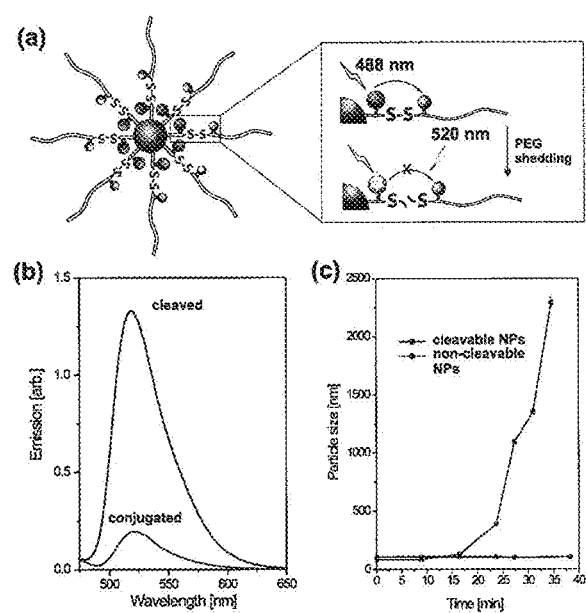
FIG. 24(A) shows the nanoparticle structure using PLGA-(FRET)-PEG copolymer through nanoprecipitation. (B) provides results of a fluorescence emission spectroscopy which show that the disulfide cleavage induces a nearly 6-fold increase in 520 nm emission compared to uncleaved nanoparticles. (C) shows that the disulfide cleavage induces PEG shedding and increases nanoparticle size, each in accordance with one embodiment of the invention.

After the synthesis of FRET-bearing PEG (10), this molecule was conjugated with PLGA to formulate PLGA-(FRET)-PEG NPs. PLGA-PEG NPs are well-studied polymeric drug delivery systems, which can be used to observe the PEG-shedding effect.[9-11] To form PLGA-(FRET)-PEG copolymers, carboxyl-terminated PLGA (PLGA-COOH) was first activated using EDC/NHS to form PLGA-NHS, and then conjugated to the free amine of the FRET-bearing PEG molecule (10). By using the nanoprecipitation method as previously reported, PLGA-(FRET)-PEG NPs with sizes that are approximately 100-120 nm were formulated.[9] The NP structure is depicted in FIG. 24A, where the hydrophobic PLGA core was stabilized by the surrounding hydrophilic PEG layer, and the disulfide-based FRET pair was located at the interface of hydrophobic and hydrophilic sections.

The fluorescent emission of PLGA-(FRET)-PEG NPs in response to a reducing stimulus was examined. Initially, analysis by fluorescence emission spectroscopy showed a weak absorption at 520 nm (FIG. 24B). After the addition of 1 mM dithiothreitol (DTT, disulfide cleavage reagent), the emission at 520 nm increased nearly 6-fold. This increase in fluorescence emission at 520 nm resulted from disulfide cleavage which abolished intramolecular FRET quenching by the Dabcyl molecule. To further confirm that the disulfide cleavage leads to PEG shedding, NP sizes were monitored after the addition of 1 mM DTT. As shown in FIG. 24C, DTT rapidly induced an increase in the size of PLGA-(FRET)-PEG NPs. In non-cleavable PLGA-PEG NP controls, a similar size increase was not observed. This NP size increase resulted from particle destabilization and aggregation upon DTT addition, confirming that disulfide cleavage leads to the loss of the stabilizing PEG layer.[7]

To demonstrate that it was possible to directly measure PEG shedding during NP interaction with target cells, folate-targeted NPs were formulated by blending PLGA-(FRET)-PEG with 10 wt % of PLGA-PEG-folate copolymers, followed by nanoprecipitation and self-assembly of NPs. NPs formulated using this method showed preferential targeting to the folate receptor on human nasopharyngeal epidermoid carcinoma (KB) cells and exhibited enhanced cell uptake through receptor-mediated endocytosis.

Figure 25:
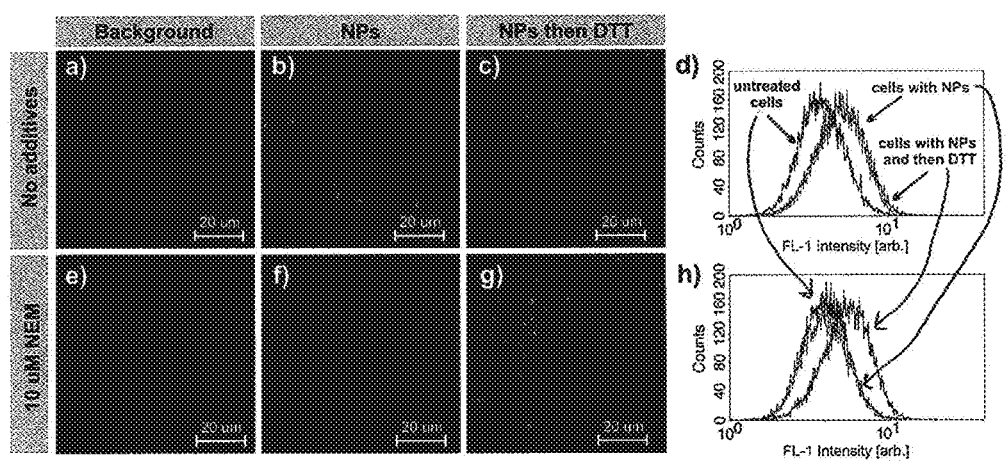
FIG. 25 demonstrates intracellular PEG shedding by fluorescent microscopy and flow cytometry in: (A)-(D) KB cells with no NEM and (E)-(H) KB cells with addition of NEM. In each row, the fluorescent intensity at 520 nm was compared among cell-only controls, cells incubated with NPs, and cells incubated with NPs followed by DTT treatment. In all experiments, the NP concentration was 1 mg/mL. The DTT concentration was 100 µM and the NEM concentration was 10 µM, each in accordance with one embodiment of the invention.
Figure 26:
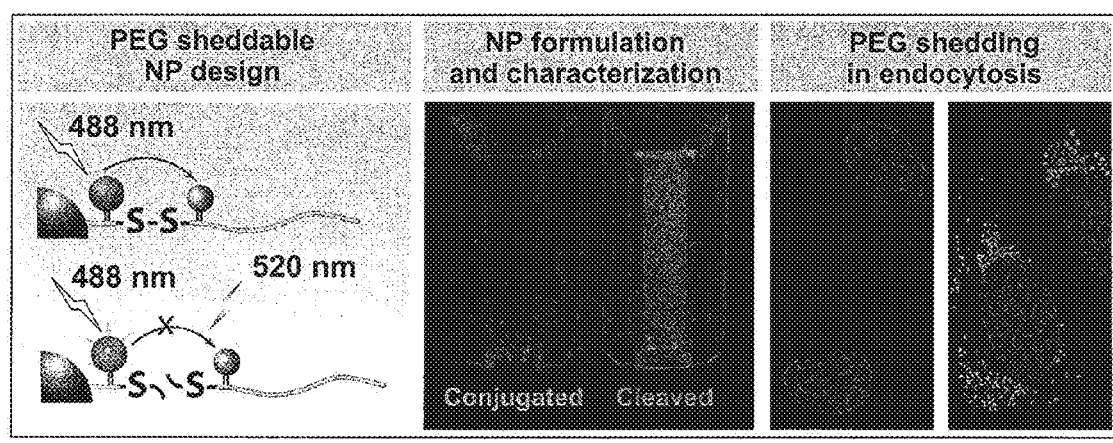
FIG. 26 demonstrates that a novel FRET-bearing PEG conjugate fluoresces at 520 nm when it is cleaved off from NPs, in accordance with one embodiment of the invention. When the NPs were targeted to cancer cell lines, the reducing redox of the endosomal compartment caused disulfide bond cleavage and shedding of the PEG layer. The fluorescence emission can be suppressed by N-ethylmaleimide to inhibit disulfide cleavage and restored by dithiothreitol, a disulfide cleavage reagent, indicating a direct correlation between fluorescence emission and PEG shedding.

PEG-shedding during NP endocytosis in KB cells was examined by confocal microscopy. Images of KB cells without NP treatment were taken as background controls (FIG. 25A). After the cells were incubated with 1 mg/mL NPs for 4 hrs, green fluorescence signals was observed in the perinuclear region (FIG. 25B). The visible green fluorescence indicated that PEG shedding had taken place after the NP endocytosis in KB cells. As a positive control to confirm that the fluorescence was due to intracellular disulfide cleavage and not unquenched OG488 emission, the cells were further treated with 100 μM DTT after NP incubation. After DTT treatment, the fluorescent image (FIG. 25C) showed similar intensity of green fluorescence (FIG. 25B), confirming that the positive readout was indeed caused by disulfide cleavage and the consequent emission of fluorescence at 520 nm. Our microscopic observations were confirmed by flow cytometry analyses (FIG. 25D). The increase in green fluorescence intensity in cells incubated with NPs compared to cells without NPs indicates that disulfide cleavage and PEG shedding had taken place after NP endocytosis. Likewise, the intensity of green fluorescence remains the same after DTT treatment.

To simulate a non-reducing intracellular environment, KB cells were incubated with NPs in the presence of 10 μM N-ethylmaleimide (NEM), an irreversible and membrane-permeable thiol reagent. It has been found that NEM inhibits the ability of KB cells to cleave disulfide bonds.[12] Therefore, NEM treatment serves as a negative control to examine intracellular PEG shedding. Fluorescence images of cells treated with 10 μM NEM were first taken as background controls (FIG. 25E). After the addition of 1 mg/mL NPs, no fluorescence above the background level could be measured (FIG. 25F), suggesting that PEG shedding through disulfide cleavage was completely abolished. However, the green fluorescent signal became visible after the removal of NEM and the addition of 100 μM DTT (FIG. 25G). Flow cytometry analysis again confirmed this microscopic observation as shown in FIG. 25H. The spectrum of cells incubated with NPs overlapped with the background spectrum when the cells were NEM-treated, but shifts to higher intensity if cells were subsequently incubated with DTT. Thus, the microscopic measurements and flow cytometry analyses proved a direct correlation of the PEG-shedding effect with fluorescence emission from NPs. Taken together, these results imply that FRET-bearing PEG can serve as a sensor to report the uptake and accumulation of NPs upon PEG shedding.

Fluorescence-labeling and tracking of NP distribution in vitro and in vivo was limited by the inability to readily differentiate intracellular versus extracellular localization of NPs while creating high background signals. For example, using whole-body fluorescence imaging techniques in vivo, one may not be able to distinguish between NPs in extracellular compartments from NPs that have been taken up by target cells. With this FRET-based PEG technique, NPs can be observed only after intracellular PEG shedding, making it possible to directly equate NP fluorescence with the reducing environment of intracellular compartments.

In summary, the first direct observation of intracellular PEG shedding during NP endocytosis by synthesizing a disulfide-based FRET-bearing PEG molecule and applying it to a targeted PLGA-PEG NP model system is herein reported. Therefore, the FRET-bearing PEG molecule described here provides a useful tool to study the PEG shedding process and aid the design of environmentally sensitive NP systems for improved drug delivery. More broadly, the sheddable PEG designed in this study is applicable to NPs where PEG or other functionalization is needed, including liposomes, polymeric micelles, lipoplexes and polyplexes, and can be tested under various conditions.

REFERENCES

[1] R. Langer, *Nature* 1998, 392, 5.
[2] D. E. Owens, N. A. Peppas, *Int. J. Pharm.* 2005, 307, 93.
[3] L. Zhang, F. Gu, J. Chan, A. Wang, R. Langer, O. C. Farokhzad, *Clin. Pharmacol. Ther.* 2008, 83, 761.
[4] R. L. Hong, C. J. Huang, Y. L. Tseng, V. F. Pang, S. T. Chen, J. J. Liu, F. H. Chang, *Clin. Cancer Res.* 1999, 5, 3645.
[5] M. J. Parr, D. Masin, P. R. Cullis, M. B. Bally, *J. Pharmacol. Exp. Ther.* 1997, 280, 1319.
[6] B. Romberg, W. E. Hennink, G. Storm, *Pharm. Res.* 2008, 25, 55.
[7] S. Takae, K. Miyata, M. Oba, T. Ishii, N. Nishiyama, K. Itaka, Y. Yamasaki, K. Koyama, K. Kataoka, *J. of Am. Chem. Soc.* 2008, 130, 6001.
[8] S. Cerritelli, D. Velluto, J. A. Hubbell, *Biomacromolecules* 2007, 8, 1966.
[9] J. Cheng, B. A. Teplya, I. Sherifi, J. Sung, G. Luther, F. X. Gu, E. Levy-Nissenbaum, A. F. Radovic-Moreno, R. Langer, O. C. Farokhzad, *Biomaterials* 2007, 28, 869.
[10] O. C. Farokhzad, J. Cheng, B. A. Teply, I. Sherifi, S. Jon, P. W. Kantoff, J. P. Richie, R. Langer, *Proc. Natl. Acad. Sci. U.S.A.* 2006, 103, 6315.
[11] F. Gu, L. Zhang, B. A. Teply, N. Mann, A. Wang, A. F. Radovic-Moreno, R. Langer, O. C. Farokhzad, *Proc. Natl. Acad. Sci. U.S.A.* 2007, 105, 2586.
[12] J. Yang, H. Chen, I. R. Vlahov, J.-X. Cheng, P. S. Low, *Proc. Natl. Acad. Sci. U.S.A.* 2006, 103, 13872.

Example 10

Materials & Methods

Pentaethylenehexamine (PEHA), protamine, poly-L-histidine (PLH, 6-mer) (custom made) and all other chemicals, unless otherwise stated, were purchased from Sigma-Aldrich Chemical. Red blood cells (RBCs) were procured from Bio Chemed Services (Winchester, Va.).

The PEHA (1 mM), PLH (1 mM), protamine (0.1 mM) and Triton X-100 (1%, w/v) were dissolved in phosphate buffered saline (PBS) with pH adjusted to 7.4, 6.5, or 5.4 as stock solutions. The red blood cells (RBCs) were separated from the whole blood or anticoagulant solution by centrifuging the whole blood at 800 rcf for 15 min. The supernatant was discarded and the RBCs were washed thrice with phosphate buffered saline (PBS). The stock of RBCs was prepared by mixing three volumes of the centrifuged RBCs with 11 parts of the phosphate buffered saline (PBS) with pH adjusted to 7.4, 6.5, or 5.4, and 100 μL of this stock was used for 1 ml of the sample. RBCs were mixed with Triton X-100 (1%, w/v) (positive control); with phosphate buffered saline (PBS) with pH adjusted to 7.4, 6.5, or 5.4 (negative control); and respective concentrations of amines, PLH and protamine at different pH (7.4, 6.5, or 5.4). Samples were incubated at 37° C. for 24 h on a tube shaker. The samples were centrifuged at 800 rcf for 15 min to separate intact RBCs. The supernatant was collected and kept for 30 min at room temperature to oxidize hemoglobin (Hb) and then the absorbance of Oxy-Hb was measured spectrophotometrically at 540 nm. The relative hemolysis efficiency was calculated as the percentage of released hemoglobin by the samples to that by Triton X-100. The percent hemolysis was calculated using the equation of a straight line, y=mx+c, where % hemolysis (x)=[optical density (y)−negative control optical density (c)]/[(positive control optical density−negative control optical density)/100] (m).

Results

In order to understand the effect of PLH in comparison to other amine rich compounds, on the integrity of the cell membrane the in vitro hemolytic assay was performed at different pH conditions (physiological pH 7.4, early endosomal pH 6.5 and late endosomal pH 5.4). The release of hemoglobin from the RBC's was used as a measure of lytic property of the compound at different pH conditions. Briefly, RBCs were washed and diluted with the PBS at different pH (7.4, 6.5 & 5.4) and incubated with the samples (PLH, PEHA and protamine) at the respective pH (37° C., 24 h), on a tube shaker. Thereafter, the Intact RBCs were separated by centrifugation (800 g, 15 min), and the supernatant was kept at room temperature for 30 min to oxidise hemoglobin (Hb) to Oxy-Hb, which absorbs spectroscopically at 540 nm. The percent hemolysis for the samples was calculated with respect to Triton-X-100, which is considered to give complete lysis of RBCs (100%) and RBCs incubated with PBS at the respective pH (7.4, 6.5 & 5.4) were used for zero percent correction. The graph of % hemolysis versus pH for various samples shows that PLH gives maximum hemolytic properties at endosomal pH 5.4, in comparison to PEHA and Protamine, which bear more hemolytic properties at physiological pH 7.4. Therefore, the results demonstrates that polyhistidine can cause rupture when the pH drops, such as in the endosome, but not in the cytosol.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The citation of any reference provided herein is not an admission that the reference is indeed prior art.

What is claimed is:

1. A polymeric particle formed by self-assembly of one or more copolymers consisting of a first pH sensitive covalent copolymer conjugate and optionally a second pH insensitive covalent copolymer conjugate, wherein the first covalent copolymer conjugate has the following formula:

$$A_1\text{-}B\text{-}C_1$$

wherein the second covalent copolymer conjugate has the following formula:

$$A_2\text{-}C_2$$

wherein $A_1$ and $A_2$ are hydrophobic biodegradable polymers; B is a positively charged pH sensitive polymer; and $C_1$ and $C_2$ are hydrophilic polymers, and wherein the self-assembled polymeric particle comprises a core formed of the hydrophobic biodegradable polymer, the hydrophilic polymer forms the surface of the polymeric particle, and the positively charged pH sensitive polymer is present between the core and the hydrophilic polymer surface, wherein the particle does not include a targeting ligand or moiety.

2. The particle of claim 1, wherein $A_1$ is polylactic acid, polyglycolic acid or poly(lactide-co-glycolide) conjugated to B which is a polyhistidine conjugated to $C_1$ which is a polyethylene glycol.

3. The particle of claim 1 further comprising an agent to be delivered.

4. A composition comprising one or more of the particles of claim 1 and a pharmaceutically acceptable carrier.

5. The particle of claim 1, wherein the positively charged pH sensitive polymer is selected from the group consisting of polyhistidine, polylysine, polyarginine, a copolymer of histidine and lysine, a copolymer of histidine and arginine, a copolymer of lysine and arginine, poly(ethylene imine), and poly(beta amino ester).

6. The particle of claim 1, wherein the hydrophobic biodegradable polymer is selected from the group consisting of polyester, polyanhydride, poly(ortho ester), poly(caprolactone), poly(ethylene imine), poly(acrylic acid), poly(urethane), and combinations thereof.

7. The particle of claim 1, wherein the hydrophilic polymer is a polyalkylene glycol or a polyalkylene oxide.

8. The particle of claim 1, wherein the positively charged pH sensitive polymer is covalently conjugated to the hydrophobic biodegradable polymer, hydrophilic polymer or both via a cleavable bond selected from the group consisting of a pH-cleavable bond, a redox-active cleavable bond, and an enzymatically cleavable bond.

9. The particle of claim 8, wherein the cleavable bond is selected from the group consisting of diorthoester, orthoester, vinylether, phosphoroamidate, hydrazone, beta-thiopropionate, low pKa polyplex, disulfide, redox-sensitive chimeric polypeptide linker, alpha-helical linker with redox sensitive motifs, alpha-helix with embedded adjacent or dispersed vicinal cysteine residues, and protease-cleavable peptide bond.

10. The particle of claim 9, wherein the cleavable bond comprises a disulfide bond.

11. The particle of claim 9, wherein the positively charged pH sensitive polymer is a polyhistidine, the hydrophobic polymer is polylactic-co-glycolic acid), the hydrophilic polymer is polyethylene glycol, the polyhistidine is covalently conjugated to the poly(lactic-co-glycolic acid) via an amide bond and the polyethylene glycol is covalently conjugated to the polyhistidine via a disulfide bond.

12. The particle of claim 1, wherein the zeta potential difference of the particle at a physiological pH relative to an endosomal pH is at least 5 millivolts, or wherein the zeta potential of the particle is more positive at an endosomal pH than at a physiological pH.

13. The particle of claim 1, wherein $A_1$ and $A_2$ are the same, $C_1$ and $C_2$ are the same, or both.

14. The particle of claim 1, wherein $A_2$ is poly(lactic-co-glycolic acid) and $C_2$ is polyethylene glycol.

15. A polymeric particle formed by self-assembly of one or more copolymers consisting of a first pH sensitive covalent copolymer conjugate and a second pH insensitive covalent copolymer conjugate, wherein the first covalent copolymer conjugate has the following formula:

$A_1$-B-$C_1$ wherein the second covalent copolymer conjugate has the following formula:

$A_2$-$C_2$ wherein $A_1$ and $A_2$ are hydrophobic biodegradable polymers; B is a positively charged pH sensitive polymer; and $C_1$ and $C_2$ are hydrophilic polymers, and wherein the self-assembled polymeric particle comprises a core formed of the hydrophobic biodegradable polymer, the hydrophilic polymer forms the surface of the polymeric particle, and the positively charged pH sensitive polymer is present between the core and the hydrophilic polymer surface, wherein the particle does not include a targeting ligand or moiety.

16. The particle of claim 1 having encapsulated therein one or more pharmaceutical agents selected from the group consisting of antiinfectives, antineoplastic or cytostatic agents and anti-inflammatory agents.

17. The particle of claim 11, wherein $A_2$ is polylactic acid, polyglycolic acid or poly(lactide-co-glycolide) and $C_2$ is polyalkylene oxide.

18. The particle of claim 17, wherein the polyalkylene oxide is polyethylene glycol.

19. A method, comprising:
administering the composition of claim 4 to a subject.

* * * * *